(12) United States Patent
Jones et al.

(10) Patent No.: US 9,074,217 B2
(45) Date of Patent: Jul. 7, 2015

(54) METHODS OF INCREASING PLANT GROWTH

(75) Inventors: Brian Jones, Sydney (AU); Jiehua Wang, Tianjin (CN); Goran Sandberg, Umea (SE)

(73) Assignee: SWETREE TECHNOLOGIES AB, Umea (SE)

( * ) Notice: Subject to any disclaimer, the term of this patent is extended or adjusted under 35 U.S.C. 154(b) by 889 days.

(21) Appl. No.: 12/595,484

(22) PCT Filed: Apr. 10, 2008

(86) PCT No.: PCT/IB2008/001482
§ 371 (c)(1),
(2), (4) Date: Oct. 9, 2009

(87) PCT Pub. No.: WO2008/125983
PCT Pub. Date: Oct. 23, 2008

(65) Prior Publication Data
US 2010/0287654 A1    Nov. 11, 2010

(51) Int. Cl.
*C12N 15/82* (2006.01)
*C07K 14/415* (2006.01)

(52) U.S. Cl.
CPC ........ *C12N 15/8262* (2013.01); *C12N 15/8218* (2013.01); *C12N 15/8241* (2013.01); *C07K 14/415* (2013.01)

(58) Field of Classification Search
None
See application file for complete search history.

(56) References Cited

U.S. PATENT DOCUMENTS 6,927,320 B1 *  8/2005  Benfey et al. ................. 800/287
7,635,800 B2 * 12/2009  Ratcliffe et al. .............. 800/290

OTHER PUBLICATIONS

Colliver et al (1997, Plant Mol. Biol. 35:509-522).*
Montgomery et al (Trends in Genetics, Jul. 1998, 14(7):255-258).*
Benfey et al., "Root Development in *Arabidopsis*: Four Mutants With Dramatically Altered Root Morphogenesis", *Development*, vol. 119, pp. 57-70, 1993.
Cui et al., "An evolutionarily conserved mechanism delimiting SHR movement defines a single layer of endodermis in plants", *Science*, vol. 316, No. 5823, pp. 421-425, 2007.
Levesque et al., "Whole-Genome Analysis of the Short-Root Developmental Pathway of *Arabidopsis*", *PLoS Biology*, vol. 4, No. 5, e 143; pp. 739-752, 2006.
Nakajima et al., "Intercellular movement of the putative transcription factor SHR in root patterning", *Nature*, vol. 413, No. 6853, pp. 307-311, 2001.
Accession No. AC216941, Database EMBL [online], "*Populus trichocarpa* clone POP023-N18, complete sequence", 2008 (3 pages).
Accession No. A8R3J0, Database UniProt [online], "SubName: Full=Putative Short-Root protein", 2008 (2 pages).

* cited by examiner

*Primary Examiner* — Stuart F Baum
(74) *Attorney, Agent, or Firm* — Klarquist Sparkman, LLP

(57) ABSTRACT

This invention relates to methods of increasing the growth and/or biomass of plants by partially suppressing the expression of a SHORT-ROOT (SHR) polypeptide, such as AtSHR or PtSHR1. Manipulation of SHORT-ROOT expression may be useful, for example, in accelerating growth and increasing biomass production in transgenic plants.

13 Claims, 16 Drawing Sheets

Figure 2

```
            . . . .10 . . . .20 . . . .30 . . . .40 . . . .50 . . . .60 . . . .70 . . . .80 . . . .90 . . . 100
AtSHR       1:MDTLFRLVSLQQQQQSDSIITNQSSLSRISTTTTGSPQTAYHYNFPQNDVVEECFNFFMDEEDLSSSSSHHNHHHNNNPNTYYSPFTTPTQYHPATSSTP:100
PtSHR1      1:MDTLFRLVSLQQQQSEQ.....SFNSTSRISSSSRSSRQNNNHHHHIYQQEDPECFNFFMDEEDFSSSSSKHYYPPYHHNQQQQHQHQTTTTTPTTTTTNT:95
PtSHR2A     1:......................MQSNSSNNNNNQPQTSHTSTSISSDSGEACG..........................................:31
PtSHR2B     1:......................MQSNSSNNNNNQPQTSHTSTSISSDSGEACG..........................................:31

. . . 110 . . . 120 . . . 130 . . . 140 . . . 150 . . . 160 . . . 170 . . . 180 . . . 190 . . . 200
AtSHR       101:SSTAAAAALASPYSSSGHHNDPSAFSIPQTPPSFDFSINAKWADSVILEAARAFSDKDTAIAQQILWTLNELSSPYGDTEQKLASYFLQALFNIMTGSGE:200
PtSHR1      96:S............TPSTHHVLDSADFSFSPSHDLNFEFSGKWVIDILLESAHAIDKNSARLQQLIWMLNELCSPYGDTEQKLASYFLQALFSIMNDSGE:183
PtSHR2A     31:...................................IGNKWASRILSECARAISEKDSSKIHNLLWMLNELASPYGDCEQKLASHFLQALFCIATDSGQ:94
PtSHR2B     31:...................................IGNKWASKILSECARAISEKDSSKIHHLLWMLNELASPYGDCDQKLASYFLQALFCIATESGQ:94

. . . 210 . . . 220 . . . 230 . . . 240 . . . 250 . . . 260 . . . 270 . . . 280 . . . 290 . . . 300
PtSHR2A     95:RCIKT..LTIVAEKSHSFDSARKLILKFQEVSPWITFGHVASNGAILEALDCASKLHIIDISHTLCTQWPTLLEALATRNDTPHLKLTVVVTAS.....:187
PtSHR2B     95:RCIKT..LTIVAEKSHSFDSARKLILKFQEVSPWITFGHVASNGAILEALDGESKLHIIDISNTLCTQWPTLLEALATRNDTPRLKLTVVVTAS.....:187
AtSHR       201:RCYKTMVTAAATEKICSFESTRKTVLKFQEVSPWATFGHVAANGAILEAVDGEAKIHIVDISSTFCTQWPTLLEALATRSDDTPHLKLTTVVVANKFVN.:299
PtSHR1      184:RCYRI..TLASASEKICSFDSTRKMVLKFQEVSPWITFGHVSCNGAIMEAFEGESKLHIIDISNTYCTQWPTLLEALATRIDETPHLKLTTVVASKSSGNN:281
                                                                           VHIID

. . . 310 . . . 320 . . . 330 . . . 340 . . . 350 . . . 360 . . . 370 . . . 380 . . . 390 . . . 400
AtSHR       299:.......DQTASIRVMKEIGNRMEKFARLMGVPFKFNIIHHVGDLSEFDLNELDVKPDEVLAINCVGAMHGIASRGSPRDAVISSFRRLRPRIVTVVEEE:392
PtSHR1      282:IGLTSTGGLASVIKVMKEIGNRMEKFARLMGVPFKFNVIHHAGDLCCLNLAELDVKDDEALAINCVGALISITPASRRRDYVISSFRILQPRIITVVEEE:381
PtSHR2A     187:..........IVISVMKEIGQRMEKFARLMGVPFELNVISGINHLGELTKDRLVQEDEAVAINCGALIRYGVE..ERNSVIQMFQSLNPRVVTIVEEE:275
PtSHR2B     187:..........IVISVMKEIGQRMEKFARLMGVPFEFKVISVINHIGELTKEGLGVQEDEAVAINCIGALIRRYEVD..ERSSVIQLFRSLNPRVVTIVEEE:275

. . . 410 . . . 420 . . . 430 . . . 440 . . . 450 . . . 460 . . . 470 . . . 480 . . . 490 . . . 500
AtSHR       393:ADLVGEEEGGFDDEILRGFGECLRWIRICFESWEESFPRTSNERLMLERAAGRAIVDIVACEPSDS...TERRETIRKWSRRIRNSEFGAVGYSDEVADD:489
PtSHR1      382:ADLDG.......LDEVKGFQECLRWIRVIFESLDESFPRTSNEQLMLERAAGRAIVDIVACPPSDS...IERRETIATRWSGRLISCGFSPIIFSDEVCDD:471
PtSHR2A     276:ADFTSSR.....YDEVKCFEECLRYYTLIYFEMLEESFVPTSNERLMLERECSRNIVRVIACDEGNDGGECERRERCSQWFERLR.EAFSPVGFSDVVDD:369
PtSHR2B     276:ADFTSSR.....YDEVKCFEECLRYYTLIYFEMLEESFVPTSNERLMLERECSRNIVRVIACDEETGGGECERRERCVQWSERLR.EAFSPVGFSDIVDD:369

. . . 510 . . . 520 . . . 530 . . . 540 .
AtSHR       490:VRALLRRYKEGVWSIVYQCPDAAG.IFLCWRDQPVVWASAWRPT:531    SEQ ID NO: 28
PtSHR1      472:VKALLKRYKEG.WSITQCGDAG..IFLCWKEQPVVWASAWRP.:510    SEQ ID NO: 2
PtSHR2A     370:VKALLKRYRAGWALVIPQGDHDSGIYITWKEEPVVWASAWKP.:411    SEQ ID NO: 4
PtSHR2B     370:VKALLKRYRAGWALVIPQGDHESGIYITWKEEPVVWASAWKP.:411    SEQ ID NO: 6
                                        SAW
```

Figure 3

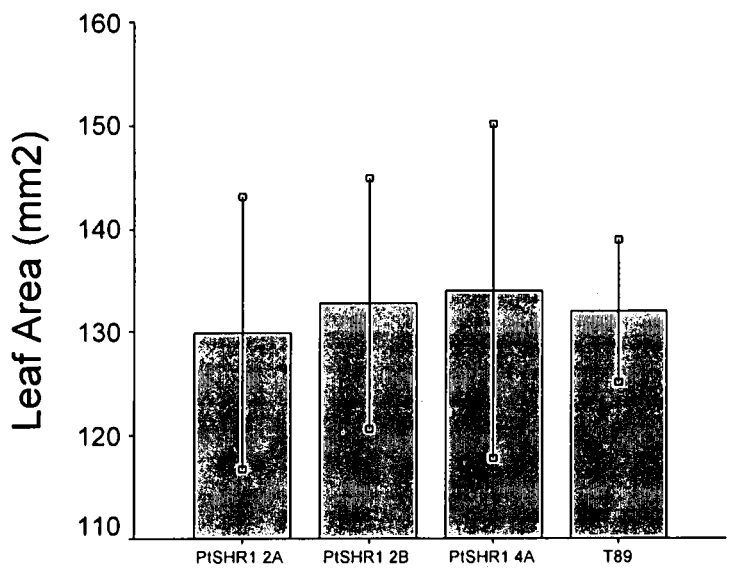
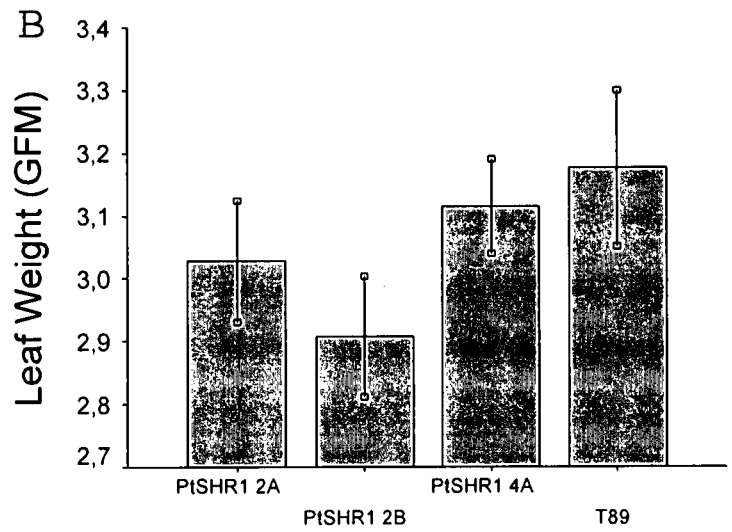
Figure 11

Figure 15

METHODS OF INCREASING PLANT GROWTH

CROSS REFERENCE TO RELATED APPLICATIONS

This is the U.S. National Stage of International Application No. PCT/IB2008/001482, filed Apr. 10, 2008, which was published in English under PCT Article 21(2), which in turn claims the benefit of U.K. Provisional Application No. 0707089.9, filed Apr. 12, 2007. Both applications are incorporated herein in their entirety.

This invention relates to methods of increasing the growth of plants.

Long-term energy security is both a challenge and an opportunity. From the wide range of options currently available, renewable biomass resources offer a very real alternative to fossil fuels. Biomass production provides a carbon-neutral, renewable means of supplying bioenergy and biomaterial resources. Biomass production in short-rotation biomass plantations in Sweden currently averages 8 dry Mg $ha^{-1}$ $year^{-1}$ and in the United States 10 to 22 dry Mg $ha^{-1}$ $year^{-1}$ (for short-rotation woody crops) (Ragauskas et al. 2006. Science Vol. 113, 484-489).

Plants, like animals, require a supply of new cells for growth and development. Biomass accumulation in woody plant species begins with cell divisions in the primary and secondary meristems. Meristems are the plant stem cell niches. The primary, apical meristems provide cells for root and shoot tip growth. A circumferential secondary meristem, called the vascular cambium (VC), is located towards the exterior of trees and other woody species. Wood is derived from cell proliferation in the VC. Surprisingly, given its importance to commerce and the environment, although there has been a long tradition of anatomical and physiological analysis of the VC, almost nothing is known of the molecular bases of its establishment and function. Even the cellular components that comprise the VC stem cell niche have remained unidentified.

The *Arabidopsis* SHORT-ROOT (AtSHR) gene has been shown to play critical roles in the establishment and maintenance of the root apical meristem. In the *Arabidopsis* root, the SHORT-ROOT (AtSHR) protein, along with SCARECROW (AtSCR) and the PLETHORA (AtPLT1 and AtPLT2) proteins, is essential for the specification and maintenance of the QC and the abutting stem cell populations (Levesque et al. PLoS Biol. 2006 4(5):e143). Loss-of-function shr mutants exhibit a progressive disorganization of the QC, a loss of stem cell activity and the cessation of root tip growth (Levesque et al., PLoS Biol. 2006 May; 4(5): e143.). AtSHR is transcribed in the inner layers of the stele and the protein moves to the nucleus of cells in the adjacent AtSCR-expressing, QC, endodermis and endodermal/cortex initials and daughter cells (Nakajima et al., Nature. 2001 Sep. 20; 413(6853):307-11).

In combination with the role in QC and stem cell fate determination, AtSHR is a key regulator of asymmetric division in the *Arabidopsis* root apex. Together with AtSCR, AtSHR is essential for the asymmetric periclinal division of the cortex/endodermal stem cell daughter (Helariutta et al., Cell. 2000 May 26; 101(5):555-67). Cortical/endodermal cell fate separation of the daughter cells of this division relies on the degradation of AtSHR and AtSCR in the outer cell and the maintenance of AtSHR in the inner, endodermal cell (Helariutta et al., Cell. 2000 May 26; 101(5):555-67). Finally, as the root ages, a second cortical layer is produced through the asymmetric division of the endodermis. AtSHR is critical for this division and in this instance it operates through an AtSCR-independent mechanism (Paquette and Benfey Plant Physiol. 2005 June; 138(2):636-40).

A complete loss of AtSHR function is clearly detrimental to growth in *Arabidopsis*, as both the roots and shoots of shr mutants are severely dwarfed compared to the WT (Benfey et al., Development. 1993 September; 119(1):57-70).

It has also been reported that ectopic expression of AtSHR in transgenic *Arabidopsis* plants, driven by either the CaMV 35S, AtSCR or WEREWOLF (AtWER) promoters, can result in a modification of radial patterning in *Arabidopsis* root tips (Benfey et al., Cell, Vol. 101, 2000; Nakajima et al., 2001 Nature; Sena et al., 2004, Development). This radial patterning defect occurs through a multiplication of cell layers originating in the root meristem (Benfey et al., Cell, Vol. 101, 555-567, 2000). Sena et al. (2004) suggested that the supernumerary layers in AtWERpromoter:AtSHR transgenic plants originated from the ectopic expression of AtSHR occurring in the epidermal/lateral root cap initials (stem cells) rather than in the progeny of these cells.

Although AtSHR is essential for root development, the mechanisms involved in cell-to-cell movement of the protein and its precise cell autonomous and non-cell-autonomous modes of action have yet to be determined.

The present inventors have discovered that, whereas a complete loss-of-function of AtSHR leads to the degeneration of the root apical meristem and a dwarfing or *Arabidopsis* shoots, a partial suppression of the steady-state mRNA levels of AtSHR or the Poplar SHORT-ROOT1 (PtSHR1) resulted in a dramatic and sustained increase in the activities of the shoot primary (tip growth) and secondary (girth growth) meristems. Manipulation of SHORT-ROOT expression may therefore be useful in accelerating growth and increasing biomass production in transgenic plants.

An aspect of the invention provides a method of increasing the growth and/or biomass of a plant comprising;
  altering the expression of a SHORT-ROOT (SHR) polypeptide within cells of said plant.

Expression of the SHORT-ROOT (SHR) polypeptide may be altered relative to control plants, for example wild-type plants.

Alteration of SHORT-ROOT (SHR) expression may increase the rate of post-germination development of plants. For example, alteration of SHORT-ROOT (SHR) polypeptide expression within cells of the plant may increase the rate of primary (height) and secondary (girth) growth and/or the rate of accumulation of biomass in plant.

Increased growth or biomass may occur in the above-ground portion of a plant e.g. in the stems and other aerial structures of the plant, relative to control plants. The above-ground portion of a plant may therefore have, increased primary (height) and secondary (girth) growth and/or increased biomass relative to control plants. In a woody plant, the wood density may be increased.

Alteration of SHORT-ROOT (SHR) polypeptide expression within cells of the plant may also increase the rate of germination of the plant.

Growth may be increased by an overall increase in cell number, for example, the pith, vasculature and cortex may be proportionately greater in plants treated as described herein than in control plants.

SHORT-ROOT (SHR) polypeptides are members of the GRAS superfamily of transcription factors. Transcription factors of the GRAS superfamily share a variable amino-terminus and a highly conserved carboxyl-terminus that contains a variety of recognisable motifs (Bolle C., Planta. 2004 March; 218(5):683-92). SHR polypeptides, such as AtSHR, PtSHR1, PtSHR2A and PtSHR2B share a number of conserved sequences between them that are not shared by other GRAS functional classes (see FIG. 3 for conserved sequences and Bolle C., Planta. 2004 March; 218(5):683-92) for GRAS domains).

A SHORT-ROOT (SHR) polypeptide may fall within the SHR clade, as shown in FIG. 1 for AtSHR, PtSHR1, PtSHR2A and PtSHR2B, in a cladogram of other GRAS protein sequences, in particular sequences of Scarecrow-like (SCL) proteins such as PtSCL35b, PtSCL53b, PtSCL62, PtSCL69b, PtSCL92b, PtSCL97b, AtSCL29 and AtSCL32. A cladogram may be produced using conventional techniques. For example, a cladogram may be calculated using ClustalW to align the protein sequences, Phylip format for tree output, with 1000 bootstrap replicates and TreeViewX (version 0.5.0) for visualisation.

A suitable SHORT-ROOT (SHR) polypeptide may have the amino acid sequence of any one of SEQ ID NOS: 2, 4, 6, 8, 10, 12, 14 or 16 or may be a fragment or variant of this sequence which retains SHR activity.

In some preferred embodiments, a SHORT-ROOT (SHR) polypeptide may have the amino acid sequence of SEQ ID NO:2 (PU04350_eugene3.01860017), SEQ ID NO:4 (eugene3.00070144) or SEQ ID NO:6 (eugene3.00640143) or may be a fragment or variant of this sequence which retains SHR activity.

A SHORT-ROOT (SHR) polypeptide which is a variant a reference SHR sequence set out herein, such as SEQ ID NO: 2, may comprise an amino acid sequence which shares greater than 30% sequence identity with the reference SHR amino acid sequence, preferably greater than 40%, greater than 50%, greater than 60%, greater than 65%, greater than 70%, greater than 80%, greater than 90% or greater than 95%.

Particular amino acid sequence variants may differ from a known SHR polypeptide sequence as described herein by insertion, addition, substitution or deletion of 1 amino acid, 2, 3, 4, 5-10, 10-20 20-30, 30-50, or more than 50 amino acids.

Sequence similarity and identity are commonly defined with reference to the algorithm GAP (Wisconsin Package, Accelerys, San Diego USA). GAP uses the Needleman and Wunsch algorithm to align two complete sequences that maximizes the number of matches and minimizes the number of gaps. Generally, default parameters are used, with a gap creation penalty=12 and gap extension penalty=4.

Use of GAP may be preferred but other algorithms may be used, e.g. BLAST (which uses the method of Altschul et al. (1990) J. Mol. Biol. 215: 405-410), FASTA (which uses the method of Pearson and Lipman (1988) PNAS USA 85: 2444-2448), or the Smith-Waterman algorithm (Smith and Waterman (1981) J. Mol. Biol. 147: 195-197), or the TBLASTN program, of Altschul et al. (1990) supra, generally employing default parameters. In particular, the psi-Blast algorithm (Nucl. Acids Res. (1997) 25 3389-3402) may be used.

Sequence comparison may be made over the full-length of the relevant sequence described herein, or may be over a contiguous sequence (i.e. a 'window') of at least 50, 75, 100, 150 or more amino acids or nucleotide triplets, compared with the relevant amino acid sequence or nucleotide sequence.

Certain domains of a SHORT-ROOT (SHR) polypeptide may show an increased level of identity with domains of a SHR reference sequence, such as SEQ ID NO: 2, 4 or 6, relative to the SHORT-ROOT (SHR) polypeptide sequence as a whole. For example, a SHORT-ROOT (SHR) polypeptide may comprise one or more domains or motifs having an amino acid sequence which has at least 80%, at least 90%, at least 95%, or at least 98% sequence identity or similarity, with an amino acid sequence selected from the group consisting of SEQ ID NO: 17, SEQ ID NO: 18, SEQ ID NO: 19, SEQ ID NO: 20 and SEQ ID NO: 21. In some preferred embodiments, a SHORT-ROOT (SHR) polypeptide may comprise one or more domains or motifs having an amino acid sequence which his selected from the group consisting of SEQ ID NO: 17, SEQ ID NO: 18, SEQ ID NO: 19, SEQ ID NO:20 and SEQ ID NO:21.

In some embodiments, expression of the SHORT-ROOT (SHR) polypeptide may be reduced within cells of said plant. Reduction in this context excludes complete abolition of expression. For example, expression of the SHORT-ROOT (SHR) polypeptide may be reduced within cells of said plant by up to 90%, up to 80%, up to 70%, up to 60%, up to 50% up to 40% or up to 30%. In other words, expression of the SHORT-ROOT (SHR) polypeptide in the plant may be 0.1 fold, 0.2 fold, 0.3 fold, 0.4 fold, 0.5 fold, 0.6 fold or 0.7 fold of the expression within cells of control plants.

Reduction of SHORT-ROOT (SHR) polypeptide expression as described herein may lead to an increase in plant growth or biomass. In some embodiments, the growth or biomass of the above-ground portion of the plant may be increased.

Expression of the SHORT-ROOT (SHR) polypeptide may be reduced within cells of said plant by any convenient method.

In some embodiments, expression of the SHORT-ROOT (SHR) polypeptide may be reduced by expressing a heterologous nucleic acid which encodes or transcribes a suppressor nucleic acid, for example a suppressor RNA molecule, within cells of said plant.

Nucleic acids as described herein may be wholly or partially synthetic. In particular, they may be recombinant in that nucleic acid sequences which are not found together in nature (do not run contiguously) have been ligated or otherwise combined artificially. Alternatively, they may have been synthesised directly e.g. using an automated synthesiser.

The nucleic acid may of course be double- or single-stranded, cDNA or genomic DNA, or RNA. The nucleic acid may be wholly or partially synthetic, depending on design. Naturally, the skilled person will understand that where the nucleic acid includes RNA, reference to the sequence shown should be construed as reference to the RNA equivalent, with U substituted for T.

"Heterologous" indicates that the gene/sequence of nucleotides in question or a sequence regulating the gene/sequence in question, has been introduced into said cells of the plant or an ancestor thereof, using genetic engineering or recombinant means, i.e. by human intervention. Nucleotide sequences which are heterologous to a plant cell may be non-naturally occurring in cells of that type, variety or species (i.e. exogenous or foreign) or may be sequences which are non-naturally occurring in that sub-cellular or genomic environment of the cells or may be sequences which are non-naturally regulated in the cells i.e. operably linked to a non-natural regulatory element.

The suppression of the expression of target polypeptides in plant cells is well-known in the art. A suitable suppressor nucleic acid may be a copy of all or part of the target SHR gene inserted in antisense or sense orientation or both relative to the SHR gene, to achieve reduction in expression of the SHR gene. See, for example, van der Krol et al., (1990) The Plant Cell 2, 291-299; Napoli et al., (1990) The Plant Cell 2, 279-289; Zhang et al., (1992) The Plant Cell 4, 1575-1588, and U.S. Pat. No. 5,231,020. Further refinements of this approach may be found in WO95/34668 (Biosource); Angell & Baulcombe (1997) The EMBO Journal 16, 12:3675-3684; and Voinnet & Baulcombe (1997) Nature 389: pg 553.

In some embodiments, the suppressor nucleic acid may be a sense suppressor of expression of the SHORT-ROOT (SHR) polypeptide.

A suitable sense suppressor nucleic acid may be a double stranded RNA (Fire A. et al Nature, Vol 391, (1998)). dsRNA mediated silencing is gene specific and is often termed RNA interference (RNAi). RNAi is a two step process. First, dsRNA is cleaved within the cell to yield short interfering RNAs (siRNAs) of about 21-23 nt length with 5' terminal phosphate and 3' short overhangs (~2 nt). The siRNAs target the corresponding mRNA sequence specifically for destruction (Zamore P. D. Nature Structural Biology, 8, 9, 746-750, (2001)

siRNAs (sometimes called microRNAs) down-regulate gene expression by binding to complementary RNAs and either triggering mRNA elimination (RNAi) or arresting mRNA translation into protein. siRNA may be derived by processing of long double stranded RNAs and when found in nature are typically of exogenous origin. Micro-interfering RNAs (miRNA) are endogenously encoded small non-coding RNAs, derived by processing of short hairpins. Both siRNA and miRNA can inhibit the translation of mRNAs bearing partially complementary target sequences without RNA cleavage and degrade mRNAs bearing fully complementary sequences.

Accordingly, the present invention provides the use of RNAi sequences based on the SHORT-ROOT (SHR) nucleic acid sequence for suppression of the expression of the SHORT-ROOT (SHR) polypeptide. For example, an RNAi sequence may correspond to a fragment of SEQ ID NO: 1, 3, 5, 7, 9, 11, 13, 15 or a variant thereof.

siRNA molecules are typically double stranded and, in order to optimise the effectiveness of RNA mediated down-regulation of the function of a target gene, it is preferred that the length and sequence of the siRNA molecule is chosen to ensure correct recognition of the siRNA by the RISC complex that mediates the recognition by the siRNA of the mRNA target and so that the siRNA is short enough to reduce a host response.

miRNA ligands are typically single stranded and have regions that are partially complementary enabling the ligands to form a hairpin. miRNAs are RNA sequences which are transcribed from DNA, but are not translated into protein. A DNA sequence that codes for a miRNA is longer than the miRNA. This DNA sequence includes the miRNA sequence and an approximate reverse complement. When this DNA sequence is transcribed into a single-stranded RNA molecule, the miRNA sequence and its reverse-complement base pair to form a partially double stranded RNA segment. The design of microRNA sequences is discussed on John et al, PLoS Biology, 11(2), 1862-1879, 2004.

Typically, the RNA molecules intended to mimic the effects of siRNA or miRNA have between 10 and 40 ribonucleotides (or synthetic analogues thereof), more preferably between 17 and 30 ribonucleotides, more preferably between 19 and 25 ribonucleotides and most preferably between 21 and 23 ribonucleotides. In some embodiments of the invention employing double-stranded siRNA, the molecule may have symmetric 3' overhangs, e.g. of one or two (ribo)nucleotides, typically a UU of dTdT 3' overhang. Based on the disclosure provided herein, the skilled person can readily design suitable siRNA and miRNA sequences, for example using resources such as Ambion's siRNA finder, see the World Wide Web at ambion.com/techlib/misc/siRNA_finder.html. siRNA and miRNA sequences can be synthetically produced and added exogenously to cause gene downregulation or produced using expression systems (e.g. vectors). In a preferred embodiment, the siRNA is synthesized synthetically.

Longer double stranded RNAs may be processed in the cell to produce siRNAs (see for example Myers (2003) Nature Biotechnology 21:324-328). The longer dsRNA molecule may have symmetric 3' or 5' overhangs, e.g. of one or two (ribo) nucleotides, or may have blunt ends. The longer dsRNA molecules may be 25 nucleotides or longer. Preferably, the longer dsRNA molecules are between 25 and 30 nucleotides long. More preferably, the longer dsRNA molecules are between 25 and 27 nucleotides long. Most preferably, the longer dsRNA molecules are 27 nucleotides in length. dsRNAs 30 nucleotides or more in length may be expressed using the vector pDECAP (Shinagawa et al., Genes and Dev., 17, 1340-5, 2003).

Another alternative is the expression of a short hairpin RNA molecule (shRNA) in the cell. shRNAs are more stable than synthetic siRNAs. A shRNA consists of short inverted repeats separated by a small loop sequence. One inverted repeat is complementary to the gene target. In the cell the shRNA is processed by DICER into a siRNA which degrades the target gene mRNA and suppresses expression. In a preferred embodiment the shRNA is produced endogenously (within a cell) by transcription from a vector. shRNAs may be produced within a cell by transfecting the cell with a vector encoding the shRNA sequence under control of a RNA polymerase III promoter such as the human H1 or 7SK promoter or a RNA polymerase II promoter. Alternatively, the shRNA may be synthesised exogenously (in vitro) by transcription from a vector. The shRNA may then be introduced directly into the cell. Preferably, the shRNA molecule comprises a partial sequence of SHR. For example, the shRNA sequence is between 40 and 100 bases in length, more preferably between 40 and 70 bases in length. The stem of the hairpin is preferably between 19 and 30 base pairs in length. The stem may contain G-U pairings to stabilise the hairpin structure.

siRNA molecules, longer dsRNA molecules or miRNA molecules may be made recombinantly by transcription of a nucleic acid sequence, preferably contained within a vector. Preferably, the siRNA molecule, longer dsRNA molecule or miRNA molecule comprises a partial sequence of SEQ ID NO: 1, 3, 5, 7, 9, 11, 13, 15 or a variant thereof.

In other embodiments, the suppressor nucleic acid may be an anti-sense suppressor of expression of the SHORT-ROOT (SHR) polypeptide. In using anti-sense sequences to down-regulate gene expression, a nucleotide sequence is placed under the control of a promoter in a "reverse orientation" such that transcription yields RNA which is complementary to normal mRNA transcribed from the "sense" strand of the target gene. See, for example, Rothstein et al, 1987; Smith et al, (1988) Nature 334, 724-726; Zhang et al., (1992) The Plant Cell 4, 1575-1588, English et al., (1996) The Plant Cell 8, 179-188. Antisense technology is also reviewed in Bourque, (1995), Plant Science 105, 125-149, and Flavell (1994) PNAS USA 91, 3490-3496.

An anti-sense suppressor nucleic acid may comprise an anti-sense sequence of at least 10 nucleotides from a nucleotide sequence is a fragment of SEQ ID NO: 1, 3, 5, 7, 9, 11, 13, 15 or a variant thereof.

It may be preferable that there is complete sequence identity in the sequence used for down-regulation of expression of a target sequence, and the target sequence, although total complementarity or similarity of sequence is not essential. One or more nucleotides may differ in the sequence used from the target gene. Thus, a sequence employed in a down-regulation of gene expression in accordance with the present invention may be a wild-type sequence (e.g. gene) selected from those available, or a variant of such a sequence.

The sequence need not include an open reading frame or specify an RNA that would be translatable. It may be preferred for there to be sufficient homology for the respective anti-sense and sense RNA molecules to hybridise. There may be down regulation of gene expression even where there is about 5%, 10%, 15% or 20% or more mismatch between the sequence used and the target gene. Effectively, the homology should be sufficient for the down-regulation of gene expression to take place.

In other embodiments, expression of the SHORT-ROOT (SHR) polypeptide may be reduced in a plant by selective plant breeding methods which employ the SHORT-ROOT (SHR) amino acid or nucleic acid sequence as a molecular marker in order to produce a plant having increased above-ground growth and/or biomass.

A method of producing a plant having increased growth and/or biomass may comprise:
  providing a population of plants,
  determining the amount of expression of an SHR polypeptide in one or more plants in the population, and
  identifying one or more plants in the population with reduced expression of the SHR polypeptide relative to other members of said population.

The identified plants may be further propagated or crossed, for example, with other plants having reduced SHR expression or self-crossed to produce inbred lines. The expression of an SHR polypeptide in populations of progeny plants may be determined and one or more progeny plants with reduced expression of the SHR polypeptide identified.

The expression of an SHR polypeptide in a plant may be determined by any convenient method. In some embodiments, the amount of expression of the SHR polypeptide may be determined at the protein level. A method of producing a plant having increased growth and/or biomass may comprise:
  providing a population of plants,
  determining the amount of SHR polypeptide in one or more plants of said population, and
  identifying one or more plants in the population with reduced amount of an SHR polypeptide relative to other members of said population.

The amount of SHR polypeptide may be determined in one or more cells of the plant, preferably cells from an above-ground portion or tissue of the plant, such as the vasculature and primary and secondary meristems in the shoot, in particular, the cambial zone The amount of SHR polypeptide may be determined using any suitable technique. Conveniently, immunological techniques, such as Western blotting may be employed, using antibodies which bind to the SHR polypeptide and show little or no binding to other antigens in the plant. For example, the amount of an SHR polypeptide in a plant cell may be determined by contacting a sample comprising the plant cell with an antibody or other specific binding member directed against the SHR polypeptide, and determining binding of the SHR polypeptide to the sample. The amount of binding of the specific binding member is indicative of the amount of SHR polypeptide which is expressed in the cell.

In other embodiments, the expression of the SHR polypeptide may be determined at the nucleic acid level. For example, the amount of nucleic acid encoding an SHR polypeptide may be determined. A method of producing a plant having increased above-ground growth and/or biomass may comprise:
  providing a population of plants,
  determining the level or amount of nucleic acid, for example mRNA, encoding the SHR polypeptide in a cell of one or more plants of said population, and,
  identifying one or more plants in the population with reduced amount of an SHR encoding nucleic acid relative to other members of said population.

The level or amount of encoding nucleic acid in a plant cell may be determined for example by detecting the amount of transcribed encoding nucleic acid in the cell. This may be performed using standard techniques such as Northern blotting or RT-PCR.

A suitable cell may be from an above-ground portion or tissue of the plant, such as the vasculature and primary and secondary meristems in the shoot, in particular, the cambial zone.

Alternatively, the presence of sequence variations which affect the expression or activity of an SHR polypeptide may be determined. Another method of producing a plant having increased growth and/or biomass may comprise:
  providing a population of plants,
  determining the presence of one or more sequence variations, for example, polymorphisms, mutations or regions of hypermethylation, in a nucleic acid encoding an SNR polypeptide in a cell in one or more plants of said population,
  wherein said one or more sequence variations which reduce but not abolish the expression or activity of the encoded SHR polypeptide, and
  identifying one or more plants in the population with one or more sequence variations which reduce the expression or activity of an SHR polypeptide relative to other members of said population.

SHR polypeptides and encoding nucleic acid are described in more detail above.

Sequence variations, such as mutations and polymorphisms, which reduce or abolish the expression or activity may include a deletion, insertion or substitution of one or more nucleotides, relative to the wild-type nucleotide sequence, a gene amplification or an increase or decrease in methylation, for example hypermethylation. The one or more sequence variations may be in a coding or non-coding region of the nucleic acid sequence. Mutations in the coding region of the gene encoding the component may prevent the translation of full-length active protein i.e. truncating mutations, or allow the translation of full-length but inactive or impaired function protein i.e. mis-sense mutations. Mutations or epigenetic changes, such as methylation, in non-coding regions of the gene encoding the component, for example, in a regulatory element, may prevent transcription of the gene. A nucleic acid comprising one or more sequence variations may encode a variant polypeptide which has reduced or abolished activity or may encode a wild-type polypeptide which has little or no expression within the cell, for example through the altered activity of a regulatory element. A nucleic acid comprising one or more sequence variations may have one, two, three, four or more mutations or polymorphisms relative to the control sequences.

The presence of one or more sequence variations in a nucleic acid may be determined by detecting the presence of the variant nucleic acid sequence in one or more plant cells or by detecting the presence of the variant polypeptide which is encoded by the nucleic acid sequence. Preferred nucleic acid sequence variation detection techniques include ARMS™-allele specific amplification, OLA, ALEX™, COPS, Taqman, Molecular Beacons, RFLP, and restriction site based PCR and FRET techniques.

Numerous suitable methods for determining the amount of a nucleic acid encoding an SHR polypeptide, or the presence or absence of sequence variation in a nucleic acid encoding an SHR polypeptide, in a plant cell, are available in the art (see for example (see for example Molecular Cloning: a Laboratory Manual: 3rd edition, Sambrook & Russell (2001) Cold Spring Harbor Laboratory Press NY; Current Protocols in Molecular Biology, Ausubel et al. eds. John Wiley & Sons (1992); DNA Cloning, The Practical Approach Series (1995), series eds. D. Rickwood and B. D. Hames, IRL Press, Oxford, UK and PCR Protocols: A Guide to Methods and Applications (Innis, et al. 1990. Academic Press, San Diego, Calif.)). Many current methods for the detection of sequence variation are reviewed by Nollau et al., Clin. Chem. 43, 1114-1120, 1997; and in standard textbooks, for example "Laboratory Protocols for Mutation Detection", Ed. by U. Landegren, Oxford University Press, 1996 and "PCR", $2^{nd}$ Edition by Newton & Graham, BIOS Scientific Publishers Limited, 1997.

Preferred polypeptide sequence variation techniques include immunoassays, which are well known in the art e.g. A Practical Guide to ELISA by D M Kemeny, Pergamon Press 1991; Principles and Practice of Immunoassay, $2^{nd}$ edition, C P Price & D J Newman, 1997, published by Stockton Press in USA & Canada and by Macmillan Reference in the United Kingdom.

In some embodiments, nucleic acid or an amplified region thereof may be sequenced to identify or determine the presence of polymorphism or mutation therein. A polymorphism or mutation may be identified by comparing the sequence obtained with the known sequence of SHR, for example as set out in sequence databases. Alternatively, it can be compared to the sequence of the corresponding nucleic acid from control cells. In particular, the presence of one or more polymorphisms or mutations that cause reduction but not total abrogation of function may be determined. Sequencing may be performed using any one of a range of standard techniques. Sequencing of an amplified product may, for example, involve precipitation with isopropanol, resuspension and sequencing using a TaqFS+ Dye terminator sequencing kit (e.g. from GE Healthcare UK Ltd UK). Extension products may be electrophoresed on an ABI 377 DNA sequencer and data analysed using Sequence Navigator software.

A progeny plant identified as having reduced SHR expression may be tested for increased biomass, growth and growth rate relative to controls.

A method of producing a plant having increased growth and/or biomass may comprise:
  crossing a first and a second plant to produce a population of progeny plants;
  determining the expression of an Short Root (SHR) polypeptide in the progeny plants in the population, and
  identifying a progeny plant in the population in which expression of the SHR polypeptide is reduced relative to controls but not abolished.

A progeny plant in which expression of the SHR polypeptide is reduced, but not abolished (i.e. expression is not completely eliminated) relative to controls (e.g. other members of the population) may display increased primary and/or secondary growth relative to the controls or increased biomass accumulation. A woody plant may show increased wood density.

The identified progeny plant may be further propagated or crossed, for example with the first or second plant (i.e. back-crossing) or self-crossed to produce inbred lines.

The identified progeny plant may be tested for increased biomass, growth and growth rate relative to controls.

Other aspects of the invention provide the use of an SHORT-ROOT (SHR) polypeptide or encoding nucleic acid as described herein as a marker for the selective breeding of a plant which has increased biomass or growth in its above ground portion, relative to control plants, and a method of selective breeding of a plant which has increased biomass or growth in its above ground portion, relative to control plants, which employs the SHORT-ROOT (SHR) amino acid or encoding nucleic acid sequence.

In some embodiments, plants having reduced expression of the SHORT-ROOT (SHR) polypeptide may be produced by random mutagenesis, followed by screening of mutants for reduced SHR expression. Suitable techniques are well known in the art and include Targeting Induced Local Lesions IN Genomes (TILLING). TILLING is a high-throughput screening technique that results in the systematic identification of non-GMO-derived mutations in specific target genes (Comai and Henikoff, The Plant Journal (2006) 45, 684-694).

A method of producing a plant having increased growth and/or biomass may comprise:
  exposing a population of plants to a mutagen,
  determining the expression of an SHR polypeptide or nucleic acid in one or more plants in said population, and
  identifying a plant with reduced expression of the SHR polypeptide relative to other members of said population.

Suitable mutagens include ethane methyl sulfonate (EMS).

Methods for determining the expression of SHR polypeptide or nucleic acid in plants is described in more detail above.

The identified plant may be further tested for increased above ground biomass, growth and/or growth rate relative to controls.

A plant identified as having reduced expression of the SHR polypeptide relative to controls (e.g. other members of the population) may display increased primary and/or secondary growth in its above ground portion relative to the controls or increased biomass accumulation. A woody plant may show increased wood density.

A plant produced or identified as described above may be sexually or asexually propagated or grown to produce off-spring or descendants. Off-spring or descendants of the plant regenerated from the one or more cells may be sexually or asexually propagated or grown. The plant or its off-spring or descendents may be crossed with other plants or with itself.

Another aspect of the invention provides a plant which is produced by a method described herein, wherein said plant shows increased growth and/or biomass relative to control plants.

Also provided is any part or propagule of such a plant, for example seeds, selfed or hybrid progeny and descendants.

A plant according to the present invention may be one which does not breed true in one or more properties. Plant varieties may be excluded, particularly registrable plant varieties according to Plant Breeders Rights.

In addition to a plant produced by a method described herein, the invention encompasses any clone of such a plant, seed, selfed or hybrid progeny and descendants, and any part or propagule of any of these, such as cuttings and seed, which may be used in reproduction or propagation, sexual or asexual. Also encompassed by the invention is a plant which is a sexually or asexually propagated off-spring, clone or descendant of such a plant, or any part or propagule of said plant, off-spring, clone or descendant.

In other embodiments, expression of the SHORT-ROOT (SHR) polypeptide may be increased in the cells relative to control plants in order to increase the above-ground growth and/or biomass of a plant. Expression of the SHORT-ROOT (SHR) polypeptide may, for example, be increased within cells of said plant by up to 2-fold, 5-fold, 10-fold, or 100-fold of the expression within cells of control plants.

Expression of the SHORT-ROOT (SHR) polypeptide may be increased within cells of said plant by any convenient method. For example, expression in the cells of said plant may be increased by expressing a heterologous nucleic acid encoding the SHORT-ROOT (SHR) polypeptide within cells of said plant.

SHORT-ROOT (SHR) polypeptides are described in more detail above. A nucleic acid encoding a SHR polypeptide may comprise or consist of the nucleotide sequence of SEQ ID NO: 1, 3, 5, 7, 9, 11, 13 or 15 or may be a variant or fragment of any one of these sequences which retains SHR activity.

A variant sequence may be a mutant, homologue, or allele of SEQ ID NO: 1, 3, 5, 7, 9, 11, 13 or 15 may differ from one of these sequences by one or more of addition, insertion, deletion or substitution of one or more nucleotides in the nucleic acid, leading to the addition, insertion, deletion or substitution of one or more amino acids in the encoded polypeptide. Of course, changes to the nucleic acid that make no difference to the encoded amino acid sequence are included. A nucleic acid encoding a SHR polypeptide, which has a nucleotide sequence which is a variant of SEQ ID NO: 1, 3, 5, 7, 9, 11, 13 or 15 sequence may comprise a sequence having at least 30% sequence identity with the nucleic acid sequence of SEQ ID NO: 1, 3, 5, 7, 9, 11, 13 or 15, for example, preferably greater than 40%, greater than 50%, greater than 60%, greater than 65%, greater than 70%, greater than 80%, greater than 90% or greater than 95%. Sequence identity is described above.

A fragment or variant may comprise a sequence which encodes a functional SHR polypeptide i.e. a polypeptide which retains one or more functional characteristics of the polypeptide encoded by the wild-type SHR gene, for example, the ability to stimulate growth in a plant.

In other embodiments, a nucleic acid encoding a SHR polypeptide, which has a nucleotide sequence which is a variant of SEQ ID NO: 1, 3, 5, 7, 9, 11, 13 or 15 sequence may selectively hybridise under stringent conditions with this nucleic acid sequence or the complement thereof.

Stringent conditions include, e.g. for hybridization of sequences that are about 80-90% identical, hybridization overnight at 42° C. in 0.25M $Na_2HPO_4$, pH 7.2, 6.5% SDS, 10% dextran sulfate and a final wash at 55° C. in 0.1×SSC, 0.1% SDS. For detection of sequences that are greater than about 90% identical, suitable conditions include hybridization overnight at 65° C. in 0.25M $Na_2HPO_4$, pH 7.2, 6.5% SDS, 10% dextran sulfate and a final wash at 60° C. in 0.1×SSC, 0.1% SDS.

An alternative, which may be particularly appropriate with plant nucleic acid preparations, is a solution of 5×SSPE (final 0.9 M NaCl, 0.05M sodium phosphate, 0.005M EDTA pH 7.7), 5×Denhardt's solution, 0.5% SDS, at 50° C. or 65° C. overnight. Washes may be performed in 0.2×SSC/0.1% SDS at 65° C. or at 50-60° C. in 1×SSC/0.1% SDS, as required.

A nucleic acid encoding a Short Root (SHR) polypeptide or a nucleic acid which suppresses the expression of a Short Root (SHR) polypeptide (i.e. a suppressor RNA molecule) may be operably linked to a regulatory sequence, such as a promoter, for example a constitutive, inducible, tissue-specific or developmental specific promoter.

A regulatory sequence operably linked to a SHR nucleic acid sequence is preferably heterologous or foreign to the SHR nucleic acid sequence (e.g. from a different species, class or type of organism). Preferably, the regulatory sequence is a plant specific regulatory sequence to provide for efficient expression within a plant cell. A plant specific regulatory sequence or element preferentially directs the expression (i.e. transcription) of a nucleic acid within a plant cell relative to other cell types. For example, expression from such a sequence may be reduced or abolished in non-plant cells, such as bacterial or mammalian cells.

Many suitable regulatory sequences are known in the art and may be used in accordance with the invention. Examples of suitable regulatory sequences may be derived from a plant virus, for example the Cauliflower Mosaic Virus 35S (CaMV 35S) gene promoter that is expressed at a high level in virtually all plant tissues (Benfey et al, (1990) EMBO J. 9: 1677-1684). Leaf specific promoters may also be used (see for example Lagrange et al Plant Cell. 1997 9 (8): 1469-1479). Other suitable constitutive regulatory elements include the cauliflower mosaic virus 19S promoter; the Figwort mosaic virus promoter; and the nopaline synthase (nos) gene promoter (Singer et al., Plant Mol. Biol. 14:433 (1990); An, Plant Physiol. 81:86 (1986)).

In some embodiments, an inducible promoter such as the alcohol inducible alc gene-expression system (Roslan et al., Plant Journal; 2001 October; 28(2):225-35) may be employed.

Heterologous nucleic acid may be contained on a nucleic acid construct or vector. The construct or vector is preferably suitable for transformation into and/or expression within a plant cell.

A vector is, inter alia, any plasmid, cosmid, phage or *Agrobacterium* binary vector in double or single stranded linear or circular form, which may or may not be self transmissible or mobilizable, and which can transform prokaryotic or eukaryotic host, in particular a plant host, either by integration into the cellular genome or exist extrachromasomally (e.g. autonomous replicating plasmid with an origin of replication).

Specifically included are shuttle vectors by which is meant a DNA vehicle capable, naturally or by design, of replication in two different organisms, which may be selected from *actinomyces* and related species, bacteria and eukaryotic (e.g. higher plant, mammalia, yeast or fungal) cells.

A construct or vector comprising nucleic acid as described above need not include a promoter or other regulatory sequence, particularly if the vector is to be used to introduce the nucleic acid into cells for recombination into the genome.

Constructs and vectors may further comprise selectable genetic markers consisting of genes that confer selectable phenotypes such as resistance to antibiotics such as kanamycin, hygromycin, phosphinotricin, chlorsulfuron, methotrexate, gentamycin, spectinomycin, imidazolinones, glyphosate and d-amino acids.

Those skilled in the art are well able to construct vectors and design protocols for recombinant gene expression, in particular in a plant cell. Suitable vectors can be chosen or constructed, containing appropriate regulatory sequences, including promoter sequences, terminator fragments, polyadenylation sequences, enhancer sequences, marker genes and other sequences as appropriate. For further details see, for example, *Molecular Cloning: a Laboratory Manual:* 3rd edition, Sambrook & Russell, 2001, Cold Spring Harbor Laboratory Press.

Those skilled in the art can construct vectors and design protocols for recombinant gene expression, for example in a microbial or plant cell. Suitable vectors can be chosen or constructed, containing appropriate regulatory sequences, including promoter sequences, terminator fragments, polyadenylation sequences, enhancer sequences, marker genes and other sequences as appropriate. For further details see, for example, *Molecular Cloning: a Laboratory Manual:* 3rd edition, Sambrook et al, 2001, Cold Spring Harbor Laboratory Press and *Protocols in Molecular Biology*, Second Edition, Ausubel et al. eds. John Wiley & Sons, 1992. Specific procedures and vectors previously used with wide success upon plants are described by Bevan, Nucl. Acids Res. (1984) 12, 8711-8721), and Guerineau and Mullineaux, (1993) Plant transformation and expression vectors. In: Plant Molecular Biology Labfax (Croy R R D ed) Oxford, BIOS Scientific Publishers, pp 121-148.

When introducing a chosen gene construct into a cell, certain considerations must be taken into account, well known to those skilled in the art. The nucleic acid to be inserted should be assembled within a construct that contains effective regulatory elements that will drive transcription. There must be available a method of transporting the construct into the cell. Once the construct is within the cell membrane, integration into the endogenous chromosomal material either will or will not occur. Finally, the target cell type is preferably such that cells can be regenerated into whole plants.

Techniques well known to those skilled in the art may be used to introduce nucleic acid constructs and vectors into plant cells to produce transgenic plants with the properties described herein.

*Agrobacterium* transformation is one method widely used by those skilled in the art to transform woody plant species, in particular hardwood species such as poplar. Production of stable, fertile transgenic plants is now routine in the art: (Toriyama, et al. (1988) *Bio/Technology* 6, 1072-1074; Zhang, et al. (1988) *Plant Cell Rep.* 7, 379-384; Zhang, et al. (1988) *Theor Appl Genet.* 76, 835-840; Shimamoto, et al. (1989) *Nature* 338, 274-276; Datta, et al. (1990) *Bio/Technology* 8, 736-740; Christou, et al. (1991) *Bio/Technology* 9, 957-962; Peng, et al. (1991) International Rice Research Institute, Manila, Philippines 563-574; Cao, et al. (1992) *Plant Cell Rep.* 11, 585-591; Li, et al. (1993) *Plant Cell Rep.* 12, 250-255; Rathore, et al. (1993) *Plant Molecular Biology* 21, 871-884; Fromm, et al. (1990) *Bio/Technology* 8, 833-839; Gordon-Kamm, et al. (1990) *Plant Cell* 2, 603-618; D'Halluin, et al. (1992) *Plant Cell* 4, 1495-1505; Walters, et al. (1992) *Plant Molecular Biology* 18, 189-200; Koziel, et al. (1993) *Biotechnology* 11, 194-200; Vasil, I. K. (1994) *Plant Molecular Biology* 25, 925-937; Weeks, et al. (1993) *Plant Physiology* 102, 1077-1084; Somers, et al. (1992) *Bio/Technology* 10, 1589-1594; WO92/14828; Nilsson, O. et al (1992) *Transgenic Research* 1, 209-220).

Other methods, such as microprojectile or particle bombardment (U.S. Pat. No. 5,100,792, EP-A-444882, EP-A-434616), electroporation (EP 290395, WO 8706614), microinjection (WO 92/09696, WO 94/00583, EP 331083, EP 175966, Green et al. (1987) *Plant Tissue and Cell Culture*, Academic Press), direct DNA uptake (DE 4005152, WO 9012096, U.S. Pat. No. 4,684,611), liposome mediated DNA uptake (e.g. Freeman et al. *Plant Cell Physiol.* 29: 1353 (1984)), or the vortexing method (e.g. Kindle, *PNAS U.S.A.* 87: 1228 (1990d)) may be preferred where *Agrobacterium* transformation is inefficient or ineffective, for example in some gymnosperm species.

Physical methods for the transformation of plant cells are reviewed in Oard, 1991, *Biotech. Adv.* 9: 1-11.

Alternatively, a combination of different techniques may be employed to enhance the efficiency of the transformation process, e.g. bombardment with *Agrobacterium* coated microparticles (EP-A-486234) or microprojectile bombardment to induce wounding followed by co-cultivation with *Agrobacterium* (EP-A-486233).

Following transformation, a plant may be regenerated, e.g. from single cells, callus tissue or leaf discs, as is standard in the art. Almost any plant can be entirely regenerated from cells, tissues and organs of the plant. Available techniques are reviewed in Vasil et al., *Cell Culture and Somatic Cell Genetics of Plants, Vol I, II and III, Laboratory Procedures and Their Applications*, Academic Press, 1984, and Weissbach and Weissbach, *Methods for Plant Molecular Biology*, Academic Press, 1989.

The particular choice of a transformation technology will be determined by its efficiency to transform certain plant species as well as the experience and preference of the person practising the invention with a particular methodology of choice. It will be apparent to the skilled person that the particular choice of a transformation system to introduce nucleic acid into plant cells is not essential to or a limitation of the invention, nor is the choice of technique for plant regeneration.

Another aspect of the invention provides a method of producing a plant having increased growth and/or biomass comprising:

incorporating a heterologous nucleic acid which alters the expression of a SHORT-ROOT (SHR) polypeptide into a plant cell by means of transformation, and;

regenerating the plant from one or more transformed cells.

In some embodiments described above, the heterologous nucleic acid may increase the expression of a SHORT-ROOT (SHR) polypeptide. For example the heterologous nucleic acid may encode a SHORT-ROOT (SHR) polypeptide. The growth and or biomass of the above ground portions of the plant may be increased by the increase in SHORT-ROOT (SHR) polypeptide expression.

In other embodiments described above, the heterologous nucleic acid may reduce but not abolish the expression of a SHORT-ROOT (SHR) polypeptide. For example the heterologous nucleic acid may encode or transcribe a nucleic acid which suppresses the expression of SHORT-ROOT (SHR) polypeptide, for example an RNAi molecule.

A plant produced by such methods may show increased growth and/or biomass relative to control plants. For example, the above ground portions of the plant may show increased growth and/or biomass relative to controls.

Preferably, the nucleic acid recombines with the cell genome nucleic acid, such that it is stably incorporated therein.

The SHR polypeptide, the encoding nucleic acid, and/or the vector comprising the nucleic acid are described in more detail above and may be heterologous (e.g. exogenous or foreign) to the cell transformed therewith.

The regenerated plant shows increased growth and/or biomass relative to controls. For example, the above ground portions of the plant may show increased growth and/or biomass. A regenerated woody plant may show increased wood density. A plant regenerated from a plant cell may be sexually or asexually propagated or grown to produce off-spring or descendants. Off-spring or descendants of the plant regenerated from the one or more cells may be sexually or asexually propagated or grown Another aspect of the invention provides a plant which is produced by a method described herein, wherein said plant shows increased growth and/or biomass, for example increased above-ground growth and/or biomass, relative to control plants.

For example, plant may be provided which comprises a heterologous nucleic acid encoding an SHORT-ROOT (SHR) polypeptide or a suppressor of the expression of SHORT-ROOT (SHR) polypeptide within one or more of its cells.

Also provided is any part or propagule of such a plant, for example seeds, selfed or hybrid progeny and descendants.

A plant may be one which does not breed true in one or more properties. Plant varieties may be excluded, particularly registrable plant varieties according to Plant Breeders Rights. It is noted that a plant need not be considered a "plant variety" simply because it contains stably within its genome a transgene, introduced into a cell of the plant or an ancestor thereof.

In addition to a plant, any clone of such a plant, seed, selfed or hybrid progeny and descendants, and any part or propagule of any of these, such as cuttings and seed, may be useful in reproduction or propagation, sexual or asexual. A plant which is a sexually or asexually propagated off-spring, clone or descendant of such a plant, or any part or propagule of said plant, off-spring, clone or descendant may also be useful.

A plant may have increased or decreased expression of SHR polypeptide, relative to the wild-type (i.e. 'unmodified') plant. SHR expression may be increased, for example, by expressing a nucleic acid encoding an SHR polypeptide in the cells of the plant or reduced by expressing a nucleic acid which causes anti-sense, sense or RNAi down-regulation of SHR in the cells of the plant, as described above.

Control experiments may be performed as appropriate in the methods described herein. The performance of suitable controls is well within the competence and ability of a skilled person in the field.

Examples of suitable plants for use in accordance with any aspect of the invention described herein include monocotyledons, dicotelydons, gymnosperms and algae, ferns and mosses. Of particular interest are transgenic higher plants, especially agricultural crops, for example cereals, and flowers, which have been engineered to carry a heterologous nucleic acid as described above, including tobacco, cucurbits, carrot, vegetable *brassica*, melons, capsicums, grape vines, lettuce, strawberry, oilseed *brassica*, sugar beet, wheat, barley, maize, rice, soyabeans, peas, sorghum, sunflower, tomato, potato, pepper, chrysanthemum, carnation, linseed, hemp and rye.

Examples of SHR protein sequences from *Arabidopsis*, Poplar, Rice, Barley and *Medicago* are set out herein.

In some preferred embodiments, the plant is a perennial plant, for example a woody perennial plant. A woody perennial plant is a plant which has a life cycle which takes longer than 2 years and involves a long juvenile period in which only vegetative growth occurs. This is contrasted with an annual or herbaceous plant such as *Arabidopsis thaliana* or *Lycopersicon esculentum* (tomato), which have a life cycle which is completed in one year.

A woody perennial plant has hard, lignified tissues and forms a bush or tree. Preferred perennial plants are trees (i.e. plants of tree forming species). A woody perennial plant may be a gymnosperm (non-flowering plant) or an angiosperm (flowering plant). Angiosperms are divided into two broad classes and a perennial plant may be a monocotyledonous or dicotyledonous angiosperm.

Examples of woody perennial plants include conifers such as cypress, Douglas fir, fir, sequoia, hemlock, cedar, juniper, larch, pine, redwood, spruce and yew; hardwoods such as acacia, eucalyptus, hornbeam, beech, mahogany, walnut, oak, ash, willow, hickory, birch, chestnut, poplar, alder, maple and sycamore; fruit bearing plants such as apple, plum, pear, banana, orange, kiwi, lemon, cherry, grapevine and fig; and other commercially significant plants, such as cotton, bamboo and rubber.

Other aspects of the invention relate to the use of the SHR promoter to screen for compounds which alter (i.e. increase or reduce) the expression of SHR polypeptide in a plant.

A method of screening for a compound which increases the above-ground growth and/or biomass of a plant comprising;
providing a nucleic acid construct comprising an SHR promoter operably linked to a reporter gene, in an expression system in which the reporter is expressed,
contacting the construct with a test compound, and determining the expression of the reporter,
wherein an increase or decrease in the expression of the reporter in the presence relative to the absence of test compound is indicative that the compound increases the above-ground growth and/or biomass of a plant.

A SHR promoter may have the sequence of SEQ ID NO: 22 or 23 or may be a variant or fragment thereof. Variants and fragments of reference SHR sequences, such as SEQ ID NO: 22 and 23, are described above.

Suitable reporter genes are well known in the art and include genes encoding fluorescent proteins such as GFP.

The SHR promoter may also be useful in driving expression of a heterologous gene in the wood-forming tissues of a woody perennial plant. Wood-forming tissues include the vasculature and primary and secondary meristems in the shoot, including the cambial zone.

A method of producing a plant may comprise:
incorporating a nucleic acid construct or vector comprising an SHORT-ROOT (SHR) promoter operably linked to a heterologous gene into a plant cell by means of transformation, and;
regenerating the plant from one or more transformed cells.

Preferably the plant is a woody perennial plant and the SHORT-ROOT (SHR) promoter drives expression of the heterologous gene in the wood forming tissue of the woody perennial plant.

Suitable heterologous sequences may include sequences encoding polypeptides that alter the growth or composition of cell, tissues, and/or organs of the transformed plant, in particular growth promoting genes and genes which improve wood quality.

The regenerated plant may be crossed or propagated as described above.

Other aspects of the invention provide a nucleic acid construct or vector comprising a SHORT-ROOT (SHR) promoter operably linked to a heterelogous gene, the use of such a nucleic acid construct or vector
to specifically express the heterologous gene in the wood-forming tissues of a woody perennial plant, and a method of expressing a heterologous gene in the wood forming-tissues of a woody perennial plant by introducing such a construct or vector into the woody perennial plant.

Various further aspects and embodiments of the present invention will be apparent to those skilled in the art in view of the present disclosure. All documents mentioned in this specification are incorporated herein by reference in their entirety. "and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

The Sequence Listing is submitted as an ASCII text file (created on Jul. 2, 2010, ~101 kB), which is incorporated by reference herein.

Certain aspects and embodiments of the invention will now be illustrated by way of example and with reference to the figures described below.

FIG. 1 shows an unrooted cladogram of Poplar and *Arabidopsis* sequences with similarity to AtSHR. The phylogenetic analysis was performed with full length predicted amino acid sequences from Poplar and *Arabidopsis* members of the SHR branch of the GRAS family. ClustalW was used to align the protein sequences. The Phylip format was used for tree output, using 1000 bootstrap replicates. The cladogram was visualised using TreeViewX (version 0.5.0).

FIG. 2 shows a nucleotide sequence alignment between the predicted coding sequences of AtSHR and the three Poplar SHR-like proteins, PtSHR1, PtSHR2A and PtSHR2B.

FIG. 3 shows a comparison of the deduced amino acid sequence of PtSHR1, PtSHR2A, PtSHR2B and AtSHR. Identical, similar and conserved amino acids are shown in black and grey backgrounds, respectively. Amino acid motifs conserved across members of the GRAS family are shown.

FIG. 4 shows differential growth of WT T89 and PtSHR1 RNAi Line 2B trees. Trees after a growth period of 52 days in the glasshouse and two of the same trees as initial plantlets in tissue culture (inset).

FIG. 5 shows girth measurements of Poplar stems after 52 days growth in the glasshouse. Independent transformation events of Poplar PtSHR1 RNAi lines (2A, 2B and 4A) compared to WT T89. Results are presented as means plus and minus 1 SD. Means are the average width from 10 internodes from 9 trees for each of the RNAi and WT T89 lines, beginning at an internode 200 mm above the soil.

FIG. 6 shows transverse sections of WT T89 and PtSHR1 RNAi Line 2B. Sections were taken from the middle of internodes 500 mm above the soil and are stained with toluidine blue. Double headed arrows indicate xylem (wood cells).

FIG. 7 shows accumulated biomass of Poplar stems after 52 days growth in the glasshouse. Independent transformation events of Poplar PtSHR1 RNAi lines (2A, 2B and 4A) compared to WT T89. Results are presented as means plus and minus 1 SD. Means, n=9, are the average total fresh mass in grams of stems plus leaves from 200 mm above the soil.

FIG. 8 shows average internode length of Poplar stems after 52 days growth in the glasshouse. Independent transformation events of Poplar PtSHR1 RNAi lines (2A, 2B and 4A) compared to WT T89. Results are presented as means plus and minus 1 SD. Means, n=9, are the average lengths of 15 fully expanded internodes beginning at 200 mm above the soil.

FIG. 9 shows average number of leaves (nodes) in Poplar stems after 52 days growth in the glasshouse. Poplar PtSHR1 RNAi line 2B compared to WT T89. Results are presented as means plus and minus 1 SD. Means, n=9, are the average number of leaves produced from 200 mm above the soil to the youngest leaf of at least 40 mm in length.

FIG. 10 shows a comparison of the lengths and widths of tracheids from the middle of fully expanded internodes of independent transformation events of Poplar PtSHR1 RNAi lines (2A and 2B) compared to WT T89. Results are presented as means plus and minus 1 SD. Means, n=30, are the average widths and lengths (arbitrary units) of tracheids. A & C and B & D represent measurements from sections taken from separate internodes of approximately the same length.

FIG. 11 shows average leaf area and fresh weight of fully expanded leaves from Poplar stems after 52 days growth in the glasshouse. Poplar PtSHR1 RNAi lines (2A, 2B and 4A) compared to WT T89. Results are presented as means plus and minus 1 SD. Means are the average area and weight of 15 fully expanded leaves from 200 mm above the soil of 9 separate trees for each of the lines 2A, 2B, 4A and WT T89.

FIG. 12 shows a comparison of PtSHR1 transcript levels in various organs of Poplar plants. Data is presented as relative expression log 2 scale with error bars indicating 1 SD. Data represents levels of PtSHR1 transcripts relative to a pooled sample of all tissues (eg apex vs pool, leaf vs pool). Apex=shoot apex; PrimRoot=primary root (tissue culture grown); SecRoot=secondary (lateral) root (tissue culture grown).

FIG. 13 shows germination and early growth of AtSHR-suppressed *Arabidopsis* RNAi and WT control plants. A. Germination of seeds of transgenic lines 4, 6 and 11 and WT seeds. B. WT and Line 11 seeds after 18 hours at 23° C. C. WT and Line 11 seeds after 40 hours at 23° C. D. WT and Line 11 seedlings after 5.5 days at 23° C. E. Etiolated WT and Line 11 seeds after 5.5 days at 23° C. F. Average cotyledon size of light-grown WT and Line 11 seedlings after 5.5 days at 23° C. G. Average hypocotyl length of etiolated seedlings after 5.5 days at 23° C. H. Average root lengths of WT, shr and transgenic seedlings after 5.5 days at 23° C. Plates for plants grown in the light (A, B, C, D, F and H) contained 1% sucrose. Etiolated seedlings were grown on plates without sucrose. Results for A are presented as percentage germination of samples of 140 seeds over time. All experiments were conducted three times with similar results. The presented results are representative of all three experiments. WT and RNAi seeds for the experiments were grown under the same conditions, at the same time. After harvesting these seeds they were left to fully mature for at least 2 months prior to conducting the germination and growth experiments. Results for F, G and H are presented as the means plus and minus 1 SD.

FIG. 14 shows a comparison of growth in *Arabidopsis* RNAi transgenic and WT control plants. A. Line 11 plants at stage 1.06 (Boyes et al., The Plant Cell, Vol. 13, 1499-1510, 2001) at 15 DAG. B. WT plants at the same stage of development (at 18 DAG). C. Area of fully expanded true leaves 1 and 2. D. Line 11 plants at 18 DAG (compare B and D). E. Total leaf area at 18 DAG in the RNAi lines and in WT controls. F. Radial longitudinal sections through the apexes of WT control and Line 11 transgenic plants at day 18. Circles in A and B highlight the $5^{th}$ true leaf. The dotted lines in F represent the diameter of the WT apical dome.

Figure 15:
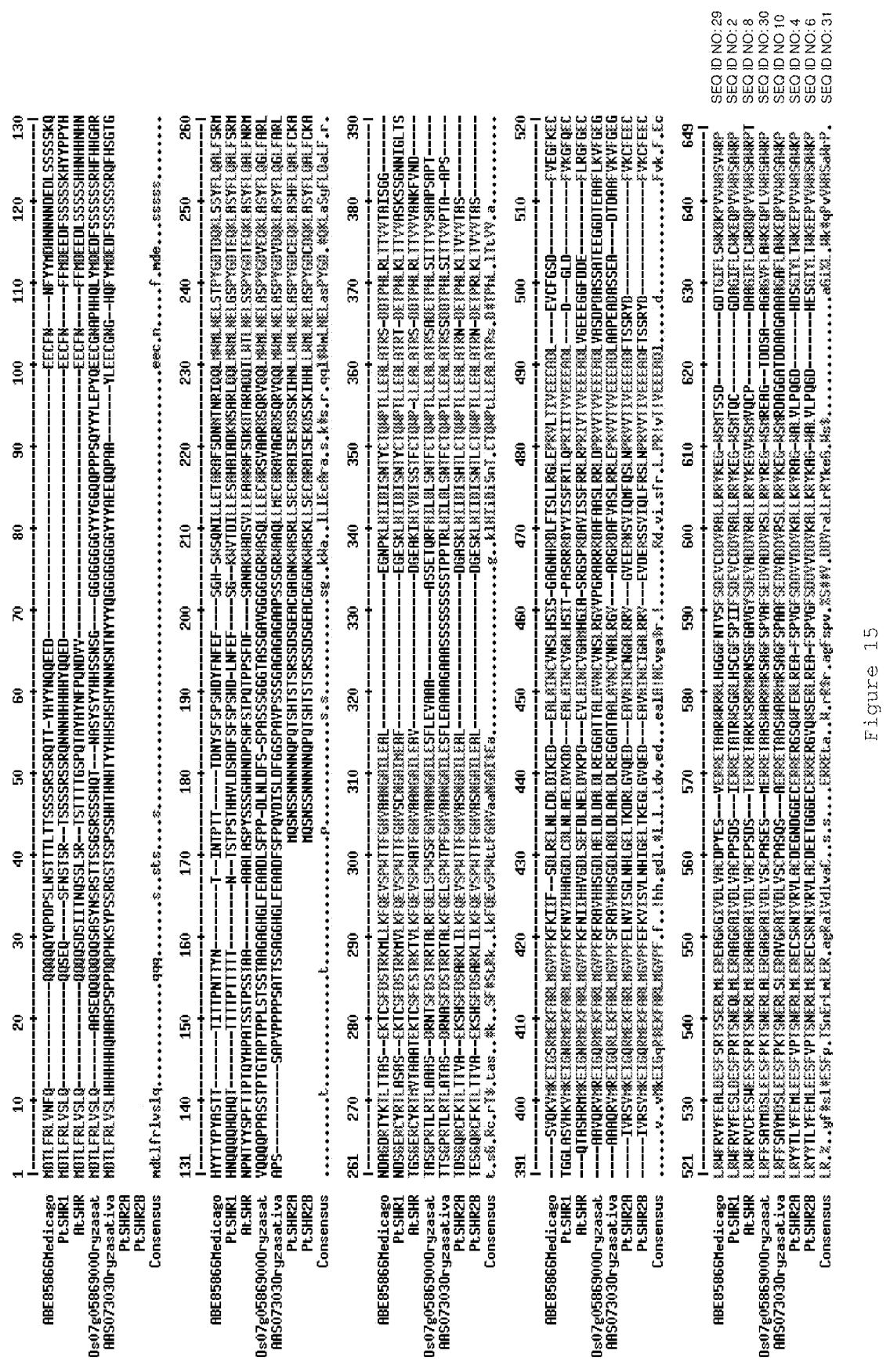

FIG. 15 shows a multiple amino acid alignment of PtSHR genes, AtSHR and Rice and Medicago predicted sequences.

EXPERIMENTS

Poplar Transformation

Figure 1:
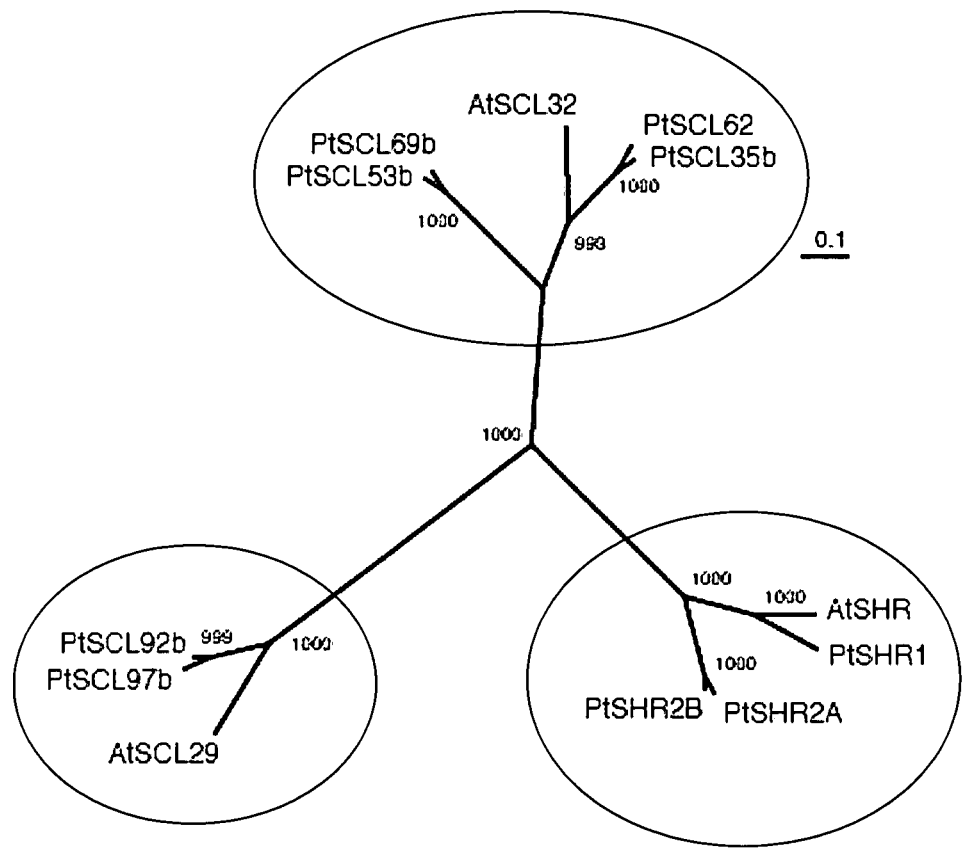

The CaMV 35S: Inverted repeat DNA construct for PtSHR1 was transformed into the pK7GWIWG2(I) binary vector (Karimi et al., Trends Plant Sci. 2002 May; 7(5):193-195) and subsequently transferred to *Agrobacterium tumefaciens* and used to transform hybrid aspen (*Populus tremula× Populus tremuloides*, clone T89) stem segments as described previously (Nilsson et al., 1992 Transgenic Research 1:209-220). Kanamycin resistant transformants were regenerated as described previously (Nilsson et al. supra). The primers used for cloning the PtSHR1 sequence used for the inverted repeat construct were 5'-AGAAAGCTGGGTAACCACCACCAT-CATCACTATC-3' (SEQ ID NO: 32; contains an ATTB2 site) and 5'-AAAAGCAGGCTGCTTTCACCTTCAAAT-GCTTCC-3' (SEQ ID NO: 33; contains an ATTB1 site). The template used for the PCR amplification of the sequence was EST clone UB21CPG06. Cloning into the binary vector was carried out according to the manufacturers recommended protocol (Gateway, Invitrogen, USA). The primer sequences used in the RT-PCR analysis of remnant transcript levels in the transgenic lines were: 5'-CATCACCTGACCTTCACTCC-3' (SEQ ID NO: 34) and 5'-GTTCGGATTGTTGTTGGAGAC-3' (SEQ ID NO: 35). Primers used for determining transcript levels of close homologs of PtSHR1 (PtSHR2A and PtSHR2B) in PtSHR1 RNAi—suppressed lines were 5'-AGCAACAACAACAACAATCAG-3' (SEQ ID NO: 36) and 5'-GCACACTCACTAAGAAGCC-3' (SEQ ID NO: 37). The analysis showed no down regulation of the transcript levels of these two genes.

Twenty four independent lines were generated. Such a group of transgenic trees produced using the short root construct is hereafter called "construction group". Each transgenic line within the construction group was a different transformation event and therefore most probably had the recombinant DNA inserted into different locations in the plant genome. This may make the different lines within one construction group partly different. For example, it is known that different transformation events will produce plants with different levels of gene down-regulation when using RNAi constructs of the type used here.

Poplar Plant Growth

After initiation and establishment of rooting in tissue culture, transgenic Poplar lines were grown together with their wild type control (WT T89) trees, in a greenhouse under a photoperiod of 18 h and a temperature of 22° C./15° C. (day/night). The humidity was RH 70%. The plants were fertilized weekly using the fertiliser "Weibulls Rika S NPK 7-1-5" diluted 1 to 100 (final concentrations NO3, 55 g/l; NH4, 29 g/l; P, 12 g/l; K, 56 g/l; Mg 7.2 g/l; S, 7.2 g/l; B, 0.18 g/l; Cu, 0.02 g/l; Fe, 0.84 g/l; Mn, 0.42 g/l; Mo, 0.03 g/l; Zn, 0.13 g/L). The plants were grown for 7-9 weeks before harvest. During this time their positions within the glasshouse were altered every 2-3 days and their heights and diameters were measured as described in the results. A number of wild type trees (typically 8-25 trees) and a number of transgenic trees comprising the construction group were grown in parallel in the greenhouse under the same above conditions. All comparisons between the wild type trees and the construction group are made within each growth group.

Poplar Growth Measurements

Under the above defined growth conditions, Poplar plants exhibited an exponential growth pattern (plant height) up to an approximate height of 80 cm or a maximum of up to day 40 in the greenhouse. Height measurements were taken at the times stipulated in the results. Under the above defined growth conditions, stem width exhibited a comparatively linear increase over time.

A height growth rate measure (here named "Maximum height growth rate") was defined as the slope of a linear function fitted over four consecutive height data points. A height growth rate value was calculated for data point 1-4, data point 2-5 etc. in a step-wise manner, se FIG. 4 for an example. A maximum growth rate defined as the maximum value, produced from step-wise linear regression analysis, for each plant was computed. The primary data for high Maximum height growth rate values from individual transformants in a construction group were checked so they were not based on bad values.

Immunocytochemistry and Confocal Laser Scanning Microscopy

Tissues were prepared as butyl-methylmethacrylate resin-embedded, semithin sectioned material. The resin-embedded material was prefixed with 100 µM m-male-imidobenzoyl N-hydroxysuccinimide ester (Sigma) in 25 mM Pipes buffer (Sigma), pH 6.9. It then was fixed in 3.7% formaldehyde with 0.2% (v/v) glutaraldehyde in 25 mM Pipes buffer, pH 6.9, embedded in a butyl-methylmethacrylate resin mixture, polymerized under UV light, and sectioned at 7 µm. After resin removal with acetone, sections were incubated in a blocking solution containing 5% skim milk powder in PBS containing 137 mM NaCl, 2.7 mM KCl, 2 mM $Na_2HPO_4$, 2 mM $KH_2PO_4$, pH 7.2 to 7.4, and 1% Tween 20 for ~45 min before application of the primary antibody. Sections were incubated in primary antibody solution for 2 h at room temperature or overnight at 4° C. before washing in 0.1% Tween 20 in PBS and application of the secondary antibody conjugated to fluorescein isothiocyanate (FITC). Sections were then incubated for 1 h at room temperature, washed extensively as described above, and stained with 0.01% toluidine blue 0 for 1 min to minimize tissue autofluorescence. The sections were mounted in Vectashield (Vector Laboratories) and examined by confocal laser scanning microscopy using the Zeiss LSM 510 instrument, with 488- and 568-nm argon-krypton lasers, generating the FITC signal (detected at 505 to 550 nm) and the autofluorescence signal (detected at >585 nm). These signals were detected in separate channels.

In the second method of tissue preparation, fresh material was sectioned with a razor blade and fixed in 4% paraformaldehyde in 50 mM Pipes buffer, pH 7, containing 5 mM $MgSO_4$ and 5 mM EGTA for 30 min. After fixation, the material was treated basically as the methylmethacrylate-embedded material, except that autofluorescence quenching was not needed. Because the autofluorescence of the walls was low, the FITC signal was projected on a transmitted light image for anatomical detail.

Antibodies

Monoclonal antibodies raised against recombinant protein PtSHR1 in rabbit were used to localize PtSHR1. Secondary antibodies were anti-rabbit FITC conjugates (Jackson ImmunoResearch Laboratories, West Grove, Pa.) used at a dilution of 1:100. Control and experimental preparations were processed in parallel and viewed at the same confocal laser scanning microscopy settings. To test for tissue autofluorescence, material was processed without the secondary antibodies. Primary antibodies were also saturated with the antigen at 10 nmol/mL to determine if the signal from experimental sections was attributable to the antibodies reacting with the target antigen or some other antibodies. These controls gave minimal background signals that were considered nonspecific.

Confocal Scanning Laser Microscopy

CLSM was carried out with a Leica TCS SP2 AOBS scanning system mounted on a Leica DM IRE2 inverted microscope employing Leica TCS software. An oil-corrected 633 objective NA=1.4 (HCX PL APO lbd.BL 63.0×1.40 01, Leica) and a water-corrected 633 objective NA=1.2 (HCX PL APO 63.0×1.20WED UV, Leica) were used. Excitation wavelengths were 488 nm (argon laser) for GFP and FITC and 340-380 nm for the counterstain, calcofluor white. Emission was detected between 505 and 520 nm for GFP, 520 and 550 nm for FITC and 420 and 440 nm for calcofluor white. Images were overlaid with Adobe Photoshop 7.0.

*Arabidopsis* Transformation and Growth

The pK7GWIWG2D(II) binary vector (Karimi et al., Trends Plant Sci. 2002 May; 7(5): 193-195) was used to transfer an inverted repeat DNA construct for AtSHR into Columbia (Col0) WT *Arabidopsis* plants using the floral dip method as previously described (Clough and Bent, 1998, Plant J 16:735-43). In addition, the following seed stocks were used: shr2 (homozygotic stock) in Col0 background, tpd::GUS line A1, homozygotic, in Columbia (Col) background (gift from Malcolm Bennett). Seeds germinated on plates were surface sterilized with 70% ethanol for 5 min, incubated in Bayrochlor (Bayrol, Planegg, Germany; one tablet per 400 ml $H_2O$) for 30 min, and washed three times with sterile, distilled water (dH2O). Sterilised seeds were plated on agar plates containing 1×MS medium (Duchefa Biochemie, Haarlem. The Netherlands), 1% plant agar (Duchefa), 1% sucrose (or 0% sucrose for etiolated growth), buffered to pH 5.7 with 1 M morpholinoethane-sulfonic acid (Sigma, Steinheim, Germany). Sterilised, plated seeds were vernalised at 4° C. in darkness for minimum three days and subsequently grown in continuous light or 16 hours light/8 hours dark at the photon flux density of 1780 $\mu E\, m^{-2}\, s^{-1}$, 70% relative humidity and a constant temperature of 23° C.

For detecting the glucuronidase (GUS) activity, fresh tissue sections were incubated for 16-18 hrs at 37° C. with gentle shaking in a substrate solution consisting of: 1 mM 5-bromo-4-chloro-3-indoyl-beta-D-glucuronide, cyclohexylammonium salt (BioVectra, PEI, Canada), 50 mM sodium phosphate buffer, pH=7.2, 0.1% Triton X-100, 1 mM $K_3[Fe(CN)_6]$ and 1 mM $K_4[Fe(CN)_6]$. The sections were then fixed for 10 min. in a fixing solution (5% formaldehyde, 5% acetic acid and 50% ethanol), washed few minutes in 50% and 100% ethanol and cleared by incubation in 0.24M HCl in 20% methanol at 57 C for 15 min., followed by 15 min in 7% NaOH in 60% EtOH at room temperature. Then the sections were rehydrated in a graded ethanol series (40, 20 and 10% EtOH), water and mounted in 50% glycerol. Sections were examined using an Axioplan 2 microscope and images were recorded with an AxioVision camera (both from Zeiss).

RT-PCT

Quantification of mRNA expression in transgenic hybrid Aspen lines was done according to the manufacturers protocol (Biorad). The realtime RT-PCR was run on a MyiQ PCR machine (Bio-Rad) using SYBR Green Supermix kit (Bio-Rad). Primer sequences for the RT-PCR analysis of PtSHR transcript levels in WT and RNAi lines were, 5'-CCATCAC-CTGACCTTCACTCC-3' (SEQ ID NO: 38) and 5'-TGT-TCGGATTGTTGTTGGAGAC-3' (SEQ ID NO: 39).

Results

Three Poplar Genes Code for SHR-Like Proteins

The GRAS protein family that includes SHR can be divided into a number of distinct subgroups based on sequence and function ((Bolle C., Planta. 2004 March; 218 (5):683-92)). A phylogenetic analysis of the most closely related Poplar and *Arabidopsis* homologs to the well-characterized AtSHR protein (*Populus tremula*: PtSHR1 (eugene3.01860017), PtSHR2A (eugene3.00070144), PtSHR2B (eugene3.00640143), PtSCL35b (eugene3.00050544), PtSCL53b (eugene3.00640007), PtSCL62 (fgenesh4_pm.C_LG_III000210), PtSCL69b (eugene3.00070272), PtSCL92b (eugene3.00030248), PtSCL97b (eugene3.00011016); *Arabidopsis thaliana*: AtSHR (At4g37650), AtSCL29 (At3g13840), AtSCL32 (At3g49950) (FIG. 1) indicated that there are three SHR-like genes in Poplar and that, of the three, PtSHR1 is the most closely related to AtSHR.

The entire poplar genome is publicly available on-line from the Joint Genome Institute website (currently available on-line at genome.jgi-psforg/Poptr1_1/Poptr1_1.home-.html) and is described in Tuscan et al. (2006) Science 313 (5793), 1596.

Figure 2:
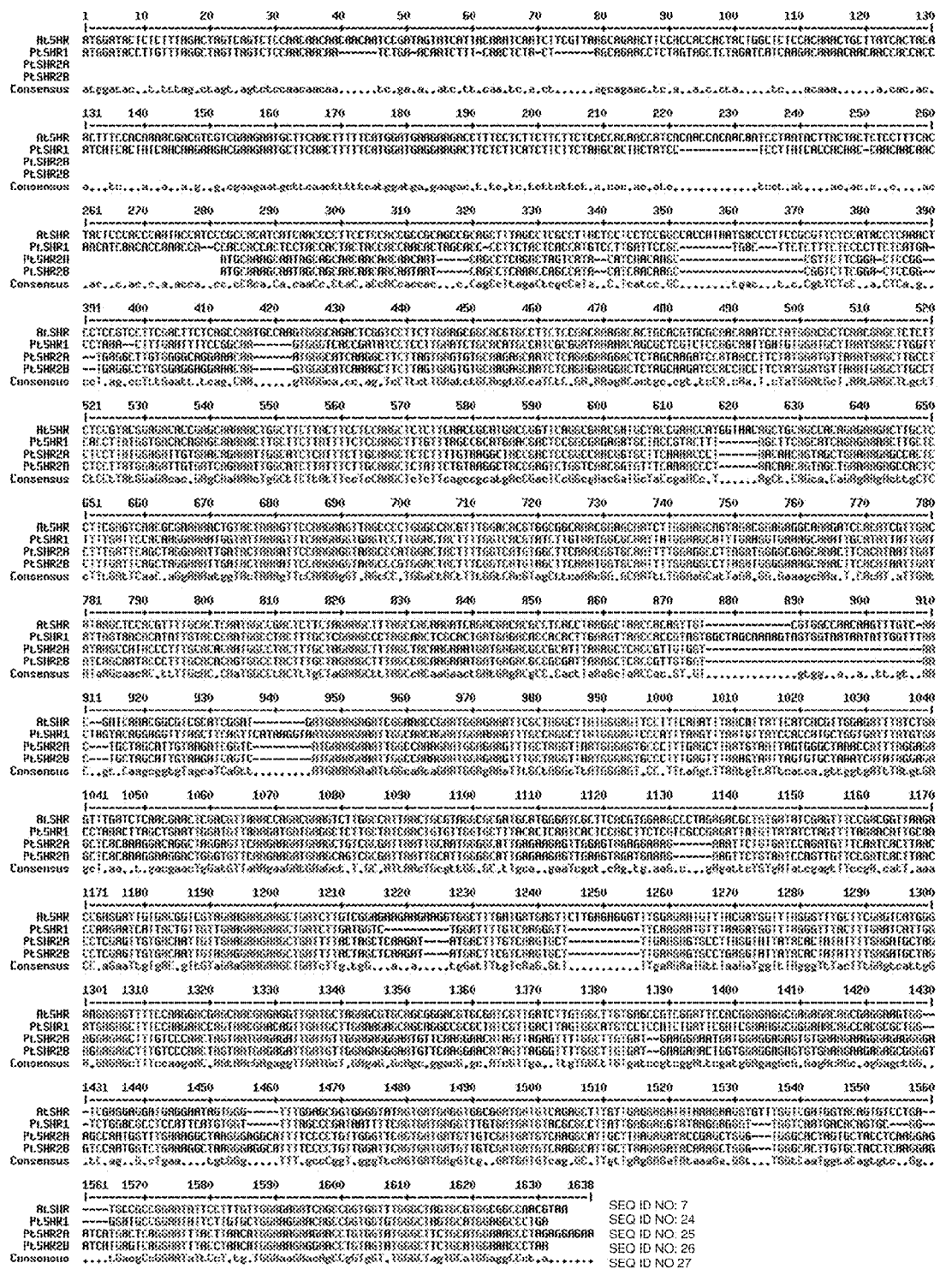

Multiple sequence alignments indicated strong sequence similarities between the Poplar nucleotide (FIG. 2) and amino acid sequences (FIG. 3) and the corresponding AtSHR sequences. PtSHR1 shares 67% nucleotide similarity with AtSHR, and the predicted 540 amino acid PtSHR1 sequence shares 73.52% similarity with the *Arabidopsis* sequence. The most obvious difference between the proteins is the approximately 110 N-terminal amino acid residues that are present in PtSHR1 and AtSHR, but are absent from PtSHR2A and PtSHR2B (FIG. 3). The predicted 411 amino acid sequences of PtSHR2A and PtSHR2B share 93% amino acid identity over the length of the sequences and 71.14% and 68.78% amino acid similarity with AtSHR, respectively. All three Poplar SHR-like sequences contain variations on the distinguishing GRAS family-specific VHIID (SEQ ID NO: 40) motif and its requisite surrounding leucine-rich regions (FIG. 3). They also all contain the conserved GRAS C-terminal SAW motif, but only PtSHR2A and PtSHR2B contain variations on the RVER (SEQ ID NO: 41) motif present in many GRAS protein family members. The genomic sequences of all three genes are similar, with no intron-encoding sequences present.

Partial Suppression of PtSHR1 Leads to an Acceleration of Growth

Figure 7:
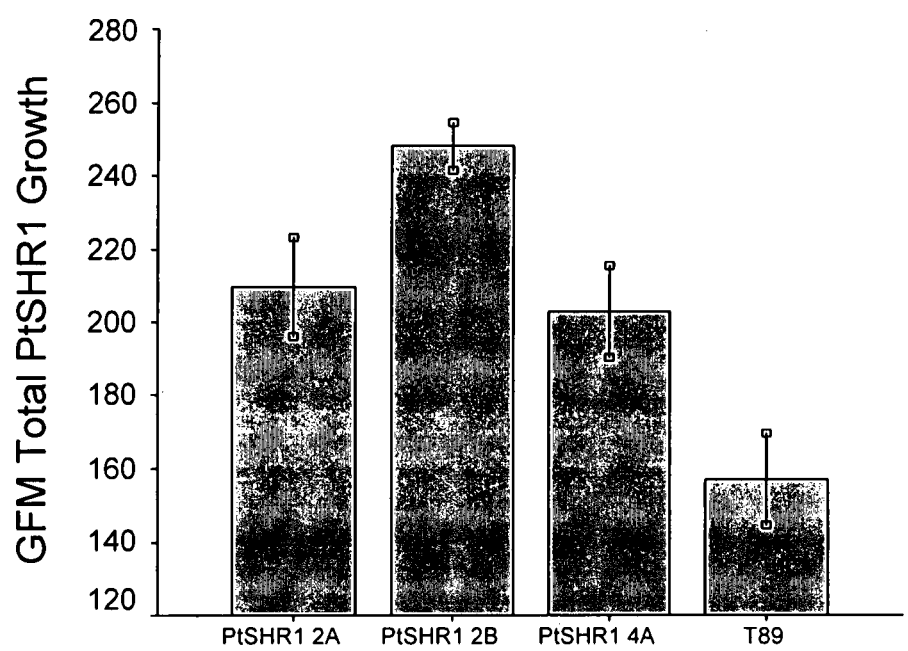
Figure 8:
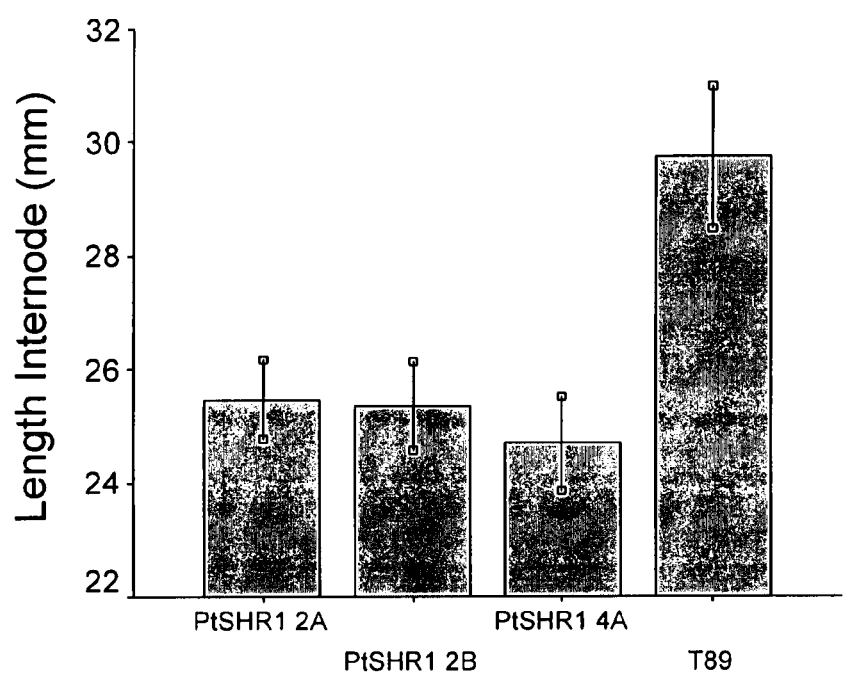
Figure 9:
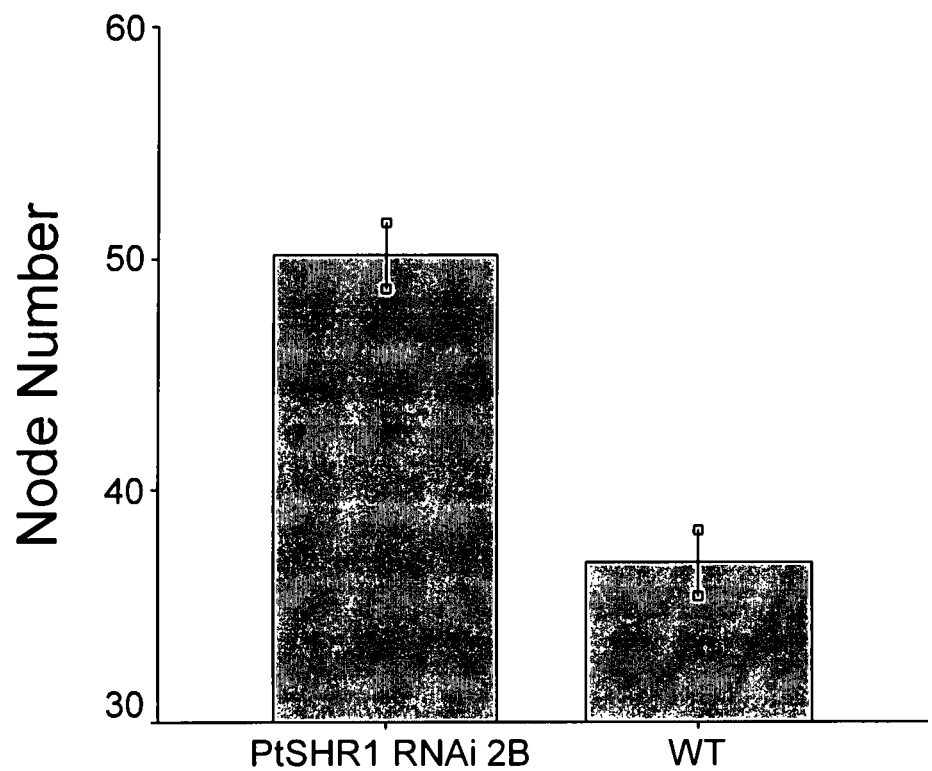

The in planta functions of the Poplar SHR-like genes were investigated by suppressing the expression of PtSHR1. In contrast to our expectations, of the 24 independent transformation lines generated, none showed reduced growth, but many showed a marked increase in both primary (height) (FIG. 4, Table 1) and secondary (girth) (FIGS. 5 and 6) growth. The combined effect was a substantial increase in total above-ground biomass accumulation after 52 days growth in the glasshouse (FIG. 7). The lines that showed an increase in growth were found to have a partial suppression of PtSHR1 transcripts. Three lines, representing independent transformation events. Line 2A. Line 2B and Line 4A, had 50-80% of the levels of PtSHR1 transcripts found in WT trees. Growth was measured in trees that began as uniform three leaf Poplar cuttings (insert FIG. 4). After 4 weeks in tissue culture, the trees were transplanted into soil and moved to the glasshouse. From the first measurement (16 days after transplantation, DAT), the transgenic lines were significantly taller than the control, T89, plants (Table 1). By 52 DAT, RNAi Line 2B plants were on average 27% taller than WT T89 plants. This was despite the average internode length of the transgenic plants being significantly smaller than the WT plants (FIG. 8). The increased height resulted from an accelerated rate of node (leaf) production in the transgenic lines (FIG. 9).

Figure 4:
Figure 5:
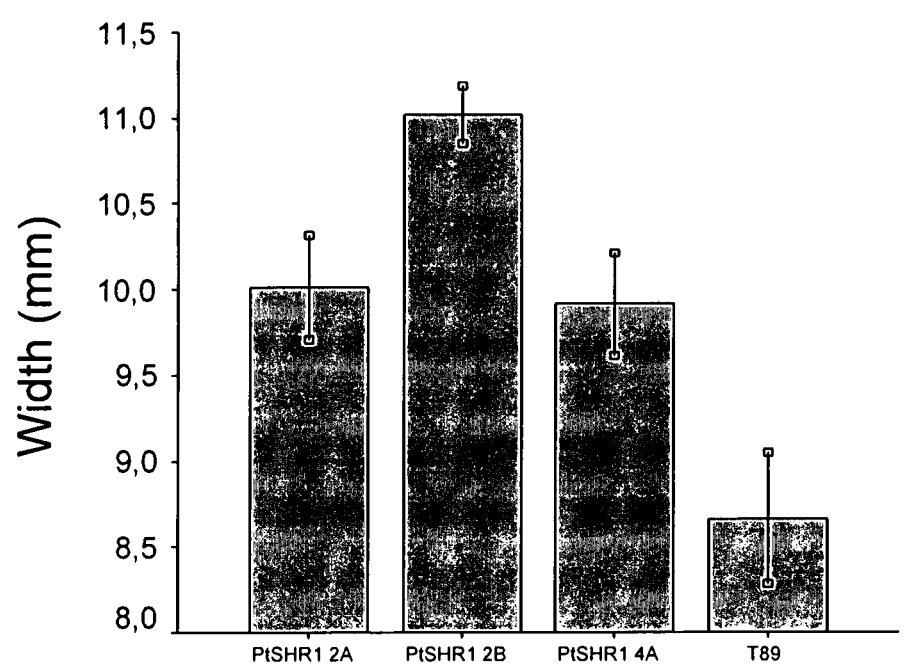
Figure 6:
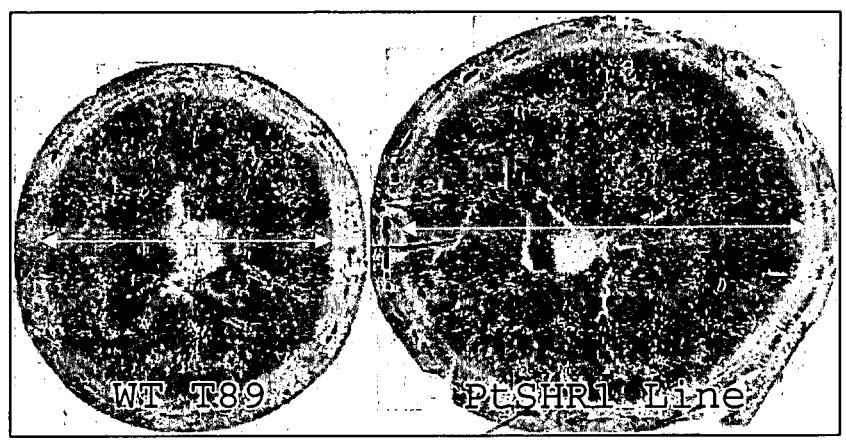
Figure 10:
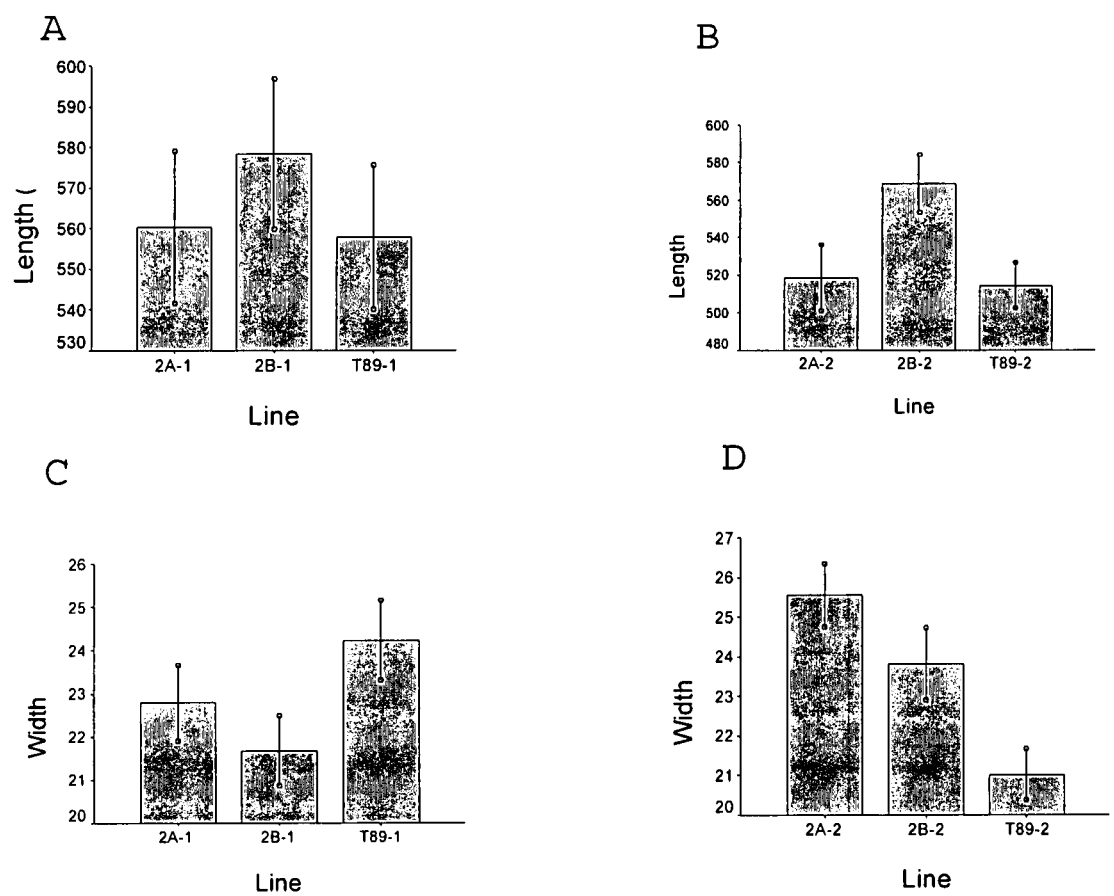
Figure 16:
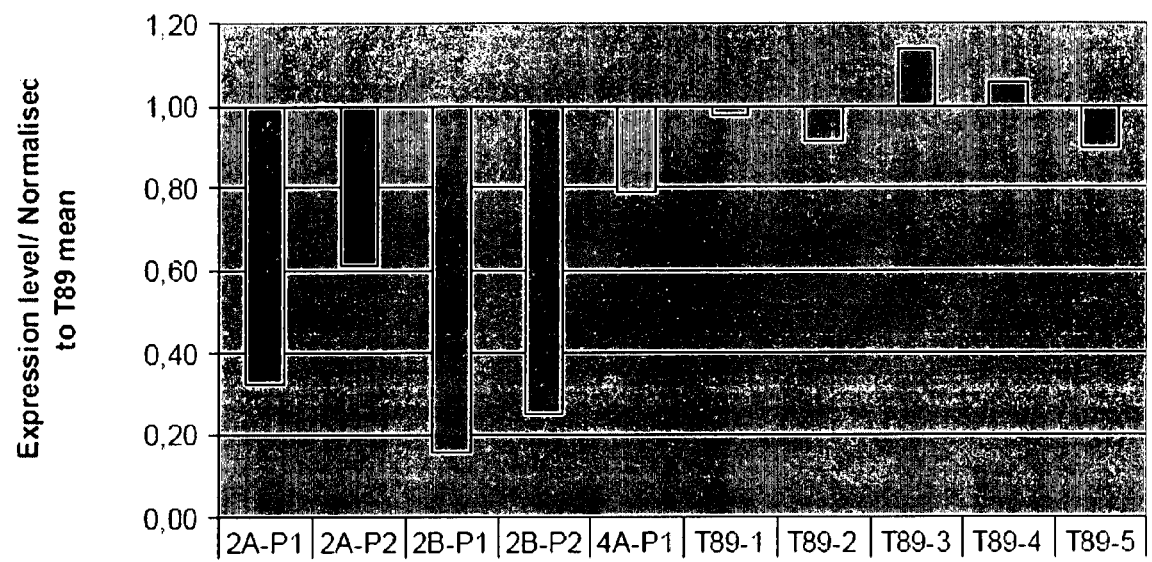
FIG. 16 shows transcript levels of three independent SHR RNAi suppression lines of Aspen (2A-P in two replicates, 2B-P in two replicates and 4A-P) and five WT T89 lines, determined by RT-PCR.

The increase in girth resulted from a proportional increase in the width of the various components of the stem (FIG. 6). There was no consistently significant difference in the length and width of tracheids between the transgenic and WT plants (FIG. 10), indicating that the increased growth was predominantly the result of an increase in cell number. There were also no significant differences in leaf shape or average fully expanded leaf surface area and fresh weight between the transgenic lines and WT trees (FIGS. 11A and 11B). Poplar cuttings establish through the production of adventitious roots. We were unable to observe any differences in root establishment or early root growth between the RNAi and WT T89 plants.

mRNA expression was quantified in transgenic hybrid aspen lines (*Populus tremula×Populus tremuloides*, clone T89) using RT-PCR. The partial suppression 20-80% of WT levels of steady-state PtSHR1 transcript levels seen in FIG. 16 and Table 6 resulted in a dramatic acceleration of both primary and secondary growth compared to wild-type (WT) T89 trees (FIGS. 4, 5 and 6).

*Arabidopsis* shr Mutant Shoots have Altered Secondary Vascular Development

In stark contrast to the phenotype of the Poplar knockdown lines, the shoots of *Arabidopsis* shr knockout lines are clearly dwarfed. Despite this, we examined shr hypocotyls and floral stems in order to reveal discrepancies or similarities that would shed light on the Poplar phenotype. Secondary growth was clearly reduced in the mutant. Transverse sections through the hypocotyl of flowering plants revealed a reduction in the thickness of shr hypocotyls compared to the WT. The vascular bundles in the mutant hypocotyls were small and irregular and lacked the typical WT radial alignment of vessels. The hypocotyls of flowering WT plants had a considerable amount of secondary xylem produced by the activity of the vascular cambium and a thick periderm produced by cork cambium activity. In contrast, the hypocotyls of flowering shr plants exhibited very little vascular cambium activity, producing 3-9 layers of secondary xylem. There was also no apparent cork cambium.

Figure 12:
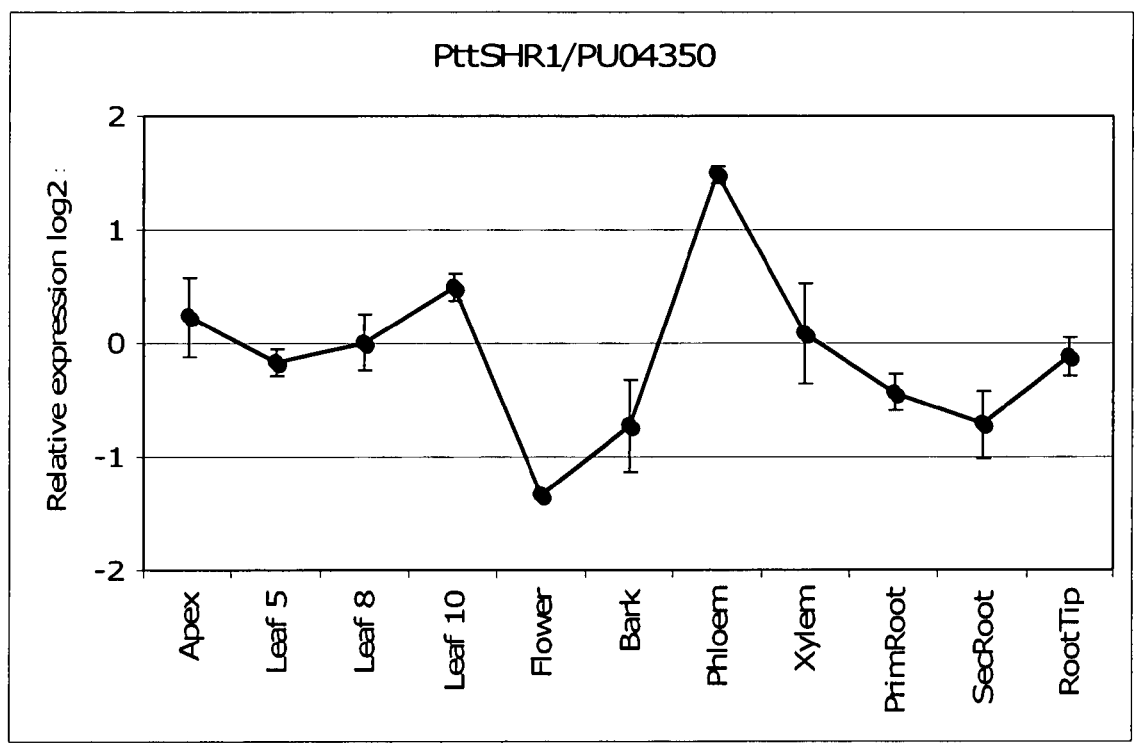

Similar Expression Patterns for AtSHR and PtSHR1 Provide Further Evidence that they are Functionally Equivalent Expression data from the BASE Poplar microarray database showed that PtSHR1 transcripts were present in a wide variety of organs (FIG. 12). We used native promoter:reporter constructs and immunohisto-localisation to more precisely determine PtSHR1 and AtSHR expression patterns. PtSHR1 promoter-driven GFP expression was similar to the published root profile for AtSHR expression (Nakajima et al., Nature. 2001 Sep. 20; 413(6853):307-11). In roots, a 2.5 kbp sequence upstream of the PtSHR1 coding sequence drove GFP expression in the stele and during the initiation and early development of lateral roots. In the shoots, GFP was observed in the vasculature of leaves, branches and the main stem. In transverse and radial longitudinal sections of fully expanded internodes in actively growing two month old poplar stem, GFP was observed throughout the cambial zone (CZ). The CZ is the zone of cell division where stem cells and the transit amplifying (mother) cells undergo divisions, forming new cells for continued xylem (wood) and phloem formation and the consequent increase in girth. GFP was also observed in the phloem parenchyma and in the ray parenchyma and initials. GFP was observed in the ray files through the cambium to the phloem and deep into the maturing xylem (sapwood). Immunofluorescence labeling with a monoclonal anti-PtSHR1 antisera also indicated the presence of PtSHR1 epitopes in these cells. Immunofluorescent labelling was completely inhibited by a competitor PtSHR1 polypeptide.

In the shoot apex, GFP was observed in a group of cells in the corpus, immediately below the tunica in the apical dome. There was also strong GFP expression in the procambial tissues and leaf primordia. Immunofluorescence labelling of radial longitudinal sections through the shoot apex demonstrated the occurrence of PtSHR1 epitopes throughout the apical dome and flanking tissues, providing indication that the protein acts, at least in part, non-cell-autonomously in the shoot apex. Transverse sections immediately below the apex showed GFP expression isolated to the fascicular procambium, however, by internode 4 the expression had extended to the interfascicular procambium and could be observed wherever there was developing vasculature, for example in leaf traces in the stem.

In *Arabidopsis*, native promoter-driven GUS activity indicated that, similarly to PtSHR1 in Poplar, AtSHR is expressed throughout the vasculature of roots and shoots. GUS activity was observed in the vasculature of newly emerged seedlings and in fully developed cotyledons and rosette leaves. It was also observed in the vasculature of the various parts of the flower. When interfascicular cambial activity was present in the inflorescence stems, GUS was found in both the fascicular and interfascicular cambial zones. In the hypocotyl exhibiting secondary growth, activity was associated with the cambial zone and the phloem side of this zone, similarly to the GFP expression in the promPtSHR1:GFP lines. In addition, some GUS labelling was scattered in the secondary xylem of both stems and hypocotyls where it was associated with paratracheal parenchyma.

PtSHR1 Complements the shr Mutant Phenotype

In order to test whether the Poplar PtSHR-like proteins are capable of functioning similarly to AtSHR, at least in *Arabidopsis*, we individually expressed the coding sequences for PtSHR1, PtSHR2A and PtSHR2B, driven by a 2.5 kbp 5' upstream sequence of the native AtSHR promoter, in the shr2 (Col0) loss-of-function mutant. Polymerase chain reaction verification showed that there was expression of the constructs in the respective complemented lines. The primer sets for PtSHR2A and PtSHR2b amplified sequences in both PtSHR2 complemented lines because of the almost identical nucleotide sequences of the two genes. All three PtSHR genes were able to partially complement the shr2 mutant phenotype. The dwarf root and shoot growth phenotype was fully complemented, but the floral stems of the complemented lines remained agravitropic. Interestingly, complementation of the shr mutant with an AtSHR:GFP fusion protein driven by a similar AtSHR promoter sequence also failed to complement the agravitropic shoot phenotype. Also, ectopic CaMV 35S promoter-driven expression of AtSHR in WT (Col0) *Arabidopsis* plants resulted in a loss of floral shoot gravitropism. Together, these results provide indication that a precise spatio/temporal control of AtSHR expression is necessary for this aspect of AtSHR function.

Partial Suppression of AtSHR in *Arabidopsis* Leads to a Similar Phenotype to that Observed in the Poplar PtSHR1 RNAi Lines.

Figure 13:
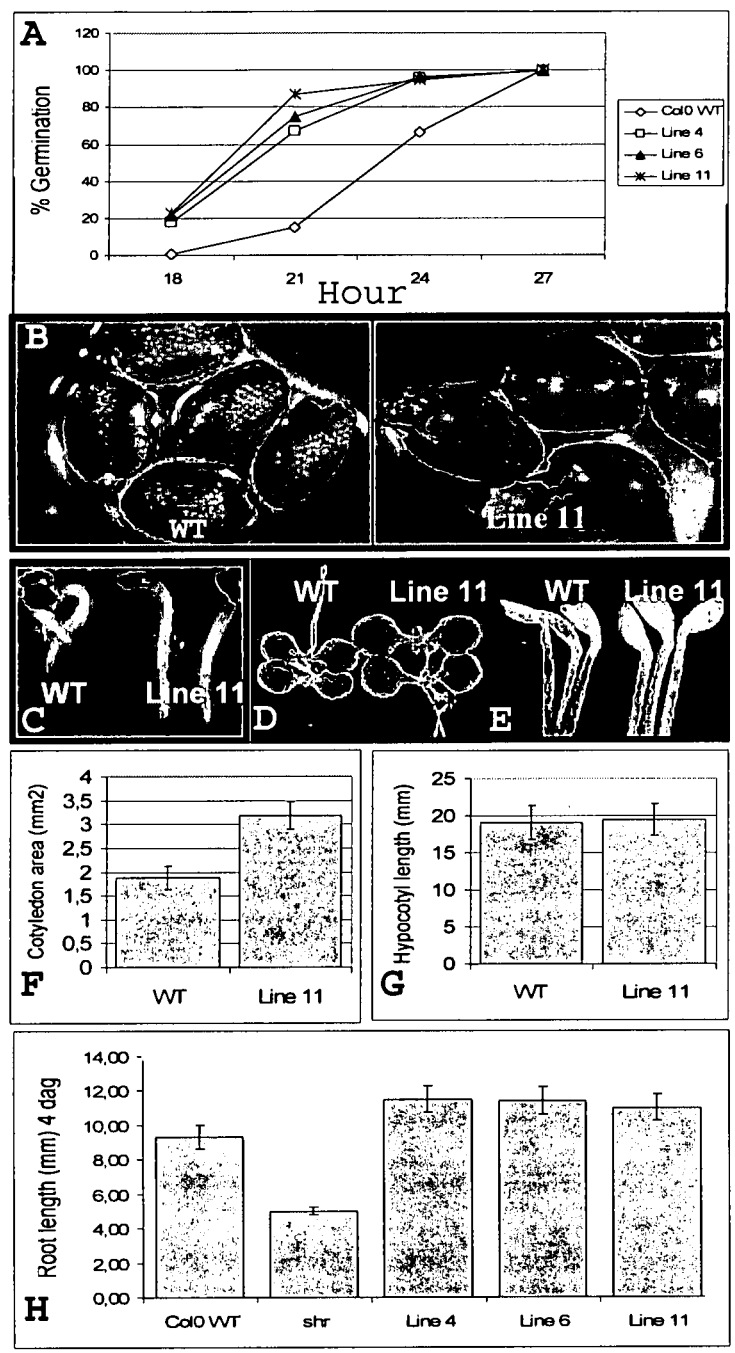

Another possibility for the discrepancy between the loss of function phenotype in the shr mutant and the knockdown phenotype in the Poplar lines is that there may be fundamental differences between a reduction and total absence of the protein. As all of the shr mutant alleles are null, we used an RNAi strategy in *Arabidopsis* similar to that used in the Poplar transgenics in order to obtain lines that retained a remnant expression of AtSHR. We generated 26 individual RNAi AtSHR suppression lines. Three lines were chosen. Lines 4, 6 and 11, that had between 40 and 75% of the normal levels of AtSHR transcripts found in WT plants. These lines all showed a substantial acceleration of several aspects of vegetative development. After 3 days stratification at 4° C., populations of WT (Col0) seeds took from 18 to 27 hours to fully germinate (radical emergence) in the light at 23° C. on agar plates containing 1×MS and 1% sucrose (FIG. 13A). The seed samples from the three RNAi suppressed lines commenced germinating several hours before the WT seeds and had fully germinated three hours before the WT population reached the same level of germination (FIGS. 13A and 13B). Forty hours after placing the seeds at 23° C., in contrast to the WT seedlings, most of the transgenic seedlings had fully emerged from the seed coat and were rapidly elongating (FIG. 13C). At 5.5 days, the cotyledons (FIGS. 13D and 13F) and roots (FIG. 13H) of RNAi seedlings grown in the light were substantially bigger than those of the WT growing on the same plates. In contrast, at 5.5 days there were no significant differences between WT and RNAi line hypocotyl lengths and cotyledon sizes of etiolated seedlings grown on 0% sucrose plates (FIGS. 13E and 13G).

Boyes et al. (Boyes et al., The Plant Cell, Vol. 13, 1499-1510, 2001) published a model for the growth stages of *Arabidopsis* plants. In the transgenic lines, growth stage 1.06 (six rosette leaves > than 1 mm in length) was reached by 15 days after sowing (FIG. 14A). WT seedlings did not reach this stage until day 18 (FIG. 14B). By day 18, immature leaves 1 and 2 were fully expanded in both the WT and the transgenic lines. At this stage, there was no significant difference between the WT and RNAi leaf areas (FIG. 14C). In contrast, the combined area of all of the emerged leaves on each plant was significantly greater in the RNAi lines (FIG. 14E and compare FIGS. 14B & 14D) than in the WT. This was due to both the larger size of the expanding leaves and the emergence of more leaves in the RNAi lines. In other words, the RNAi plants were more developmentally advanced than the WT. At 18 days, radial longitudinal sections indicated that the apical domes of the Line 11 plants were substantially larger than the WT (FIG. 14F).

Height Growth Rate of Poplars

FIG. 4 and Table 1 show an example of height comparisons of Poplar RNAi and T89 WT plants. From Table 1, it can be seen that the height growth advantage is greatest during the early phase of growth. Because growth phases have different timing in different plants and there is some noise added, the method described above is useful in calculating the maximum growth speed in these conditions for the different individual trees. These results (using fewer biological replicates for each independent transformation event) can be seen in Tables 4 and 5.

Diameter Growth Rate

Under the above defined growth conditions, stem width exhibit a comparatively linear increase over time. Linear regression on diameter data was used for estimating diameter growth.

$$d(t) = c*t + d_0$$

where $d_0$ is the initial width and c is the rate of diameter growth (slope).

These height and width growth measurements were compared between WT T89 and the transgenic RNAi plants. For these results, the WT T89 plants were collectively called the wild-type population and the transgenic trees were collectively called the construction group.

Table 4 shows growth data for the KR462 (PtSHR1 RNAi) construction group and corresponding wild-type group. Table rows contain height and diameter measurements of individuals of the KR462 (PtSHR1 RNAi) group and control wildtype group. This data is summarised in Table 5. The KR462 (Pt-SHR1 RNAi) construct was found to increase the height growth rate by approximately 12% and the diameter growth rate by approximately 18%.

Partial Suppression of SHR Accelerates Morphogenesis in Determinate and Indeterminate Species.

In *Arabidopsis*, the complete absence of the AtSHR protein leads to the collapse of the root meristem, the dwarfing of the shoots and a reduction in secondary growth. In contrast, we have observed that in both Poplar and *Arabidopsis* the effect of the partial suppression of PtSHR1 and AtSHR, respectively, leads to an acceleration of the rate of growth of the shoots. The increased growth rate appears to be due to an increased rate of mitotic divisions in the VC and the shoot apical meristem (SAM).

Many plants have evolved mechanisms for avoiding shading from neighbouring plants by increasing height through increased elongation of internodal cells. In the Poplar transgenic lines, the internodes were shorter than the WT T89 lines and there was no significant difference in the lengths of tracheal elements between the WT T89 plants and the transgenic plants. Increased height, without a commensurate increase in internode or cell length indicates that, similarly to the increase in girth, the accelerated height growth was the result of additional cell divisions. The combination of taller plants, shorter internodes and no reduction in cell length indicates that the plastochron, the timing of the production of new organs in the SAM, is decreased in the transgenic lines. A number of mutants have been identified where the plastochron is affected. For example, the maize terminal earl, tel (Velt et al., 1998. Nature 393, 166-168) and *Arabidopsis* altered meristem program 1, amp1 (Chaudhury et al., 1993. Plant Journal 4, 907-916; Helliwell et al., 2001. Plant Cell 13, 2115-2125). In addition to an altered plastochron these two mutants have altered phyllotaxy (the fraction of the circumference that seperates two successive leaves on a stem). Phyllotaxy did not differ between the Poplar WT T89 and RNAi transgenic plants nor between the *Arabidopsis* WT and RNAi lines. One mutant has recently been identified in rice that has a reduced plastochron (Miyoshi et al., PNAS Vol. 101 No. 3 2004, 875-880). The PLASTOCHRON 1 gene encodes a cytochrome P450 that is expressed in leaf primordia. Similarly to the PtSHR1 and AtSHR RNAi lines, the plastochron 1 mutant is affected in the timing of the production of new leaves, but is not affected in spacing (phyllotaxy) of new leaf initiation (Miyoshi et al., PNAS Vol. 101 No. 3 2004, 875-880).

Several Lines of Evidence Provide Further Indication of Conserved Function Between PtSHR1 and AtSHR Given that the mis-regulation of PtSHR1 and AtSHR both affected VC activity, we considered that there may be conserved patterns of transcript accumulation in the two species. The BASE global transcript microarray data indicated that PtSHR1 was expressed in various organs throughout the root and shoot (FIG. 12). Native PtSHR1 promoter-driven GFP expression also indicated that the gene is expressed throughout the shoot and that this expression is associated mostly with vascular development. In the shoot apex, GFP was observed in a group of cells in the corpus, immediately below the tunica in the apical dome. The combination of a lack of a GFP signal and the presence of immunofluorescent labeling in zones flanking the central zone of the SAM suggests that PtSHR1 has the ability to move from cell to cell. In *Arabidopsis*, cell-to-cell movement of AtSHR is critical for the function of the protein and proper root development (Nakajima et al. Nature. 2001 Sep. 20; 413(6853):307-11; Benfey et al., Benfey et al., Development. 1993 September; 119(1):57-70). Shoot tip growth is ultimately derived from a population of stem cells in the centre of the SAM (Fletcher J C., 2002 Annual Review of Plant Biology, 53, 45-66). Another mechanism by which PtSHR1 epitopes could be present in cells where the gene is not expressed is that the gene could be expressed in the stem cells and could then be retained in these cells and daughter cells as they move out from the apex during cell division and apical development. GUS staining in the *Arabidopsis* promAtSHR:GUS lines indicated that AtSHR is expressed in similar zones throughout the *Arabidopsis* plant providing further evidence that the two proteins carry out the same functions.

Further evidence in support of this hypothesis is that all three Poplar PtSHR-like proteins were able to individually complement the shr2 loss-of-function mutant phenotype when driven by the driven by a 2.5 kbp 5' upstream sequence of the native AtSHR promoter (and by the constitutive CaMV 35S promoter).

Partial Suppression of AtSHR in *Arabidopsis* Leads to a Similar Phenotype to that Observed in the Poplar PtSHR1 RNAi Lines.

The phenotype of the AtSHR knockdown lines provided further strong evidence in support of the hypothesis that PtSHR1 and AtSHR have similar functions. Vegetative development is accelerated in the PtSHR1 RNAi lines. In *Arabi-*

Figure 14:
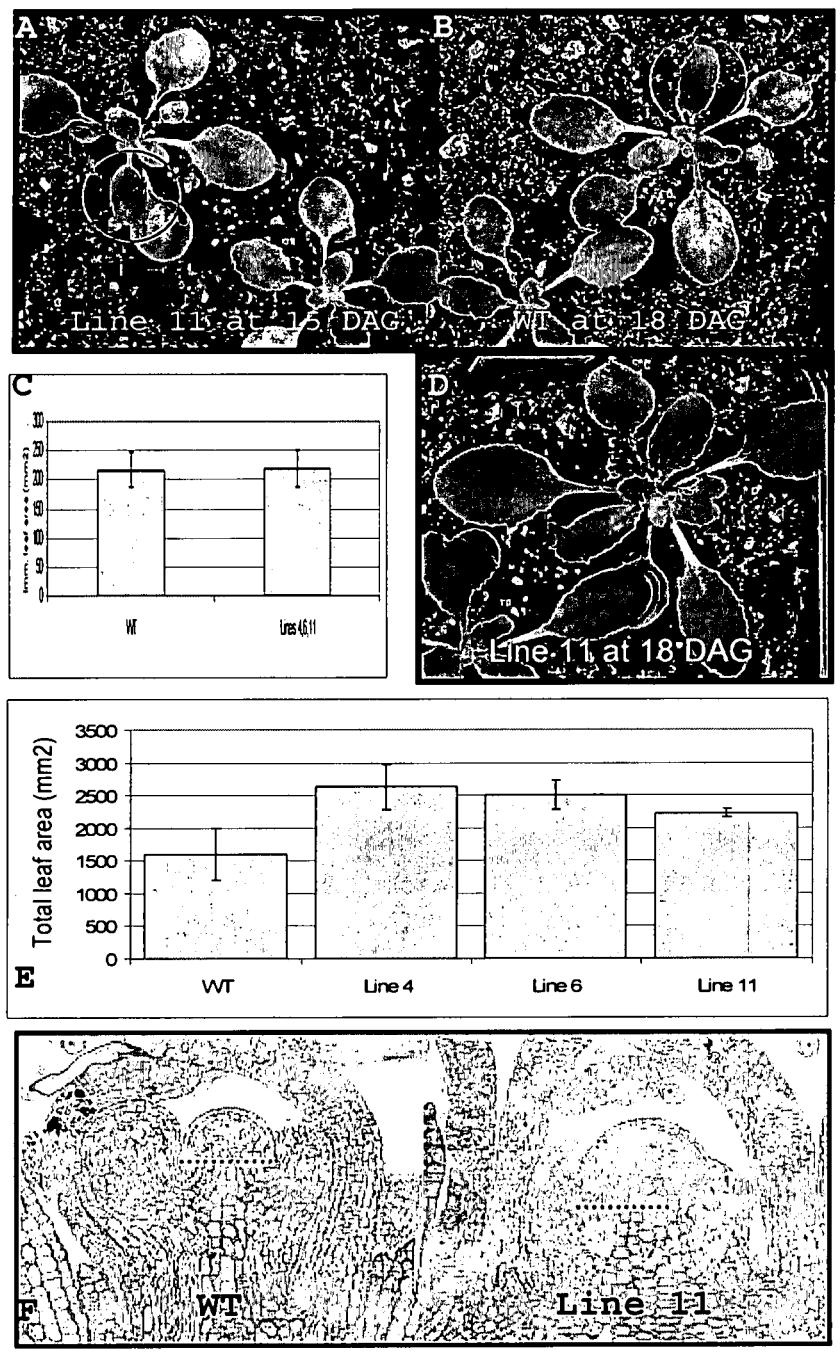

*dopsis*, already by germination, the AtSHR RNAi lines were developmentally about 3 hours advanced on the WT seedlings. Boyes et al. (Boyes et al., The Plant Cell, Vol. 13, 1499-1510, 2001) published analyses of *Arabidopsis* that defined a series of growth stages for use in the analysis of transgenic and mutant lines. Their growth stage 1.06 was reached by 15 days after sowing in the transgenic line (Line 11) (FIG. 14). This stage was not reached in the WT seedlings until day 18. Combined with the data showing that there was no difference in the final fully expanded size of leaves 1 and 2, this indicates that, similarly to the PtSHR1 RNAi lines, the affect of the suppression of AtSHR expression is to increase the rate of new organ initiation, but not the final size of those organs. This data suggests strongly that there is a fundamental difference between reduced expression and a total lack of the AtSHR protein.

shr Mutant Shoots have Altered Morphology, but the Plastochron Remains Unchanged.

The sum total of our data provides strong evidence that AtSHR and PtSHR1 are functionally equivalent. In both Poplar and *Arabidopsis* transgenic lines, a decrease in the levels of SHR transcripts led to an increased growth rate. This suggests that the proteins act as negative regulators of cell division and growth. In the shr mutants, where there is a total absence of the protein, the root apical meristems collapse, the shoots are dwarfed and secondary vascular development is greatly reduced. Clearly, some level of AtSHR is essential for normal cell division in both the roots and shoots. The rate of vegetative development and the timing of vegetative to floral transition are not delayed in the shr mutants, however. At flowering they have, on average, the same number of leaves as WT plants. This provides indication that, whereas SHR regulates cell division and vegetative development in the shoot, the decreased plastochron in the both the *Arabidopsis* and Poplar RNAi lines is a secondary effect of the suppression of SHR gene expression. The primary effect is a stimulation of cell division in the SAM.

TABLE 1

| | Lines | | | |
|---|---|---|---|---|
| Days after planting | RNAi Line 2A | RNAi Line 2B | RNAi Line 4A | WT T89 |
| 16 days | 2161 (17) | 239* (25) | 205* (33) | 175 (23) |
| 28 days | 429*** (42) | 508*** (50) | 412*** (35) | 336 (42) |
| 40 days | 933*** (84) | 1053*** (64) | 913*** (80) | 778 (65) |
| 52 days | 1364*** (95) | 1497*** (57) | 1316** (105) | 1173 (75) |

Means (n = 9) of heights of trees (SDs within parentheses) for glasshouse growth comparison of PtSHR1 RNAi lines 2A, 2B and 4A with control T89 trees
Stars indicate the significance value of the mean difference between each line and the Wild Type T89 (tested with Dunett's post hoc test to compare all samples with a control)
*p < .05,
**p < .01,
***p < .001

TABLE 2

| Species | SEQ ID NO: | Database Reference |
|---|---|---|
| Poplar SHR1 | 2 | JGI ID: Poptr1:586010 eugene3.01860017 |
| Poplar SHR2A | 4 | eugene3.00070144 |
| Poplar SHR2B | 6 | eugene3.00640143 |
| *Arabidopsis* SHR | 8 | NP_195480.1 GI:15235646 |
| Rice SHR | 10 | AAS07303.1 GI:41469537 |
| Rice SHR | 12 | BAD30442.1 GI:50509213 |
| Barley SHR | 14 | HvGI TC147542 |
| Barley SHR | 16 | AAL66734.1 GI:18254373 |

TABLE 3

| | |
|---|---|
| AFH | Average final height of the wild type population and the Construction group population |
| AFD | average final diameter of the wild type population and the Construction group population |
| AMHGR | average Maximum height growth rate of the wild type population and the Construction group population |
| ADGR | Average diameter coefficient of the wild type population and the Construction group population |
| MFH | Maximum final height of the wild type population and the Construction group population |
| MFD | Maximum final diameter of the wild type population and the Construction group population |
| MMHGR | Maximum of Maximum height growth rate of the wild type population and the Construction group population |
| MDC | Maximum diameter coefficient of the wild type population and the Construction group population |

TABLE 4

| | Height (cm) | | | | | | | Diameter (mm) | | | | | |
|---|---|---|---|---|---|---|---|---|---|---|---|---|---|
| Days in greenhouse | 18 | 26 | 33 | 39 | 47 | 53 | 65 | 33 | 39 | 47 | 53 | 59 | 65 |
| KR462 (PtSHR1)-2A-A | 28 | 44 | 62 | 100 | 120 | 143 | 193 | 4.9 | 6.6 | 7.7 | 9.1 | 8.5 | 9.3 |
| KR462 (PtSHR1)-2A-B | 26 | 42 | 63 | 99 | 116 | 137 | 181 | 4.6 | 5.8 | 5.8 | 6.5 | 6.9 | 7.5 |
| KR462 (PtSHR1)-2B-A | 18 | 28 | 38 | 65 | 80 | 99 | 140 | 3.5 | 5.3 | 6.1 | 6.9 | 7.8 | 7.9 |
| KR462 (PtSHR1)-4A-A | 20 | 40 | 57 | 95 | 112 | 133 | 168 | 4.6 | 6.4 | 7.4 | 8.5 | 8.7 | 9.9 |
| KR462 (PtSHR1)-5A | 17 | 27 | 39 | 67 | 83 | 100 | 140 | 3.7 | 5.1 | 6.2 | 7.1 | 7.5 | 8.3 |
| T89-133 | 23 | 37 | 51 | 84 | 103 | 121 | 156 | 4.7 | 6.7 | 7.7 | 8.4 | 9.1 | 9.7 |
| T89-134 | 25 | 38 | 50 | 80 | 95 | 112 | 149 | 4.4 | 6.2 | 7.1 | 7.6 | 7.6 | 8.4 |
| T89-135 | 17 | 29 | 43 | 71 | 86 | 104 | 140 | 4.8 | 6.6 | 7.7 | 8.6 | 9.1 | 9.1 |
| T89-136 | 19 | 31 | 45 | 72 | 85 | 103 | 138 | 4.6 | 5.3 | 6.0 | 6.4 | 7.3 | 7.8 |
| T89-137 | 22 | 37 | 52 | 82 | 96 | 112 | 151 | 5.0 | 6.5 | 7.3 | 7.8 | N/A | 10.0 |
| T89-138 | 21 | 33 | 47 | 78 | 94 | 109 | 140 | 4.9 | 6.0 | 7.0 | 7.8 | 8.4 | 9.0 |
| T89-139 | 24 | 39 | 56 | 92 | 108 | 124 | 159 | 4.8 | 5.7 | 6.3 | 7.0 | 7.6 | 8.4 |
| T89-140 | 25 | 41 | 56 | 88 | 101 | 115 | 148 | 4.9 | 6.0 | 6.0 | 6.8 | 7.0 | 7.8 |
| T89-141 | 17 | 30 | 45 | 77 | 87 | 104 | 132 | 5.0 | 5.3 | 6.2 | 6.4 | 6.9 | 7.2 |
| T89-142 | 24 | 38 | 54 | 85 | 99 | 116 | 146 | 5.3 | 5.9 | 6.3 | 6.6 | 7.6 | 8.3 |

TABLE 4-continued

| | Height (cm) | | | | | | Diameter (mm) | | | | | |
|---|---|---|---|---|---|---|---|---|---|---|---|---|
| Days in greenhouse | 18 | 26 | 33 | 39 | 47 | 53 | 65 | 33 | 39 | 47 | 53 | 59 | 65 |
| T89-143 | 24 | 40 | 56 | 89 | 107 | 122 | 155 | 4.7 | 5.7 | 6.3 | 6.8 | 7.3 | 8.4 |
| T89-144 | 23 | 37 | 52 | 76 | 89 | 107 | 139 | 4.5 | 5.9 | 6.5 | 6.9 | 7.1 | 7.9 |
| T89-146 | 27 | 43 | 58 | 84 | 99 | 116 | 153 | 4.6 | 6.0 | 6.7 | 7.4 | 7.8 | 8.5 |
| T89-147 | 26 | 44 | 62 | 95 | 111 | 130 | 167 | 5.4 | 6.5 | 6.9 | 7.4 | 8.0 | 8.7 |
| T89-148 | 21 | 32 | 47 | 77 | 91 | 109 | 146 | 4.2 | 5.4 | 6.1 | 6.6 | 6.9 | 7.8 |

TABLE 5

| Construction group | AFH Average Final Height (KRmean/ WTmean) | AFD Average Final Diameter (KRmean/ WTmean) | AMHGR Average height growth rate (KRmean/ WTmean) | ADGR Average Diameter Coefficient (KRmean/ WTmean) | MFH Maximum Final Height (KRmax/ WTmax) | MFD Maximum Final Diameter (KRmax/ WTmax) | MMHGR Maximum height growth rate Maxima KRmax/ WTmax) | MDC Maximum Diameter Coeffict (KRma: WTmax) |
|---|---|---|---|---|---|---|---|---|
| KR462 | 1.11 | 1.01 | 1.12 | 1.18 | 1.16 | 0.99 | 1.10 | 1.05 |

TABLE 6

| | Plant | | | | | | | | | |
|---|---|---|---|---|---|---|---|---|---|---|
| | 2A-P1 | 2A-P2 | 2B-P1 | 2B-P2 | 4A-P1 | T89-1 | T89-2 | T89-3 | T89-4 | T89-5 |
| PtSHR1 Expression Normalised to T89 mean | 0.32 | 0.61 | 0.16 | 0.25 | 0.79 | 0.98 | 0.91 | 1.14 | 1.05 | 0.90 |

Sequences

PtSHR1 eugene3.01860017
(SEQ ID NO: 1)

GGGAGAAGACTGGGCTAGCTAGCTAGATAAAAGAATATCCCAAACCCCACCCAATTTGATTCACATCGAC

TACAGAAAAGAAAAGCACATTTAAACATGTATGTATGTATATATATGTATATATATAAATATCCAACTT

CAAGATCCTCTCTTTTATCATTCTCTACCCCAATATTCCCACAGTTAAAAACACAAACACCCATCCCCTT

ACCTTCACTCCAAGCCATCCCCAACAAACTCCATCCGAATTCTATTGATGTGGGTCTCTGGATTTTGGTT

AAATGGATACCTTGTTTAGGCTAGTTAGTCTCCAACAACAATCTGAACAATCTTTCAACTCTACTAGCAG

AACCTCTAGTAGCTCTAGATCATCAAGACAAAACAACAACCACCACCATCATCACTATCAACAAGAAGAC

GAAGAATGCTTCAACTTTTTCATGGATGAGGAAGACTTCTCTTCATCTTCTTCTAAGCACTACTATCCTC

CTTATCACCACAACCAACAACAACATCAACACCAAACCACCACCACCACTCCTACCACTACTACCAC

CAACACTAGCACCCCTTCTACTCACCATGTCCTTGATTCCGCTGACTTCTCTTTCTCCCCTTCTCATGAC

CTAAACTTTGAATTTTCCGGCAAGTGGGTCACCGATATCCTCCTTGAATCTGCACATGCCATCGCGGATA

AAAACAGCGCTCGTCTCCAGCAATTGATGTGGATGCTTAATGAGCTTGGTTCACCTTATGGTGACACAGA

GCAAAAACTTGCTTCTTATTTTCTCCAAGCTTTGTTTAGCCGCATGAACGACTCCGGCGAGAGATGCTAC

CGTACTTTAGCTTCAGCATCAGAGAAAACTTGCTCTTTTGATTCCACAAGGAAATGGTATTAAAGTTTC

AAGAGGTGAGTCCTTGGACTACTTTTGGTCACGTATCTTGTAATGGCGCAATTATGGAAGCATTTGAAGG

TGAAAGCAAATTGCATATTATTGATATTAGTAACACATATTGTACCCAATGGCCTACTTTGCTCGAAGCC

CTAGCAACTCGCACTGATGAGACACCACACTTGAAGTTAACCACCGTAGTGGCTAGCAAAAGTAGTGGTA

ATAATATTGGTTTAACTAGTACAGGAGGTTTAGCTTCAGTTCATAAGGTAATGAAAGAAATTGGCAACAG

-continued

```
AATGGAAAAATTTGCCAGGCTTATGGGAGTCCCATTTAAGTTTAATGTTATCCACCATGCTGGTGATTTA
TGTGACCTAAACTTAGCTGAATTGGATGTTAAAGATGATGAGGCTCTTGCTATCAACTGTGTTGGTGCTT
TACACTCAATCACTCCAGCTTCTCGTCGCCGAGATTATGTTATATCTAGTTTTAGAACATTGCAACCAAG
AATCATTACTGTTGTTGAAGAAGAAGCTGATCTTGATGGTCTGGATTTTGTCAAGGGTTTTCAAGAATGT
TTAAGATGGTTTAGGGTTTACTTTGAATCATTGGATGAGAGCTTTCCAAGAACCAGTAACGAACAGTTGA
TGCTTGAAAGAGCAGCAGGCCGCGCTATCGTTGACTTAGTGGCATGTCCTCCATCTGATTCGATCGAAAG
GCGGGAAACAGCCACGCGCTGGTCTGGACGCCTCCATTCATGTGGTTTTAGCCCGATAATTTTCAGTGAT
GAGGTTTGTGATGATGTACGCGCCTTATTGAGGAGGTATAAGGAGGGTTGGTCAATGACACAGTGCGGGG
ATGCCGGAATATTCTTGTGCTGGAAGGAACAGCCGGTGGTGTGGGCTAGTGCATGGAGGCCCTGATTGAG
ATTGGTGATGGTTTTCACTTTTCACTTTTCTTTTCTTTCTTTTTTCTTTTGTTTTTGCTTTTCTCCTTGT
ATTTTTTTTTTTCAAAGTTAGTTTGAGTGATTGGCACGTTTGATGTGTTTATTTGGGCACGTGCATGGA
TTAAGGATTGGAATAGTAAATGAAGTTAATCAATTTTCATTGATCTTTGTTTAATTATCATTTGCGGTTA
TTTCTTATTTTTATGAAAAATAGCTTTCTTAATCATCATATCAAAGAAACGTTTTTAATTCAATGATGTA
AACAAATTAGTTGAGCAAGATTTATCTTTGGGGTAAATAAATGATTTAATTTAGGAAAGTTATTCGATAA
TTA
```

PtSHR1 eugene3.01860017
(SEQ ID NO: 2)

```
MDTLFRLVSLQQQSEQSFNSTSRTSSSSRSSRQNNNHHHHHYQQEDEECFNFFMDEEDFSSSSSKHYYPPYHHNQ
QQQHQHQTTTTTPTTTTTNTSTPSTHHVLDSADFSFSPSHDLNFEFSGKWVTDILLESAHAIADKNSARLQQLMW
MLNELGSPYGDTEQKLASYFLQALFSRMNDSGERCYRTLASASEKTCSFDSTRKMVLKFQEVSPWTTFGHVSCNG
AIMEAFEGESKLHIIDISNTYCTQWPTLLEALATRTDETPHLKLTTVVASKSSGNNIGLTSTGGLASVHKVMKEI
GNRMEKFARLMGVPFKFNVIHHAGDLCDLNLAELDVKDDEALAINCVGALHSITPASRRRDYVISSFRTLQPRII
TVVEEEADLDGLDFVKGFQECLRWFRVYFESLDESFPRTSNEQLMLERAAGRAIVDLVACPPSDSIERRETATRW
SGRLHSCGFSPIIFSDEVCDDVRALLRRYKEGWSMTQCGDAGIFLCWKEQPVVWASAWRP
```

PtSHR2A eugene3.00070144
(SEQ ID NO: 3)

```
AAGTCCTCGCCACTTATATGTGTTTATTGAGAAAAAAATATATATTATACATGTAGTACGTACGTATGA
TATGCAATATCGAACAAGTATATACTAGCTAGGGCTTTGAGGTTATTGCAATTATGGTTGCCAAATCCAA
CCACTACACTAGCAATTAGGTATTTTTCATCTCGAGATCACAATATCATTAATTTGAAGCTAATAATACA
CATAAAAATAGAAATTCATATTAAGAAAAAATATATATATATAGCATGACTATGACCCCCAAACCCCAAA
ATATAATACTACGGATTTCTATATCATAGCTTTGTACTTGGCCAATTTTTTTGAATTAGCAGAGGTACTG
CCTCCAGAGTCAAAGGGGGCCTTCCCTAGCTATCACCCACGGACATAACCATCTTCGGTCCAAAAGACAG
ACTCACACACTTATTTCCTTCCCACCAACAAAGCAATGATCAAATAGAAGCTAGCTATAGACATGCAAAG
CAATAGCAGCAACAACAACAACAATCAGCCTCAGACTAGTCATACATCAACAAGCCGTTCTTCGGACTCC
GGTGAGGCTTGTGGGGCAGGAAACAAATGGGCATCAAGGCTTCTTAGTGAGTGTGCAAGAGCAATCTCAG
AGAAGGACTCTAGCAAGATCCATAACCTTCTATGGATGTTAAATGAGCTTGCCTCTCCTTATGGAGATTG
TGAACAGAAATTGGCATCTCATTTCTTGCAAGCTCTCTTTTGTAAGGCTACCGACTCCGGCCAACGGTGC
TTCAAAACCCTAACAACAGTAGCTGAAAAGAGCCACTCCTTTGATTCAGCTAGGAAATTGATACTAAAAT
TCCAAGAGGTAAGCCCATGGACTACTTTTGGTCATGTGGCTTCAAACGGTGCAATTTTGGAGGCCTTAGA
TGGGGCGAGCAAACTTCACATAATTGATATAAGCCATACCCTTTGCACACAATGGCCTACTTTGCTAGAA
GCTTTAGCTACAAGAAATGATGAGACGCCGCATTTAAAGCTCACCGTTGTGGTAACTGCTAGCATTGTAA
GATCGGTCATGAAAGAAATTGGCCAAAGAATGGAGAAGTTTGCTAGGTTAATGGGAGTGCCCTTTGAGCT
```

-continued

```
TAATGTAATTAGTGGGCTAAACCATTTAGGAGAGCTCACAAAGGACAGGCTAGGAGTTCAAGAAGATGAA

GCTGTCGCGATTAATTGCAATGGGGCATTGAGAAGAGTTGGAGTAGAGGAAAGAAATTCTGTGATCCAGA

TGTTTCAATCACTTAACCCTCGAGTTGTGACAATTGTTGAAGAAGAAGCTGATTTTACTAGCTCAAGATA

TGACTTTGTCAAGTGCTTTGAAGAGTGCCTTAGGTATTATACACTATATTTTGAGATGCTAGAGGAGAGC

TTTGTCCCAACTAGTAATGAGAGATTGATGTTGGAGAGGGAATGTTCAAGGAACATAGTTAGAGTTTTGG

CTTGTGATGAAGGAAATGATGGAGGAGAGTGTGAAAGAAGGGAGAGGGGAAGCCAATGGTTTGAAAGGCT

AAGGGAGGCATTTTCCCCTGTTGGGTTCAGTGATGATGTTGTCGATGATGTCAAGGCATTGCTTAAGAGA

TACCGAGCTGGGTGGGCACTAGTGCTACCTCAAGGAGATCATGACTCAGGAATTTACTTAACATGGAAAG

AAGAACCTGTGGTATGGGCTTCTGCATGGAAACCCTAGAGGAGAATTATAGCTAGAACACCATGATCTCC

ACACTCAAAGTCAAGGCTTAGCATGGCAATTTATTCACAATTTGGGAAGCACTGCCATGAACACAACATA

TTGATTCCTGTCAATCATGAAGTACTACTACTTTCACTTTTCATTTCTTCTTCTCATTCATGCATATTTG

TGTCTTCTGTACTCCAACTTTTCTTTTCTTATGCT
```

PtSHR2A eugene3.00070144

(SEQ ID NO: 4)

```
MQSNSSNNNNNQPQTSHTSTSRSSDSGEACGAGNKWASRLLSECARAISEKDSSKIHNLLWMLNELASPYGDCEQ

KLASHFLQALFCKATDSGQRCFKTLTTVAEKSHSFDSARKLILKFQEVSPWTTFGHVASNGAILEALDGASKLHI

IDISHTLCTQWPTLLEALATRNDETPHLKLTVVVTASIVRSVMKEIGQRMEKFARLMGVPFELNVISGLNHLGEL

TKDRLGVQEDEAVAINCNGALRRVGVEERNSVIQMFQSLNPRVVTIVEEEADFTSSRYDFVKCFEECLRYYTLYF

EMLEESFVPTSNERLMLERECSRNIVRVLACDEGNDGGECERRERGSQWFERLREAFSPVGFSDDVVDDVKALLK

RYRAGWALVLPQGDHDSGIYLTWKEEPVVWASAWKP
```

PtSHR 2B eugene3.00640143

(SEQ ID NO: 5)

```
ACATATAAGAATATTTCAAATATAATACACAAGAAATTATTCACATTAACAAAATAGGATGACTATGACC

CCCCACCCCAAGATATAATTATACTATGGATATCTATATCAATATAGCTTTGTACTTGGCCATGTCTGAA

CTCAAATGAAATTTGAGTTTGGCAAAGGTTCTGCCTCTAGAGTCAAAGGGGGCCTCGCCGATCACCAATG

GACATAACTCTCTTCAGTCCAAAAGACACACTGACACACTTCTTTCCTTCCCACCAGCAAAGCAATGATC

AAGTAGCAGCTATAGACATGCAAAGCAATAGCAGCAACAACAACAATAATCAGCCTCAAACCAGCCATAC

ATCAACAAGCCGGTCTTCGGACTCCGGTGAGGCCTGTGGAGGAGGAAACAAGTGGGCATCAAAGCTTCTT

AGTGAGTGTGCAAGAGCAATCTCAGAGAAGGACTCTAGCAAGATCCACCACCTTCTATGGATGTTAAATG

AGCTTGCCTCTCCTTATGGAGATTGTGATCAGAAATTGGCATCTTATTTCTTGCAAGCTCTATTCTGTAA

GGCTACCGAGTCTGGTCAACGGTGTTTCAAAACCCTAACAACAGTAGCTGAAAAGAGCCACTCCTTTGAT

TCAGCTAGGAAATTGATACTAAAATTCCAAGAGGTAAGCCCGTGGACTACTTTCGGTCATGTAGCTTCAA

ATGGTGCAATTTTGGAGGCCTTAGATGGGAAAGCAAACTTCACATAATTGATATCAGCAATACCCTTTG

CACACAGTGGCCTACTTTGCTAGAAGCTTTAGCCACAAGAAATGATGAGACGCCGCGATTAAAGCTCACC

GTTGTGGTAACTGCTAGCATTGTAAGATCAGTCATGAAAGAAATTGGCCAAAGAATGGAGAAGTTTGCTA

GGTTAATGGGAGTGCCCTTTGAGTTTAAAGTAATTAGTGTGCTAAATCATATAGGAGAGCTCACAAAGGA

AGGACTGGGTGTTCAAGAAGATGAAGCAGTCGCGATTAATTGCATTGGGGCATTGAGAAGAGTTGAAGTA

GATGAAAGAAGTTCTGTAATCCAGTTGTTCCGATCACTTAACCCTCGAGTTGTGACAATTGTAGAGGAAG

AAGCTGATTTTACTAGCTCAAGATATGACTTCGTCAAGTGCTTTGAAGAGTGCCTGAGGTATTATACACT

ATATTTTGAGATGCTAGAGGAGAGCTTTGTCCCAACTAGTAATGAGAGATTGATGTTGGAGAGGGAATGT

TCAAGGAACATAGTTAGGGTTTTGGCTTGTGATGAAGAAACTGGTGGAGGAGAGTGTGAAAGAAGAGAGC

GGGGTGTCCAATGGTCTGAAAGGCTAAGGGAGGCATTTTCCCCTGTTGGATTCAGTGATGATGTTGTCGA

TGATGTCAAGGCATTGCTTAAGAGATACAAAGCTGGGTGGGCACTTGTGCTACCTCAAGGAGATCATGAG
```

-continued

TCAGGAATTTACCTAACATGGAAAGAGGAACCTGTAGTATGGGCTTCTGCATGGAAACCCTAAAAGGTTG

TGGCCAGAACACCATCTCTATGCTCAAATTCAAGGCTCAGCATGGCAATTTATTCACAAGATGGGAACAG

CGCGCCATGAACACATATTGATAATTAATTATAGAGTACTACTACTTTCACTTTTCATTTCTTCTTCTTA

TTCATGCATATTTGTATCTTATGCACTCCAACTTTTCTTTTCTTATGTTATAT

PtSHR2B eugene3.00640143

(SEQ ID NO: 6)

MQSNSSNNNNNQPQTSHTSTSRSSDSGEACGGGNKWASKLLSECARAISEKDSSKIHHLLWMLNELASPYGDCDQ
KLASYFLQALFCKATESGQRCFKTLTTVAEKSHSFDSARKLILKFQEVSPWTTFGHVASNGAILEALDGESKLHI
IDISNTLCTQWPTLLEALATRNDETPRLKLTVVVTASIVRSVMKEIGQRMEKFARLMGVPFEFKVISVLNHIGEL
TKEGLGVQEDEAVAINCIGALRRVEVDERSSVIQLFRSLNPRVVTIVEEEADFTSSRYDFVKCFEECLRYYTLYF
EMLEESFVPTSNERLMLERECSRNIVRVLACDEETGGGECERRERGVQWSERLREAFSPVGFSDDVVDDVKALLK
RYKAGWALVLPQGDHESGIYLTWKEEPVVWASAWKP

AtSHR At4g37650

(SEQ ID NO: 7)

ATGGATACTC TCTTTAGACT AGTCAGTCTC CAACAACAAC AACAATCCGA TAGTATCATT

ACAAATCAAT CTTCGTTAAG CAGAACTTCC ACCACCACTA CTGGCTCTCC ACAAACTGCT

TATCACTACA ACTTTCCACA AAACGACGTC GTCGAAGAAT GCTTCAACTT TTTCATGGAT

GAAGAAGACC TTTCCTCTTC TTCTTCTCAC CACAACCATC ACAACCACAA CAATCCTAAT

ACTTACTACT CTCCTTTCAC TACTCCCACC CAATACCATC CCGCCACATC ATCAACCCCT

TCCTCCACCG CCGCAGCCGC AGCTTTAGCC TCGCCTTACT CCTCCTCCGG CCACCATAAT

GACCCTTCCG CGTTCTCCAT ACCTCAAACT CCTCCGTCCT TCGACTTCTC AGCCAATGCC

AAGTGGGCAG ACTCGGTCCT TCTTGAAGCG GCACGTGCCT TCTCCGACAA AGACACTGCA

CGTGCGCAAC AAATCCTATG ACGCTCAAC GAGCTCTCTT CTCCGTACGG AGACACCGAG

CAAAAACTGG CTTCTTACTT CCTCCAAGCT CTCTTCAACC GCATGACCGG TTCAGGCGAA

CGATGCTACC GAACCATGGT AACAGCTGCA GCCACAGAGA AGACTTGCTC CTTCGAGTCA

ACGCGAAAAA CTGTACTAAA GTTCCAAGAA GTTAGCCCCT GGGCCACGTT TGGACACGTG

GCGGCAAACG GAGCAATCTT GGAAGCAGTA GACGGAGAGG CAAAGATCCA CATCGTTGAC

ATAAGCTCCA CGTTTTGCAC TCAATGGCCG ACTCTTCTAG AAGCTTTAGC CACAAGATCA

GACGACACGC CTCACCTAAG GCTAACCACA GTTGTCGTGG CCAACAAGTT TGTCAACGAT

CAAACGGCGT CGCATCGGAT GATGAAAGAG ATCGGAAACC GAATGGAGAA ATTCGCTAGG

CTTATGGGAG TTCCTTTCAA ATTTAACATT ATTCATCACG TTGGAGATTT ATCTGAGTTT

GATCTCAACA AACTCGACGT TAAACCAGAC GAAGTCTTGG CCATTAACTG CGTAGGCGCG

ATGCATGGGA TCGCTTCACG TGGAAGCCCT AGAGACGCTG TGATATCGAG TTTCCGACGG

TTAAGACCGA GGATTGTGAC GGTCGTAGAA GAAGAAGCTG ATCTTGTCGG AGAAGAAGAA

GGTGGCTTTG ATGATGAGTT CTTGAGAGGG TTTGGAGAAT GTTTACGATG GTTTAGGGTT

TGCTTCGAGT CATGGGAAGA GAGTTTTCCA AGGACGAGCA ACGAGAGGTT GATGCTAGAG

CGTGCAGCGG GACGTGCGAT CGTTGATCTT GTGGCTTGTG AGCCGTCGGA TTCCACGGAG

AGGCGAGAGA CAGCGAGGAA GTGGTCGAGG AGGATGAGGA ATAGTGGGTT TGGAGCGGTG

GGGTATAGTG ATGAGGTGGC GGATGATGTC AGAGCTTTGT TGAGGAGATA TAAGAAGGT

GTTTGGTCGA TGGTACAGTG TCCTGATGCC GCCGGAATAT TCCTTTGTTG GAGAGATCAG

CCGGTGGTTT GGGCTAGTGC GTGGCGGCCA ACGTAA

AtSHR At4g37650

(SEQ ID NO: 8)

MDTLFRLVSLQQQQQSDSIITNQSSLSRTSTTTTGSPQTAYHYNFPQNDVVEECFNFFMDEEDLSSSSSHHNHHN
HNNPNTYYSPFTTPTQYHPATSSTPSSTAAAAALASPYSSSGHHNDPSAFSIPQTPPSFDFSANAKWADSVLLEA
ARAFSDKDTARAQQILWTLNELSSPYGDTEQKLASYFLQALFNRMTGSGERCYRTMVTAAATEKTCSFESTRKTV
LKFQEVSPWATFGHVAANGAILEAVDGEAKIHIVDISSTFCTQWPLLEALATRSDDTPHLRLTTVVVANKFVNDQ
TASHRMMKEIGNRMEKFARLMGVPFKFNIIHHVGDLSEFDLNELDVKPDEVLAINCVGAMHGIASRGSPRDAVIS
SFRRLRPRIVTVVEEEADLVGEEEGGFDDEFLRGFGECLRWFRVCFESWEESFPRTSNERLMLERAAGRAIVDLV
ACEPSDSTERRETARKWSRRMRNSGFGAVGYSDEVADDVRALLRRYKEGVWSMVQCPDAAGIFLCWRDQPVVWAS
AWRPT

Rice SHR nucleotide sequence (SEQ ID NO: 9)

TGCAGGATTCGGCACGAGGCACAACTAGCTAGTTTAGATCCCCTTTGCATCCATCGATGATCAGTTGTTGCATCGATGAT
CAGTTGTTGCAGGACAGTGTAGTGAGGTGAGAAAGATTGTTGTAGTAGCTGCTGTGCTGTATGGTGGTAGCCAGTGAGTA
GCTACTACACTGCACTGCAGTTTGCACCCCGGCCATATGTTGGCTACTACTACTGCAGGTGTCTTAGGTCTAGATGGATA
CCCTCTTCAGGTTGGTTAGCCTCCACCACCATCACCACCACCAGCACGCGGCCTCACCGTCGCCGCCGGACCAGCCGCAC
AAGTCGTACCCCTCCTCGCGAGGGAGCACCAGCTCCCCCTCCTCCCACCACACCCACAACCACACCTACTACCACCACTC
CCACTCCCACTACAACAATAATAGCAACACCAACTACTATTACCAGGGTGGTGGAGGCGGCGGCGGAGGGTACTACTACG
CGGAGGAGCAGCAGCCGGCGGCGTACCTAGAAGAATGCGGCAACGGCCACCAGTTTTACATGGATGAAGACTTCTCCTCC
TCGTCTTCCTCCCGCCAGTTCCACTCGGGAACGGGCGCGCCGTCGTCGGCGCCGGTGCCTCCTCCTCCGTCGGCGACGAC
GTCGTCCGCGGGCGGGCACGGGCTGTTTGAGGCGGCGGACTTCTCGTTCCCGCAGGTTGATATCAGCCTCGACTTCGGCG
GCTCTCCGGCCGTTCCGTCGTCGTCCGGTGCTGGCGCCGGCGCCGGGGCAGCGCCGTCGTCGTCGGGGAGGTGGGCGGCG
CAGCTGCTGATGGAGTGCGCGCGCGCGGTGGCGGGGCGCGACAGCCAGCGCGTGCAGCAGCTCATGTGGATGCTCAACGA
GCTGGCCTCGCCGTACGGCGACGTCGACCAGAAGCTGGCCTCCTACTTCCTGCAGGGCCTCTTCGCGCGGCTCACCACCT
CCGGCCCGCGCACGCTGCGGACGCTCGCCACCGCGTCGGACCGGAACGCGTCGTTCGACTCCACGCGCCGCACGGCGCTC
AAGTTCCAGGAGCTCAGCCCGTGGACGCCGTTCGGGCACGTCGCCGCCAACGGCGCCATACTCGAGTCGTTCCTGGAGGC
CGCGGCGGCGGGCGCCGCCGCCTCCTCCTCCTCGTCGTCTTCATCGTCGACGCCGCCGACGCGGCTGCACATCCTCGACC
TGAGCAACACGTTCTGCACGCAGTGGCCGACCCTCCTGGAGGCGCTGGCCACCCGGTCCTCGGACGACACGCCGCACCTG
TCCATCACCACCGTCGTGCCCACGGCGGCGCCGTCGGCGGCCGCGCAGCGCGTGATGCGGGAGATCGGGCAGCGCCTCGA
GAAGTTCGCGCGGCTGATGGGCGTCCCGTTCAGCTTCCGCGCCGTGCACCACTCGGGGGACCTGGCCGACCTCGACCTCG
CCGCGCTGGACCTCCGCGAGGGCGGCGCCACCGCCGCGCTCGCCGTCAACTGCGTAAACGCGCTGCGCGGGGTCGCGCGG
GGGCGCGACGCGTTCGTGGCGTCGCTCCGGCGCCTGGAGCCGCGCGTGGTCACCGTCGTGGAGGAGGAGGCCGACCTGGC
GGCGCCGGAGGCGGACGCGTCGTCGGAGGCCGACACCGACGCCGCGTTCGTCAAGGTGTTCGGCGAGGGCCTCCGCTTCT
TCTCGGCGTACATGGACTCGCTGGAGGAGAGCTTCCCCAAGACAAGCAACGAGAGGCTGTCACTGGAGAGGGCGGTCGGC
CGTGCCATCGTCGACCTCGTGTCATGCCCGGCCTCCCAGTCCGCCGAGCGCCGGGAGACCGCCGCGTCGTGGGCGCGGCG
CATGCGGTCGGCGGGGTTCTCGCCGGCGGCATTCAGCGAGGACGTCGCCGACGACGTGCGGTCGCTTCTCCGGCGGTACA
AGGAGGGCTGGTCGATGCGGGACGCCGGCGGTGCCACGGACGACGCCGCCGGCGCCGCTGCTGCCGGAGCGTTCCTTGCG
TGGAAGGAGCAGCCTGTCGTGTGGGCGAGCGCGTGGAAGCCATGAGATCGATCGATCCAACAAGTCCAAATCCGCCATTG
CTGCAAATCATCGAGCCTGCGATGCATCGTGCATGCAATACACAATATGGATCATGCATATCGCACGTGCGGGTTGAATG
GGAAGAGGAAGCAGCGCGCGCGTGTACGTACTTAGGGTTTTTCAGCCAGCAACGTACGTGTGTAGTAGGGAGAGGAGGTA
GCAAAACACATCAGATGGATTAAGTTAATCAATCACCAGTTATTACTAGAAAATTAATTTGGAGGAATTAATTGGCATTT
ATTGTTCTTGCATAACATGTTTATTAATTATTAGATGCTTCCTCTGATTATTAACTTTGTGAATTCAGGTGTGTTCAATT

-continued

TAATTTTAGCTAGCTAGTAGATATATCGATCCTCAGGTGATTTATTTGTAGATCTGAATATTCCATGACTTGTATAGGAG

CTACTAATAGTTTATTTGTTTTACCGGTT

Rice SHR AAS07303.1 GI: 41469537

(SEQ ID NO: 10)

MDTLFRLVSL HHHHHHQHAA SPSPPDQPHK SYPSSRGSTS SPSSHHTHNH TYYHHSHSHY

NNNSNTNYYY QGGGGGGGGY YYAEEQQPAA YLEECGNGHQ FYMDEDFSSS SSSRQFHSGT

GAPSSAPVPP PPSATTSSAG GHGLFEAADF SFPQVDISLD FGGSPAVPSS SGAGAGAGAA

PSSSGRWAAQ LLMECARAVA GRDSQRVQQL MWMLNELASP YGDVDQKLAS YFLQGLFARL

TTSGPRTLRT LATASDRNAS FDSTRRTALK FQELSPWTPF GHVAANGAIL ESFLEAAAAG

AAASSSSSSS SSTPPTRLHI LDLSNTFCTQ WPTLLEALAT RSSDDTPHLS ITTVVPTAAP

SAAAQRVMRE IGQRLEKFAR LMGVPFSFRA VHHSGDLADL DLAALDLREG GATAALAVNC

VNALRGVARG RDAFVASLRR LEPRVVTVVE EEADLAAPEA DASSEADTDA AFVKVFGEGL

RFFSAYMDSL EESFPKTSNE RLSLERAVGR AIVDLVSCPA SQSAERRETA ASWARRMRSA

GFSPAAFSED VADDVRSLLR RYKEGWSMRD AGGATDDAAG AAAAGAFLAW KEQPVVWASA

WKP

Rice SHR nucleotide sequence (SEQ ID NO: 11)

ATGGAGAAAGCAAGCAAAGCAAAGGCAGAGGCAGCAAAAGGCGCCCACACCCACTGCCGCTGCCTGCTGCTGCTGCCCCC

GATGGATACGCTGTTTAGGTTGGTTAGCCTCCAAGCCGCCTCCGAGCAGCAGCAGCAGCAGCAGTCGGCGTCCTACA

ACTCGAGGAGCACGACGTCGAGCGGGTCCAGGTCGTCGTCGCACCAGACGAACGCGTCCTACAGCTACTACCACCACAGC

AGCAACAGCGGCGGCGGCGGCGGAGGCGGCGGAGGGTACTACTACGGCGGCCAGCAGCCGCCGCCGTCGCAGTACTACTA

CCTGGAGCCGTACCAAGAAGAATGCGGCAACGCCCCACACCACCAGCTTTACATGGATGAAGACTTCTCCTCCTCGTCGT

CGTCGAGGCACTTCCACCACGGCGCGGGTGCAGCAGCAGCAGCCGCCGGCGTCGTCCACGCCCACGGGGACGGCGCCG

ACGCCGCCGCTGTCGACCTCGTCCACCGCGGCGGGCGCCGGGCACGGCCTGTTCGAGGCGGCGGACCTGTCGTTCCCGCC

GGACCTCAACCTCGACTTCTCGTCCCCGGCGTCGTCGTCCGGCGGCGGGACAGCGTCGTCGGGCGCGGTTGGGGGCGGCG

GCGGCGGGAGGTGGGCTAGCCAGCTGCTGCTGGAGTGCGCGCGGTCGGTGGCCGCCCGCGACAGCCAGCGCGTGCAGCAG

CTCATGTGGATGCTCAACGAGCTCGCGTCGCCGTACGGCGACGTGGAGCAGAAGCTGGCTTCCTACTTCTTGCAGGGGCT

GTTCGCTCGGCTCACGGCGTCCGGGCCGCGCACGCTGCGCACGCTCGCCGCGGCGTCCGACCGGAACACGTCGTTCGACT

CGACGCGGCGCACGGCGCTGCGGTTCCAGGAGCTCAGCCCCTGGTCCTCGTTTGGGCACGTCGCCGCCAATGGCGCCATC

CTCGAGTCCTTCCTGGAGGTCGCCGCCGCGGCGTCGTCGGAGACGCAGCGGTTCCACATCCTCGACCTGAGCAACACGTT

CTGCACGCAGTGGCCGACGCTGCTGGAGGCGCTGGCCACGCGGTCCGCCGACGAGACGCCGCACCTCTCGATCACCACCG

TGGTGTCCGCCGCGCCGTCCGCGCCCACGGCGGCGGTGCAGCGCGTCATGCGGGAGATCGGGCAGCGCATGGAGAAGTTC

GCGCGGCTCATGGGCGTGCCCTTCCGCTTCCGCGCCGTGCACCACTCCGGGGACCTCGCGGAGCTCGACCTCGACGCGCT

CGACCTCCGCGAGGGCGGCGCCACCACCGCGCTCGCCGTCAACTGCGTCAACTCGCTGCGCGGCGTGGTTCCCGGCAGGG

CCCGCCGGCGCGACGCGTTCGCGGCGTCGCTCCGCCGGCTGGACCCGCGGGTCGTCACCGTCGTCGAGGAGGAGGCGGAC

CTGGTGGCGTCCGATCCCGACGCGTCGTCGGCGACGGAGGAAGGCGGCGACACGGAGGCGGCGTTCCTCAAGGTGTTCGG

CGAGGGCTTGCGCTTCTTCTCGGCGTACATGGATTCGCTCGAGGAGAGCTTCCCCAAGACGAGCAACGAGAGGCTGGCAT

TGGAGAGGGGAGCAGGGCGCGCCATCGTCGACTTGGTCTCGTGCCCGGCGTCGGAGTCGATGGAGCGGCGGGAGACGGCG

GCGTCGTGGGCGCGGCGCATGCGGTCGGCCGGGTTCTCTCCGGTGGCATTCAGCGAGGACGTCGCCGACGACGTGCGATC

GCTGCTGCGCCGGTACAGGGAAGGGTGGTCGATGCGCGAGGCCGGCACGGACGACTCGGCGGCCGGAGCCGGCGTCTTCC

TCGCGTGGAAGGAGCAGCCTCTGGTGTGGGCAAGCGCGTGGCGGCCATGATCGGATCGTCGTGATCGATGGATCAAAGCT

CACCGGTGAGTGGAACAGCATGGAAGAAAAGAGCTCCATAGCTAAGCAAGCACGCATGCATATCCACCATGCATGGGGTA

AGCTAGCAAGCTCTCTCGTGTGTGTCACGATCGACATTAATGGCGGCTCACACAAAGGCATGTAGGGTTTTGAAACAGCG

-continued

```
TAGGAAGCTACAGAAATGGATCACGTACGTACGTACACATTGGGTTGCAGCGATCGAGGAGGGAGATGATAGTTTTAGTT
CCTAGATTTGCATCCATTTTTATTCATCGATCGCCAACAAGTTCTTGGCGAGAAGATGATTTTGATTTGCTTGCTTCCAT
CTTCTTGTTTATTTTTCCCCCTTTCGTTTGTGTTTCTTCTTAATTTGTAAGGGTTAACGACATTTTTCTTCACTCTGGAG
AAATTTTACGTGCATGGTTTTTATCATGCGTACCCGCAA
```

Rice SHR BAD30442.1 GI: 50509213

(SEQ ID NO: 12)

```
MEKASKAKAE AAKGAHTHCR CLLLLPPMDT LFRLVSLQAA SEQQQQQQQS ASYNSRSTTS
SGSRSSSHQT NASYSYYHHS SNSGGGGGGG GGYYYGGQQP PPSQYYYLEP YQEECGNAPH
HQLYMDEDFS SSSSSRHFHH GARVQQQQPP ASSTPTGTAP TPPLSTSSTA AGAGHGLFEA
ADLSFPPDLN LDFSSPASSS GGGTASSGAV GGGGGGRWAS QLLLECARSV AARDSQRVQQ
LMWMLNELAS PYGDVEQKLA SYFLQGLFAR LTASGPRTLR TLAAASDRNT SFDSTRRTAL
RFQELSPWSS FGHVAANGAI LESFLEVAAA ASSETQRFHI LDLSNTFCTQ WPTLLEALAT
RSADETPHLS ITTVVSAAPS APTAAVQRVM REIGQRMEKF ARLMGVPFRF RAVHHSGDLA
ELDLDALDLR EGGATTALAV NCVNSLRGVV PGRARRRDAF AASLRRLDPR VVTVVEEEAD
LVASDPDASS ATEEGGDTEA AFLKVFGEGL RFFSAYMDSL EESFPKTSNE RLALERGAGR
AIVDLVSCPA SESMERRETA ASWARRMRSA GFSPVAFSED VADDVRSLLR RYREGWSMRE
AGTDDDSAAGA GVFLAWKEQP LVWASAWRP
```

Barley SHR nucleotide sequence (SEQ ID NO: 13)

```
ATTCGGCACGAGGCCCAGCCCCCCTACAGGAAACAGCATCGCACTCCCCCACCACAACCTCAGAGGCCACCAACACAC
ACACGCACCTCTTCCCCTCTCCCTTCGCGATCTCTCTTCTCGCCGTCGCCGCACGAATCCTCCTCGCCTCGACTCCAGCT
CAAGGGTCCGACGTACGTACGGCGAGCCACCGGCCGGAGCTACTGCGCAGAGATTTTCGTTCCATCTGGATTTCTGGGCT
AGAAGAAAGATCCATGCAGTGATTAGCGTGTCAAGAATCTCTACTGAACAAGTATGGCCGATACTCCGACTTCCCGGATG
ATCCACCCCTTCAGCAACATGCAGAGGCAGAACCCGAAGCAGTTCCAGTTCCAGTACCCGGACAACCCACAGCATCCCTG
CCACCCTTACCAGCCATCTCCAGACACCCACGTCGTGCCACAGCATCACTACAGCCTCAAGTCTCACTCGTCAGATGCTA
GCTACGAGAACCATGTTGCTCAGATGAAGCACACTCTGGTGGACTCCTCGGCCGCGGCCGGCTGCATGAGGCACGACTCG
CCCTCCAGCCATAGCTTCACTCCTCCGTCCATCAGGAGCGGCAGTGGCAGCCCTTCGTCTCACGACGACAGCCACTCCGA
CTCCACGGACGGGTCTCCTGTCAGTGCTTCATGCGTCACTGTGACGACCGAGGATCCTAACGATCTGAAGCAGAAGCTCA
AGGACCTCGAGGCTGAGATGCTTGGGCCAGACGCCGCTGAGATAGTTAACAGCCTCGAGAGCTCGGTGGCGAAGCAGCTC
TCGCTGGAGCCGGAGAAGTGGGCGCAGATGATGGACTTTCCCAGGGGCAACCTCAAGGAGCTGCTGCTTGCTTGTGCCAG
AGCTGTGGAAGAGAAGAACATGTACGCGGTCGACGTGATGGTGCCGGAGCTGAGGAAGATGGTTTCGGTCTCCGGTACGC
CGCTCGAGAGGCTGGGAGCCTACATGGTGGAAGGGCTCGTCGCCAGGCTCGCCTCCTCCGGCCACTCCATCTACAAGGCC
TTGAGGTGCAAGGAGCCCAAGAGCTCCGACCTGCTGTCCTACATGCATTTCCTGTACGAGGCCTGCCCCTACTTCAAGTT
CGGCTACATGTCGGCCAACGGCGCCATCGCGGAGGCCGTCAAGGGGAGGACAGGATCCACATAATCGACTTCCATATCG
CTCAAGGAGCTCAGTGGATCTCCCTCCTCCAGGCCCTTGCGGCCAGGCCCGGCGGACCGCCGACCGTGAGGATCACCGGC
ATTGATGACTCGGTGTCAGCCTACGCGCGAGGCGGCGGGCTGGACCTCGTTGGGAGGAGACTGTCGCACATCGCCGGCCT
CTGCAAGGTTCCCTTTGAGTTCCGCTCGGTCGCCATGGCCGGCGAGGAGGTGGAGGAGGGGCACCTCGGGGTGGTCCCCG
GGGAGGCACTGGCGGTGAACTTCACCCTGGAGCTGCACCACATCCCGGACGAGACGGTGAGCACGGCGAACCACCGGGAC
CGGATCCTGCGGCTGGTGAAGGGGCTGAGGGCCCAAGGTGCTGACCCTGGTGGAGCAGGAGTCCAACACCAACACGGCCCC
GTTCCCGCAGAGGTTCGCCGAGACGCTGGACTACTACACGGCCATCTTCGAGTCCATCGACCTCACGCTGCCCAGGGACG
ACAGGGAGCGGGTCAACATGGAGCAGCACTGCCTGGCGAGGGAGGTGGTGAACCTGATCGCGTGCGAGGGCGCGGAGCGG
GTGGAGCGACACGAGGTGTTCGGCAAGTGGAAGGCGCGCCTCACCATGGCCGGCTTCAGGCCCTCGCCGCTCAGCTCGCT
```

-continued

GGTCAACGCCACCATCAGCAAGCTGCTGCAGAGCTACTCCGACAACTACAAGCTCGCCGAGAGGGACGGGGCGCTCTACC
TCGGCTGGAAGAAGAGGCCCCTCGTGGTCTCGTCCGCCTGGCACTAGCGCTGCGGTCGTCATATCATGGCCAACTGCTTT
GTGACCATGCTTTTCGTAGGCGAATCTAGATGCATGCTTAATGCTTTGCTGGACTATAGGGGTGTCCTGCTGATGCTGTT
GCTGCTGCTGCTGTGGAGAAGAATAGCTCCTGTAACCTGTTGTTGTAATGCCGAACTTAGGTCTAAAAGCCTGAATA
TGGCTGATGAGATGTAGTGTAAGTTTTTACCGTATATGTTTCAGTTTTATGTTTCAGTTTCAGACTTCTAATCGTAATCT
TGTTGTCTAATCAAAAAAAAAAAAAAAAAAATCTGGGGGGGGGGCCCGGTACCCCAATCGCCCTTTATGGGGATCGTAT
TTACGGCCGCTTATGGCCGTTTTTTTAAAAAGTTGGGATTGGGAAAAACCCTGGGGTTACCCAAATTTAAATCCCTTTGG
GGAGANNNNGNGNCGNNGGGTTTCCCACCACGCAGACGGGTAAAAAACATGGGCGGTCACCCAATAATCTATGTGTTCTC
TGAGATGCAACCGATACGTCAAAGCACNGATTTAATAACTGATATTTCACGTCATTCATTAATACCCTCGTGTACAGCAG
TATAATGAAACTAACGATGTAGCGTTTGAGAGTTTAGTCTGCTGGTACACTATCATGTACTAGTAAGTTGCGTAAGCGCA
GGGGAGCTGGTAGCACTCATATCGACGTTCTGCACCATTGCGAGTGTATATTTCTCAGAATCTCACTACAAGAACCCGTT
TGTGTCATGTATTGTTCTTAGTATCGTAGAAGATATCGATCGAGATAATGTGATTATTCATACTTATCGTGTAGTCTACG
TGTGTAATTTTACAGATGCATGATGCTAAATAGCGGGTATGGCGCNCTTCCATTCCTTCTCTTGTTCTACCGTCGGTCT
CCTTTGGTGACATACATATAGTGGTTGTTCACTTTCGGTATTGACGTTATCTTATAGGACCGTGCCATGTTCACTCCAAT
TGCATATCGATCAACGCTCAATATGCAGATGCAATGTTAGTCTCACATCACATATCGTACCATGCTCGACGAAATGAGCT
AACTGTTCGCTTCCACTATAGTCAGTCACACTTCGTTACGTTGTATACGTACTTATCTGCATCATATATGCACGTAGAAC
GCGTGATGGGTGTAAGCACTATGATTGTTGTTACAGT

Barley SHR HvGI TC147542
(SEQ ID NO: 14)
MADTPTSRMI HPFSNMQRQN PKQFQFQYPD NPQHPCHPYQ PSPDTHVVPQ HHYSLKSHSS
DASYENHVAQ MKHTLVDSSA AAGCMRHDSP SSHSFTPPSI RSGSGSPSSH DDSHSDSTDG
SPVSASCVTV TTEDPNDLKQ KLKDLEAEML GPDAAEIVNS LESSVAKQLS LEPEKWAQMM
DFPRGNLKEL LLACARAVEE KNMYAVDVMV PELRKMVSVS GTPLERLGAY MVEGLVARLA
SSGHSIYKAL RCKEPKSSDL LSYMHFLYEA CPYFKFGYMS ANGAIAEAVK GEDRIHIIDF
HIAQGAQWIS LLQALAARPG GPPTVRITGI DDSVSAYARG GGLDLVGRRL SHIAGLCKVP
FEFRSVAMAG EEVEEGHLGV VPGEALAVNF TLELHHIPDE TVSTANHRDR ILRLVKGLRP
KVLTLVEQES NTNTAPFPQR FAETLDYYTA IFESIDLTLP RDDRERVNME QHCLAREVVN
LIACEGAERV ERHEVFGKWK ARLTMAGFRP SPLSSLVNAT ISKLLQSYSD NYKLAERDGA
LYLGWKKRPL VVSSAWH Barley SHR nucleotide sequence
(SEQ ID NO: 15)
ATGAAGCGCGAGTACCAGGACGGCGGCGGGAGCGGCGGTGGGGGTGATGAGATGGGGTCGTCGAGGGACAAGATGATGGT
GTCGTCGTCGGAGGCGGGGGAGGGGGAGGAGGTGGACGAGCTGCTGGCGGCGCTCGGGTACAAGGTGCGGGCGTCCGACA
TGGCGGACGTGGCGCAGAAGCTGGAGCAGCTCGAGATGGCCATGGGGATGGGCGGCCCCGCCCCCGACGACGGCTTCGCG
ACCCACCTCGCCACGGACACCGTCCACTACAACCCCACCGACCTCTCCTCCTGGGTCGAGAGCATGCTGTCCGAGCTCAA
CGCGCCGCCGCCGCCCCTCCCGCCGGCCCCGCCGCAGCTCAACGCCTCCACCTCTTCCACCGTCACGGGCGGCGGCGGAT
ACTTCGATCTCCCGCCCTCTGTCGACTCCTCCAGCAGCACCTACGCCCTGCGCCCGATCATCTCGCCGCCCGTCGCGCCG
GCCGACCTCTCCGCTGACTCCGTCCGGGACCCCAAGCGGATGCGCACTGGCGGCAGCAGCACGTCGTCTTCGTCCTCCTC
GTCGTCCTCGCTCGGCGGTGGTGCCGCCAGGAGCTCTGTGGTGGAGGCTGCTCCGCCGGTGGCGGCTGCGGCTGCTGCGC
CCGCGCTGCCGGTCGTCGTGGTCGACACGCAGGAGGCCGGGATTCGGCTGGTGCACGCGCTGCTGGCGTGCGCGGAGGCC
GTGCAGCAGGAGAACCTCTCGGCCGCCGAGGCGCTGGTGAAGCAGATACCCTTGCTGGCAGCGTCGCAGGGCGGCGCGAT
GCGCAAGGTCGCCCCCTACTTCGGCGAGGCCCTCGCCCGCCGCGTCTTCCGCTTCCGCCCGCAGCCGGACAGCTCCCTCC
TCGACGCCGCCTTCGCCGACCTCCTCCACGCGCACTTCTACGAGTCCTGCCCCTACCTCAAGTTCGCCCATTTCACCGCC -continued

```
AACCAGGCCATCCTGGAGGCGTTCGCCGGCTGCCGCCGCGTCCACGTCGTCGACTTCGGCATCAAGCAGGGGATGCAGTG
GCCGGCCCTTCTCCAGGCCCTCGCACTCCGTCCCGGCGGGCCCCCTTCGTTCCGCCTCACCGGCGTTGGCCCCCCGCAGC
CGGACGAGACCGACGCCCTGCAGCAGGTGGGCTGGAAGCTCGCCCAGTTCGCGCACACCATCCGCGTCGACTTCCAGTAT
CGCGGCCTCGTCGCCGCCACGCTCGCGGACCTGGAGCCGTTCATGCTGCAGCCGGAGGGCGAGGAGGACCCTAACGAGGA
GCCCGAGGTAATCGCCGTGAACTCAGTCTTCGAGATGCACCGGCTCCTCGCGCAGCCCGGCGCCCTCGAGAAGGTCCTGG
GCACGGTGCGCGCCGTGCGGCCGAGGATCGTCACCGTGGTCGAGCAGGAGGCGAACCACAACTCCGGCTCATTCCTGGAC
CGCTTCACCGAGTCCCTGCACTACTACTCCACCATGTTCGATTCTCTCGAGGGCGGCAGCTCCGGCGGCCCGTCCGAGGT
CTCATCGGGGGGTGCCGCTCCTGCCGCCGCCGCCGGCACGGACCAGGTCATGTCCGAGGTGTACCTCGGCCGGCAGATCT
GCAACGTGGTGGCCTGCGAGGGCACGGAGCGCACAGAGCGGCACGAGACACTGGGGCAGTGGCGGAACCGGCTGGGCAAC
GCCGGGTTCGAGACCGTGCACCTGGGCTCCAATGCCTACAAGCAGGCGAGCACGCTGCTGGCCCTCTTCGCCGGCGGCGA
CGGGTACAAGGTGGAAGAGAAGGAAGGGTGCCTGACTCTCGGGTGGCACACGCGCCCGCTGATCGCCACTTCCGCATGGC
GCCTCGCCGCGCCGTGATCGCGAGTTTTGAACGCTGTAAGTAGACATCGTGAGAGCATGGAGCGCTACGACACAACCCCG
GCCGCCCGCCCGCCCCGGCTCTCCGGCGCACGCACACGCACTTGAAGAAGAAGAAGATGAAGAAGAAGCTAAATGTCAGT
GATACGCTGAATTGCAGCGACCGGCTAGGATCGATCGGGTTACCACTCTACGGTTTGGTTCTGCGTCCGGCGTGAAGACA
TGGACACGACCAACTCCGACCAGACCGCCGGCATGTAATGTAATCCCTCCTTCGTTCCCAGTTCACCATCACCCGTAAAA
CTCCTTATTAAGCCCTATTACTATTATTATTATGTTTAAATGTCTATTACTATTGCTATGTGTAATTCCTCCAATCGCTC
ATATTGAAATAAGCACGGGCCGGACTTTTGNTAGCAAGCTGCTTCATTTGAGAATTTTTGTACCGCAAGGGCACATCT
```

Barley SHR AAL66734.1 GI: 18254373

(SEQ ID NO: 16)

```
MKREYQDGGG SGGGGDEMGS SRDKMMVSSS EAGEGEEVDE LLAALGYKVR ASDMADVAQK
LEQLEMAMGM GGPAPDDGFA THLATDTVHY NPTDLSSWVE SMLSELNAPP PPLPPAPPQL
NASTSSTVTG GGGYFDLPPS VDSSSSTYAL RPIISPPVAP ADLSADSVRD PKRMRTGGSS
TSSSSSSSS LGGGAARSSV VEAAPPVAAA AAAPALPVVV VDTQEAGIRL VHALLACAEA
VQQENLSAAE ALVKQIPLLA ASQGGAMRKV APYFGEALAR RVFRFRPQPD SSLLDAAFAD
LLHAHFYESC PYLKFAHFTA NQAILEAFAG CRRVHVVDFG IKQGMQWPAL LQALALRPGG
PPSFRLTGVG PPQPDETDAL QQVGWKLAQF AHTIRVDFQY RGLVAATLAD LEPFMLQPEG
EEDPNEEPEV IAVNSVFEMH RLLAQPGALE KVLGTVRAVR PRIVTVVEQE ANHNSGSFLD
RFTESLHYYS TMFDSLEGGS SGGPSEVSSG GAAPAAAAGT DQVMSEVYLG RQICNVVACE
GTERTERHET LGQWRNRLGN AGFETVHLGS NAYKQASTLL ALFAGGDGYK VEEKEGCLTL
GWHTRPLIAT SAWRLAAP
```

Residues 1 to 120 of PtSHR1

(SEQ ID NO: 17)

```
MDTLFRLVSLQQQSEQSFNSTSRTSSSSRSSRQNNNHHHHHYQQEDEECFNFFMDEEDFSSSSSKHYYPPYHHNQ
QQQHQHQTTTTTPTTTTTNTSTPSTHHVLDSADFSFSPSHDLNFE
```

SEQ ID NO: 18

VMKEIG(N/Q)RMEKFARLMGVPF(K/E)(F/L)(N/K)VI

SEQ ID NO: 19

LNEL(G/A)SPYGD(T/C)(E/D)QKLAS(Y/H)FLQALF

SEQ ID NO: 20

LKFQEVSPW(T/A)TFGHV

SEQ ID NO: 21

CTQWPTLLEALATR

AtSHR promoter

-continued (SEQ ID NO: 22)
agatttcgagaaattacataagaaactgaattgcaacactcgataggtttcgaagaaagggacaaagaagcagag cgtgggtttcttctaataattgtagaagaaactgatcatgagaacatttgatctaccagagatggtgatgactc ataagatgtaaatatctactgcattatgtctagcctaggctataatgtagatttgatcactttcttcattaatta gtttggaattttagcatgatatagcatatatctaaatatgtccgaaactttcctacatactagaaaatatggaga gttatgtaatgtaggtttgcttgttaatatacaaaataacatcatcatttagttttttagatttttattttattt tttataatggtgctacgtacgtggcgatcaaattattccaattttgagacttcgggattttaaacgaaatttaaac aatgggcatgagctcggggggatagacaagattaatgctttgtatcgagacaaacgagaaaatcatgatgagcct atgcattaagtgccgttggttaattagaggttcgcatatacataaaccagtagacatatggataaatatgaacac acacaccaaaaaagtgggaaatctaaataagtgtagagaataataagtcctcaggtgggagattcaaagagagga caatgaagggtatatagactctaaacaaaaatggcatgacttagtggagagggttttaaattgaaacaagtagga ttgaagaacaagaaaacaaagaagcatgccctagatttctgagataataattacacattgctgtttatataaggt aagagaatatgacacattggttggtttcttacgggtaaatgtgaagaaaaaaaaatagtaatatttgagaaaatc taaaatagtaaagaggtatatatggagaagaagagagaaaagggaaaaatagtggcagagaatggagagaggtta ggaggcaaaggcaaatgtggagctttgatgatgttgatgcacgccgtcagcttttcttcacgcctgctcccactc actcacacctatgaacattctctctctatttttataattatattcacatgtctctatgttactatgtaaatggtga ccacttaagtatttatatatcatgtatatatcttataggtatcatacaaaatggtcatgaaacttttgcaatttc aatctacttgttcattgtagatgctagcttttcacatgttttgaaaattagtctggatctgaaattctttaatta gcattgttttgttggtcaacgtttaatttcttgattattgatgtcaaaaattcagagcgttcagaactcttacac taatttcttaaaaataatcgattaagagaaaatagagttttcatgcaccagtgttgatagtaacgtagtcgcgga atgtctaaaacgattatgagtttggtgttttgattggttagaattggtattagtaggacattctaactttttttgt tagtctgttgatttaggatgcgtaaagagtctttttatttacaccagttgagacttgggatcgatagtacttga aacacttggttggtttcatgtatttggcctatatataaacaaacatcgtaattatatacggatttttttcggaat tttacgccatatctgtaagtatatataacatgcatgtcgttttcaaattcatatgatgaacgatccacgtaagtg ctactactcctacaatattgcatgagagagatatgtatttataaattttattttgaagaagaaataagagggaag gttacttgggtggatcgatgtgaaaacaaaagaagaaaaagcgaaacccactaagccattacatgatatcgacct tcttatcttttcctctttattttattttttctcaggactttttttctacttaatgaaacctccaaactatctaact aatacactcccatgtagaataaagaaaattatataagatattgttgatattttgtaactagaaaatatatttgct ctgtaattttcgtaagttaaatcaacattttcagtagaaacaaatattactgcaaaaagtaggatcattatttt ttgtccaaaatctcagttagctataggggttgtagtaaaaacaaaacacattcttgatttgcccaaaaaataaag agagagaagaatattgttcaaaagtggtctcttctctctctaattatgttttcactaaacccaattagattcaaa cagtctacaaagtccaaaagataaacatgggacaacaattcgatgcaaaaatcctcttttcatgctctttttt attctctagtcttttaaattactaataaaaactcacaaatccaccaaacccattctctacaactcaccttcatct agatttacccactcccaccgagaaacacaagaaaaaaaatatacatatataaatatacaagacaacacatgatgc tgatgcaatatacacaacaaagtattaaatcttagatattgtgggtctcccttcttctattcattttcttattc attaaaaaaaaaaa PtSHR promoter (SEQ ID NO: 23)
AAATCAATAAAAAAACAAAATAAATAACAATCAAAAGAATGACCAAATTAGATATAAAAGAACAAATAAA

ATGAAACATTTATATTTTGGCAAGGAGAAAAGGAGAAAAATAGGGAGGAGAAGAAATAAATATTCAATCG

GAGCAAATCATTACACTGTCATGTACACGCGTCAGACTATTGAATAGAGGATGGCAGGATGCTTCCATCT

TTGCCATGAAAACCGGTGTTTGGAGGGTAGATAATGCCTTAAACATTGCCTAAAAGGCAGGGGTATCGTC

-continued

CAACGCCCGCACCAACCACTTTTTATTTTTAACTAATATCTAAATTTATCAAAATACCAAATCGCTTCCA

AGTCAACTTGATAATTACTAAAAACATATTATGAAATGACCAAAAAGCACTTGAATAATAGTTTGAAAAT

TTTTGCTTTTAAAGGTAATTTAGTCTTTATATTATATTTTTGAAATGTAAAAAGATCAAATTACCCTTGA

TCAATATTTTTAGAAAATTTGTTTTTAAGGGTAATAAAGTTTTTAAAATATGCATTTAAAAGGTTAAAAG

ACCAAATTATTCCATAAGAAAAAAACCGTTTTACTTCCAATAGCAAGTTAATTGATTTTTTGTTGGAAG

GGGAAAATATAATTACACTATTATAGTGAACATGGCTTTCAATTTATTTTTTATTTAAAGGGTCCTTTGT

CTCAATTCTGATAAAAAAGTTAGTATTTTCTACTTTTAAAAATATTATAAGTTTTTATTTCAATTATGA

ATGTTATAATAATTAAAAAATATATATGATATAGGTGTAATGCTATTATAGAAAAAATATAAAATAAATT

ACCTACCTTTTTATCTTCTACTCACAAAAAAAATTAAAATAGTTTTTTTAAATAGATTTATGCTTGTT

CTATTTTTTTAATAGATGTACTTATGTGAGAGTAAGCGGCAATAAATTTGAAACAAAATTAGTGAGATC

ACCTTTATTCAAATAATAAGACCGGGTCACCGGGTCATATATATATATATATATATATATATATATATAT

ATATATATATATATATATATATGCTTGCAGTCAACAATAATGATTTCCAATTTTATTTAAACCGAATG

ATCTACACGAGACAGAATCCAGACGTGATAGTTTTCCTAATGATTGATGGAGAAAACCAAGGACGAGCAG

TGATTAGGAACAAGGAAAATTTCAACAGACAAAAGAAACTCATATATATATATATAGACACACACTCTCA

CCTCTTGCGTATGAAAATGTAGAATAGCAATAGAGCATAATGTTGCTGACTATAAAAGCAAAGAGTAGAC

CAACCGTGACATACATTAAAATCCAAATATTTGATCTGCGTTGAGGTTTAGCAAGCTGACACAGAAAGAA

ATAAATGTTTGTGCCTAGCTATATGTAGGCCAACCAAATATAGATATAGTTTCTAGAGAGAATTAAGGTT

CAGCTTGAGGACAACAAGGTTAAGACAATAAAAGGCGAAGTAGTACGTGGTTGTGGTGTAATCATAATGA

ACCGGCTTGGCTATGAATTTTGACTAAAAAAAGAGCAAGTCACTAGCGGGAGTAAGATTTGAGGTTGTGA

CATGGAAGGAGAGCCTAGCTATATATGGTTGGGCCATCTTGAGAAATGGCCTAGCTAGCTAGTTTGGTGC

ATATATGGTGTATGGAATGAATGGATTTATAATAAGTGTTTGCTATATATATATATATATATATATATAT

ATATATATATATATATAAACTAAACTATCATGTGGAAGTGGGGAAAAAAGTGAAAGAGCACGCCCTAG

ATTTTTATATTACAAAAGAGCATTGGTTATAATTAAATGGAAGTTGATTTATGTTACACAGTGTAGAAAA

GGCAAAAGCGGGGTGGAATTTTGGCAGAGATTGAAGAGGGATTAGGAGGCAAGGAATGTGAATAGGATGG

GTTGGAGGGATGATAGTGGGTTTGATAATGATGATGCACGCCGGCAGCTTTACTCATTTATCTTCCCAAA

ATCCAATTGGCACGCCTGCCCCCACTAAAACCTATAACAATATTCTCTTCTCTCTTTCAATCTTTCTCAT

AGACAATGAAAAGCTAATCCACTAACCCATTTGGTGATCTAGCTAGACCTTGTTATCTTTCTCTTTTTA

ATCTTTTTGTCAGATAACATTTCTATTTCTCAACACCAGTAGCTCTTTCATGCCAACTTCCCACGTTCTT

CCAGGGAAAACGTATATTAGTCATATCTCTCATGAGTTGATTAAAAAAGAAAGGAAAAAAGGGAGAAGAC

TGGGCTAGCTAGCTAGATAAAAGAATATCCCAAACCCCACCCAATTTGATTCACATCGACTACAGAAAAA

GAAAAGCACATTTAAACATGTATGTATGTATATATATGTATATATATAAATATCCAACTTCAAGATCCTC

TCTTTTATCATTCTCTACCCCAATATTCCCACAGTTAAAAACACAAACACCCATCCCCTTACCTTCACTC

CAAGCCATCCCCAACAAACTCCATCCGAA

The invention claimed is:

1. A method of increasing the growth and/or biomass of a *Populus* plant comprising:
reducing but not abolishing the expression of a SHORT-ROOT (SHR) polypeptide within cells of said *Populus* plant relative to control plants,
wherein the SHORT-ROOT (SHR) polypeptide has greater than 60% sequence identity with SEQ ID NO: 2 and comprises an amino acid sequence which has at least 80% sequence similarity to SEQ ID NO: 20 and an amino acid sequence which has at least 90% sequence similarity to SEQ ID NO: 21, and
wherein expression is reduced by expressing a heterologous nucleic acid which encodes a suppressor RNA molecule within cells of said *Populus* plant.

2. A method of producing a *Populus* plant with increased growth or biomass comprising:
incorporating a heterologous nucleic acid which alters the expression of a
SHORT-ROOT (SHR) polypeptide into a *Populus* plant cell by means of transformation, and
regenerating a *Populus* plant from the transformed cell,
wherein the heterologous nucleic acid encodes a suppressor RNA molecule which reduces but does not abolish the expression of the SHORT-ROOT (SHR) polypeptide, and
wherein the SHORT-ROOT (SHR) polypeptide has greater than 60% sequence identity with SEQ ID NO: 2 and comprises an amino acid sequence which has at least 80% sequence similarity to SEQ ID NO: 20 and an amino acid sequence which has at least 90% sequence similarity to SEQ ID NO: 21.

3. A *Populus* plant product or part thereof comprising a heterologous nucleic acid which alters the expression of a SHORT-ROOT (SHR) polypeptide,
wherein the heterologous nucleic acid encodes a suppressor RNA molecule which reduces but does not abolish the expression of the SHORT-ROOT (SHR) polypeptide, and
wherein the SHORT-ROOT (SHR) polypeptide has greater than 60% sequence identity with SEQ ID NO: 2 and comprises an amino acid sequence which has at least 80% sequence similarity to SEQ ID NO: 20 and an amino acid sequence which has at least 90% sequence similarity to SEQ ID NO: 21.

4. The method of claim 1 wherein the heterologous nucleic acid comprises an inverted repeat which is complementary to a nucleic acid sequence that encodes the SHORT-ROOT (SHR) polypeptide.

5. The method of claim 1 wherein the heterologous nucleic acid is an antisense nucleic acid sequence which is complementary to a nucleic acid sequence that encodes the SHORT-ROOT (SHR) polypeptide.

6. The method of claim 1 further comprising sexually or asexually propagating or growing off-spring or descendants of the *Populus* plant having reduced but not abolished SHORT-ROOT (SHR) polypeptide expression, wherein the sexually or asexually propagated off-spring or descendants comprise said heterologous nucleic acid.

7. The method of claim 2 wherein the heterologous nucleic acid comprises an inverted repeat of a nucleic acid sequence which is complementary to a nucleic acid sequence that encodes the SHORT-ROOT (SHR) polypeptide.

8. The method of claim 2 wherein the heterologous nucleic acid is an antisense nucleic acid sequence which is complementary to a nucleic acid sequence that encodes the SHORT-ROOT (SHR) polypeptide.

9. The method of claim 2 wherein the above ground portion of said *Populus* plant shows increased growth and/or biomass relative to controls.

10. The method of claim 2 further comprising sexually or asexually propagating or growing off-spring or descendants of the *Populus* plant regenerated from the *Populus* plant cell, wherein the sexually or asexually propagated off-spring or descendants comprise said heterologous nucleic acid.

11. The *Populus* plant product or part thereof of claim 3 wherein the heterologous nucleic acid comprises an inverted repeat which is complementary to a nucleic acid sequence that encodes the SHORT-ROOT (SHR) polypeptide.

12. The *Populus* plant product or part thereof of claim 3 wherein the heterologous nucleic acid is an antisense nucleic acid sequence which is complementary to a nucleic acid sequence that encodes the SHORT-ROOT (SHR) polypeptide.

13. The *Populus* plant product or part thereof of claim 3 wherein the steady-state level of mRNA encoding the SHORT-ROOT (SHR) polypeptide in said *Populus* plant or part thereof is 20% to 80% of the steady-state level of the corresponding mRNA in a wild type plant.

* * * * *

UNITED STATES PATENT AND TRADEMARK OFFICE
CERTIFICATE OF CORRECTION

| | | |
|---|---|---|
| PATENT NO. | : 9,074,217 B2 | Page 1 of 1 |
| APPLICATION NO. | : 12/595484 | |
| DATED | : July 7, 2015 | |
| INVENTOR(S) | : Brian Jones, Jiehua Wang and Goran Sandberg | |

It is certified that error appears in the above-identified patent and that said Letters Patent is hereby corrected as shown below:

Title page, item (30), Foreign Application Priority Data, was omitted in the left-hand column and should be inserted between items (65) and (51):

--(30)     Foreign Application Priority Data

Apr. 12, 2007          (GB)...................0707089.9--.

Signed and Sealed this
Twenty-sixth Day of July, 2016

Michelle K. Lee
*Director of the United States Patent and Trademark Office*

SEQUENCE LISTING

<160> NUMBER OF SEQ ID NOS: 41

<210> SEQ ID NO 1
<211> LENGTH: 2173
<212> TYPE: DNA
<213> ORGANISM: Populus trichocarpa

<400> SEQUENCE: 1

| | |
|---|---|
| gggagaagac tgggctagct agctagataa aagaatatcc caaaccccac ccaatttgat | 60 |
| tcacatcgac tacagaaaaa gaaaagcaca tttaaacatg tatgtatgta tatatatgta | 120 |
| tatatataaa tatccaactt caagatcctc tcttttatca ttctctaccc caatattccc | 180 |
| acagttaaaa acacaaacac ccatcccctt accttcactc caagccatcc ccaacaaact | 240 |
| ccatccgaat tctattgatg tgggtctctg gattttggtt aaatggatac cttgtttagg | 300 |
| ctagttagtc tccaacaaca atctgaacaa tctttcaact ctactagcag aacctctagt | 360 |
| agctctagat catcaagaca aaacaacaac caccaccatc atcactatca acaagaagac | 420 |
| gaagaatgct tcaactttt catggatgag gaagacttct cttcatcttc ttctaagcac | 480 |
| tactatcctc cttatcacca caaccaacaa caacaacatc aacaccaaac caccaccacc | 540 |
| actcctacca ctactaccac caacactagc accccttcta ctcaccatgt ccttgattcc | 600 |
| gctgacttct ctttctcccc ttctcatgac ctaaactttg aattttccgg caagtgggtc | 660 |
| accgatatcc tccttgaatc tgcacatgcc atcgcggata aaaacagcgc tcgtctccag | 720 |
| caattgatgt ggatgcttaa tgagcttggt tcaccttatg gtgacacaga gcaaaaactt | 780 |
| gcttcttatt ttctccaagc tttgtttagc cgcatgaacg actccggcga gagatgctac | 840 |
| cgtactttag cttcagcatc agagaaaact tgctctttg attccacaag gaaaatggta | 900 |
| ttaaagtttc aagaggtgag tccttggact acttttggtc acgtatcttg taatggcgca | 960 |
| attatgaag catttgaagg tgaaagcaaa ttgcatatta ttgatattag taacacatat | 1020 |
| tgtacccaat ggcctacttt gctcgaagcc ctagcaactc gcactgatga gacaccacac | 1080 |
| ttgaagttaa ccaccgtagt ggctagcaaa agtagtggta ataatattgg tttaactagt | 1140 |
| acaggaggtt tagcttcagt tcataaggta atgaaagaaa ttggcaacag aatggaaaaa | 1200 |
| tttgccaggc ttatgggagt cccatttaag tttaatgtta tccaccatgc tggtgattta | 1260 |
| tgtgacctaa acttagctga attggatgtt aaagatgatg aggctcttgc tatcaactgt | 1320 |
| gttggtgctt tacactcaat cactccagct tctcgtcgcc gagattatgt tatatctagt | 1380 |
| tttagaacat tgcaaccaag aatcattact gttgttgaag aagaagctga tcttgatggt | 1440 |
| ctggattttg tcaagggttt tcaagaatgt ttaagatggt ttagggttta ctttgaatca | 1500 |
| ttggatgaga gctttccaag aaccagtaac gaacagttga tgcttgaaag agcagcaggc | 1560 |
| cgcgctatcg ttgacttagt ggcatgtcct ccatctgatt cgatcgaaag gcgggaaaca | 1620 |
| gccacgcgct ggtctggacg cctccattca tgtggtttta gcccgataat tttcagtgat | 1680 |
| gaggtttgtg atgatgtacg cgccttattg aggaggtata aggagggttg gtcaatgaca | 1740 |
| cagtgcgggg atgccggaat attcttgtgc tggaaggaac agccggtggt gtgggctagt | 1800 |
| gcatggaggc cctgattgag attggtgatg gttttcactt tcacttttc ttttctttct | 1860 |
| tttttctttt gttttgctt ttctccttgt atttttttt tttcaaagtt agtttgagtg | 1920 |
| attggcacgt ttgatgtgtt tatttgggca cgtgcatgga ttaaggattg gaatagtaaa | 1980 |
| tgaagttaat caatttcat tgatctttgt ttaattatca tttgcggtta tttcttattt | 2040 |
| ttatgaaaaa tagctttctt aatcatcata tcaaagaaac gtttttaatt caatgatgta | 2100 |
| aacaaattag ttgagcaaga tttatctttg gggtaaataa atgatttaat ttaggaaagt | 2160 |
| tattcgataa tta | 2173 |

<210> SEQ ID NO 2
<211> LENGTH: 510
<212> TYPE: PRT
<213> ORGANISM: Populus trichocarpa

<400> SEQUENCE: 2

```
Met Asp Thr Leu Phe Arg Leu Val Ser Leu Gln Gln Gln Ser Glu Gln
 1               5                  10                  15

Ser Phe Asn Ser Thr Ser Arg Thr Ser Ser Ser Ser Arg Ser Ser Arg
            20                  25                  30

Gln Asn Asn Asn His His His His Tyr Gln Gln Glu Asp Glu Glu
        35                  40                  45

Cys Phe Asn Phe Phe Met Asp Glu Glu Asp Phe Ser Ser Ser Ser Ser
    50                  55                  60

Lys His Tyr Tyr Pro Pro Tyr His His Asn Gln Gln Gln His Gln
65                  70                  75                  80

His Gln Thr Thr Thr Thr Pro Thr Thr Thr Thr Asn Thr Ser
                85                  90                  95

Thr Pro Ser Thr His His Val Leu Asp Ser Ala Asp Phe Ser Phe Ser
                100                 105                 110

Pro Ser His Asp Leu Asn Phe Glu Phe Ser Gly Lys Trp Val Thr Asp
            115                 120                 125

Ile Leu Leu Glu Ser Ala His Ala Ile Ala Asp Lys Asn Ser Ala Arg
130                 135                 140

Leu Gln Gln Leu Met Trp Met Leu Asn Glu Leu Gly Ser Pro Tyr Gly
145                 150                 155                 160

Asp Thr Glu Gln Lys Leu Ala Ser Tyr Phe Leu Gln Ala Leu Phe Ser
                165                 170                 175

Arg Met Asn Asp Ser Gly Glu Arg Cys Tyr Arg Thr Leu Ala Ser Ala
            180                 185                 190

Ser Glu Lys Thr Cys Ser Phe Asp Ser Thr Arg Lys Met Val Leu Lys
        195                 200                 205

Phe Gln Glu Val Ser Pro Trp Thr Thr Phe Gly His Val Ser Cys Asn
210                 215                 220

Gly Ala Ile Met Glu Ala Phe Glu Gly Glu Ser Lys Leu His Ile Ile
225                 230                 235                 240

Asp Ile Ser Asn Thr Tyr Cys Thr Gln Trp Pro Thr Leu Leu Glu Ala
                245                 250                 255

Leu Ala Thr Arg Thr Asp Glu Thr Pro His Leu Lys Leu Thr Thr Val
            260                 265                 270

Val Ala Ser Lys Ser Ser Gly Asn Asn Ile Gly Leu Thr Ser Thr Gly
        275                 280                 285

Gly Leu Ala Ser Val His Lys Val Met Lys Glu Ile Gly Asn Arg Met
290                 295                 300

Glu Lys Phe Ala Arg Leu Met Gly Val Pro Phe Lys Phe Asn Val Ile
305                 310                 315                 320

His His Ala Gly Asp Leu Cys Asp Leu Asn Leu Ala Glu Leu Asp Val
                325                 330                 335

Lys Asp Asp Glu Ala Leu Ala Ile Asn Cys Val Gly Ala Leu His Ser
            340                 345                 350

Ile Thr Pro Ala Ser Arg Arg Asp Tyr Val Ile Ser Ser Phe Arg
        355                 360                 365

Thr Leu Gln Pro Arg Ile Ile Thr Val Val Glu Glu Ala Asp Leu
            370                 375                 380

Asp Gly Leu Asp Phe Val Lys Gly Phe Gln Glu Cys Leu Arg Trp Phe
385                 390                 395                 400

Arg Val Tyr Phe Glu Ser Leu Asp Glu Ser Phe Pro Arg Thr Ser Asn
```

| | | | | | | | | | | | | |
|---|---|---|---|---|---|---|---|---|---|---|---|---|
| | | | 405 | | | | 410 | | | | 415 | |
| Glu | Gln | Leu | Met | Leu | Glu | Arg | Ala | Ala | Gly | Arg | Ala | Ile | Val | Asp | Leu |
| | | | 420 | | | | | 425 | | | | 430 | | | |
| Val | Ala | Cys | Pro | Pro | Ser | Asp | Ser | Ile | Glu | Arg | Glu | Thr | Ala | Thr |
| | | 435 | | | | | 440 | | | | | 445 | | |
| Arg | Trp | Ser | Gly | Arg | Leu | His | Ser | Cys | Gly | Phe | Ser | Pro | Ile | Ile | Phe |
| | 450 | | | | | 455 | | | | | 460 | | | | |
| Ser | Asp | Glu | Val | Cys | Asp | Val | Arg | Ala | Leu | Leu | Arg | Arg | Tyr | Lys |
| 465 | | | | | 470 | | | | | 475 | | | | | 480 |
| Glu | Gly | Trp | Ser | Met | Thr | Gln | Cys | Gly | Asp | Ala | Gly | Ile | Phe | Leu | Cys |
| | | | | 485 | | | | | 490 | | | | | 495 | |
| Trp | Lys | Glu | Gln | Pro | Val | Val | Trp | Ala | Ser | Ala | Trp | Arg | Pro | | |
| | | | 500 | | | | | 505 | | | | 510 | | | |

<210> SEQ ID NO 3
<211> LENGTH: 1924
<212> TYPE: DNA
<213> ORGANISM: Populus trichocarpa

<400> SEQUENCE: 3

| | | | | | |
|---|---|---|---|---|---|
| aagtcctcgc | cacttatatg | tgtttattga | gaaaaaaata | tatattatac | atgtagtacg | 60 |
| tacgtatgat | atgcaatatc | gaacaagtat | atactagcta | gggctttgag | gttattgcaa | 120 |
| ttatggttgc | caaatccaac | cactacacta | gcaattaggt | atttttcatc | tcgagatcac | 180 |
| aatatcatta | atttgaagct | aataatacac | ataaaaatag | aaattcatat | taagaaaaaa | 240 |
| tatatatata | tagcatgact | atgaccccca | accccaaaaa | tataatacta | cggatttcta | 300 |
| tatcatagct | ttgtacttgg | ccaattttt | tgaattagca | gaggtactgc | ctccagagtc | 360 |
| aaaggggggcc | ttccctagct | atcacccacg | gacataacca | tcttcggtcc | aaaagacaga | 420 |
| ctcacacact | tatttccttc | ccaccaacaa | agcaatgatc | aaatagaagc | tagctataga | 480 |
| catgcaaagc | aatagcagca | acaacaacaa | caatcagcct | cagactagtc | atacatcaac | 540 |
| aagccgttct | tcggactccg | gtgaggcttg | tggggcagga | aacaaatggg | catcaaggct | 600 |
| tcttagtgag | tgtgcaagag | caatctcaga | gaaggactct | agcaagatcc | ataaccttct | 660 |
| atggatgtta | aatgagcttg | cctctcctta | tggagattgt | gaacagaaat | tggcatctca | 720 |
| tttcttgcaa | gctctctttt | gtaaggctac | cgactccggc | caacggtgct | tcaaaaccct | 780 |
| aacaacagta | gctgaaaaga | gccactcctt | tgattcagct | aggaaattga | tactaaaatt | 840 |
| ccaagaggta | agcccatgga | ctacttttgg | tcatgtggct | tcaaacggtg | caattttgga | 900 |
| ggccttagat | ggggcgagca | aacttcacat | aattgatata | agccataccc | tttgcacaca | 960 |
| atggcctact | ttgctagaag | ctttagctac | aagaaatgat | gagacgccgc | atttaaagct | 1020 |
| caccgttgtg | gtaactgcta | gcattgtaag | atcggtcatg | aaagaaattg | gccaaagaat | 1080 |
| ggagaagttt | gctaggttaa | tgggagtgcc | ctttgagctt | aatgtaatta | gtgggctaaa | 1140 |
| ccatttagga | gagctcacaa | aggacaggct | aggagttcaa | gaagatgaag | ctgtcgcgat | 1200 |
| taattgcaat | ggggcattga | gaagagttgg | agtagaggaa | agaaattctg | tgatccagat | 1260 |
| gtttcaatca | cttaaccctc | gagttgtgac | aattgttgaa | gaagaagctg | attttactag | 1320 |
| ctcaagatat | gactttgtca | agtgctttga | agagtgcctt | aggtattata | cactatattt | 1380 |
| tgagatgcta | gaggagagct | ttgtcccaac | tagtaatgag | agattgatgt | tggagaggga | 1440 |
| atgttcaagg | aacatagtta | gagttttggc | ttgtgatgaa | ggaaatgatg | gaggagagtg | 1500 |
| tgaaagaagg | gagaggggaa | gccaatggtt | tgaaaggcta | agggaggcat | tttcccctgt | 1560 |

-continued

```
tgggttcagt gatgatgttg tcgatgatgt caaggcattg cttaagagat accgagctgg      1620
gtgggcacta gtgctacctc aaggagatca tgactcagga atttacttaa catggaaaga      1680
agaacctgtg gtatgggctt ctgcatggaa accctagagg agaattatag ctagaacacc      1740
atgatctcca cactcaaagt caaggcttag catggcaatt tattcacaat ttgggaagca      1800
ctgccatgaa cacaacatat tgattcctgt caatcatgaa gtactactac tttcactttt      1860
catttcttct tctcattcat gcatatttgt gtcttctgta ctccaacttt tctttctta       1920 tgct                                                                    1924
```

<210> SEQ ID NO 4
<211> LENGTH: 411
<212> TYPE: PRT
<213> ORGANISM: Populus trichocarpa

<400> SEQUENCE: 4

```
Met Gln Ser Asn Ser Asn Asn Asn Asn Gln Pro Gln Thr Ser
1               5                   10                  15

His Thr Ser Thr Ser Arg Ser Ser Asp Ser Gly Glu Ala Cys Gly Ala
            20                  25                  30

Gly Asn Lys Trp Ala Ser Arg Leu Leu Ser Glu Cys Ala Arg Ala Ile
        35                  40                  45

Ser Glu Lys Asp Ser Ser Lys Ile His Asn Leu Leu Trp Met Leu Asn
    50                  55                  60

Glu Leu Ala Ser Pro Tyr Gly Asp Cys Glu Gln Lys Leu Ala Ser His
65                  70                  75                  80

Phe Leu Gln Ala Leu Phe Cys Lys Ala Thr Asp Ser Gly Gln Arg Cys
                85                  90                  95

Phe Lys Thr Leu Thr Thr Val Ala Glu Lys Ser His Ser Phe Asp Ser
            100                 105                 110

Ala Arg Lys Leu Ile Leu Lys Phe Gln Glu Val Ser Pro Trp Thr Thr
        115                 120                 125

Phe Gly His Val Ala Ser Asn Gly Ala Ile Leu Glu Ala Leu Asp Gly
    130                 135                 140

Ala Ser Lys Leu His Ile Ile Asp Ile Ser His Thr Leu Cys Thr Gln
145                 150                 155                 160

Trp Pro Thr Leu Leu Glu Ala Leu Ala Thr Arg Asn Asp Glu Thr Pro
                165                 170                 175

His Leu Lys Leu Thr Val Val Thr Ala Ser Ile Val Arg Ser Val
            180                 185                 190

Met Lys Glu Ile Gly Gln Arg Met Glu Lys Phe Ala Arg Leu Met Gly
        195                 200                 205

Val Pro Phe Glu Leu Asn Val Ile Ser Gly Leu Asn His Leu Gly Glu
    210                 215                 220

Leu Thr Lys Asp Arg Leu Gly Val Gln Glu Asp Glu Ala Val Ala Ile
225                 230                 235                 240

Asn Cys Asn Gly Ala Leu Arg Arg Val Gly Val Glu Arg Asn Ser
                245                 250                 255

Val Ile Gln Met Phe Gln Ser Leu Asn Pro Arg Val Val Thr Ile Val
            260                 265                 270

Glu Glu Glu Ala Asp Phe Thr Ser Ser Arg Tyr Asp Phe Val Lys Cys
        275                 280                 285

Phe Glu Glu Cys Leu Arg Tyr Tyr Thr Leu Tyr Phe Glu Met Leu Glu
    290                 295                 300
```

```
Glu Ser Phe Val Pro Thr Ser Asn Glu Arg Leu Met Leu Glu Arg Glu
305                 310                 315                 320

Cys Ser Arg Asn Ile Val Arg Val Leu Ala Cys Asp Glu Gly Asn Asp
            325                 330                 335

Gly Gly Glu Cys Glu Arg Arg Glu Arg Gly Ser Gln Trp Phe Glu Arg
        340                 345                 350

Leu Arg Glu Ala Phe Ser Pro Val Gly Phe Ser Asp Asp Val Val Asp
    355                 360                 365

Asp Val Lys Ala Leu Leu Lys Arg Tyr Arg Ala Gly Trp Ala Leu Val
370                 375                 380

Leu Pro Gln Gly Asp His Asp Ser Gly Ile Tyr Leu Thr Trp Lys Glu
385                 390                 395                 400

Glu Pro Val Val Trp Ala Ser Ala Trp Lys Pro
                405                 410

<210> SEQ ID NO 5
<211> LENGTH: 1733
<212> TYPE: DNA
<213> ORGANISM: Populus trichocarpa

<400> SEQUENCE: 5
acatataaga atatttcaaa tataatacac aagaaattat tcacattaac aaaataggat      60
gactatgacc ccccacccca agatataatt atactatgga tatctatatc aatatagctt    120
tgtacttggc catgtctgaa ctcaaatgaa atttgagttt ggcaaaggtt ctgcctctag    180
agtcaaaggg ggcctcgccg atcaccaatg gacataactc tcttcagtcc aaaagacaca    240
ctgacacact tctttccttc ccaccagcaa agcaatgatc aagtagcagc tatagacatg    300
caaagcaata gcagcaacaa caacaataat cagcctcaaa ccagccatac atcaacaagc    360
cggtcttcgg actccggtga ggcctgtgga ggaggaaaca agtgggcatc aaagcttctt    420
agtgagtgtg caagagcaat ctcagagaag gactctagca agatccacca ccttctatgg    480
atgttaaatg agcttgcctc tccttatgga gattgtgatc agaaattggc atcttatttc    540
ttgcaagctc tattctgtaa ggctaccgag tctggtcaac ggtgtttcaa acccctaaca    600
acagtagctg aaaagagcca ctcctttgat tcagctagga aattgatact aaaattccaa    660
gaggtaagcc cgtggactac tttcggtcat gtagcttcaa atggtgcaat tttggaggcc    720
ttagatgggg aaagcaaact tcacataatt gatatcagca ataccctttg cacacagtgg    780
cctactttgc tagaagcttt agccacaaga aatgatgaga cgccgcgatt aaagctcacc    840
gttgtggtaa ctgctagcat tgtaagatca gtcatgaaag aaattggcca agaatggag     900 aagtttgcta ggttaatggg agtgcccttt gagtttaaag taattagtgt gctaaatcat    960
ataggagagc tcacaaagga aggactgggt gttcaagaag atgaagcagt cgcgattaat   1020
tgcattgggg cattgagaag agttgaagta gatgaaagaa gttctgtaat ccagttgttc   1080
cgatcactta accctcgagt tgtgacaatt gtagaggaag aagctgattt tactagctca   1140
agatatgact tcgtcaagtg ctttgaagag tgcctgaggt attatacact atattttgag   1200
atgctagaga gagctttgt cccaactagt aatgagagat tgatgttgga gagggaatgt   1260
tcaaggaaca tagttagggt tttggcttgt gatgaagaaa ctggtggagg agagtgtgaa   1320
agaagagagc ggggtgtcca atggtctgaa aggctaaggg aggcattttc ccctgttgga   1380
ttcagtgatg atgttgtcga tgatgtcaag gcattgctta agagatacaa agctgggtgg   1440
gcacttgtgc tacctcaagg agatcatgag tcaggaattt acttaacatg gaaagaggaa   1500
```

```
cctgtagtat gggcttctgc atggaaaccc taaaaggttg tggccagaac accatctcta    1560
tgctcaaatt caaggctcag catggcaatt tattcacaag atgggaacag cgcgccatga    1620
acacatattg ataattaatt atagagtact actactttca cttttcattt cttcttctta    1680
ttcatgcata tttgtatctt atgcactcca acttttcttt tcttatgtta tat           1733
```

<210> SEQ ID NO 6
<211> LENGTH: 411
<212> TYPE: PRT
<213> ORGANISM: Populus trichocarpa

<400> SEQUENCE: 6

```
Met Gln Ser Asn Ser Ser Asn Asn Asn Asn Gln Pro Gln Thr Ser
1               5                   10                  15

His Thr Ser Thr Ser Arg Ser Ser Asp Ser Gly Glu Ala Cys Gly Gly
            20                  25                  30

Gly Asn Lys Trp Ala Ser Lys Leu Leu Ser Glu Cys Ala Arg Ala Ile
        35                  40                  45

Ser Glu Lys Asp Ser Ser Lys Ile His His Leu Leu Trp Met Leu Asn
    50                  55                  60

Glu Leu Ala Ser Pro Tyr Gly Asp Cys Asp Gln Lys Leu Ala Ser Tyr
65                  70                  75                  80

Phe Leu Gln Ala Leu Phe Cys Lys Ala Thr Glu Ser Gly Gln Arg Cys
                85                  90                  95

Phe Lys Thr Leu Thr Thr Val Ala Glu Lys Ser His Ser Phe Asp Ser
            100                 105                 110

Ala Arg Lys Leu Ile Leu Lys Phe Gln Glu Val Ser Pro Trp Thr Thr
        115                 120                 125

Phe Gly His Val Ala Ser Asn Gly Ala Ile Leu Glu Ala Leu Asp Gly
    130                 135                 140

Glu Ser Lys Leu His Ile Ile Asp Ile Ser Asn Thr Leu Cys Thr Gln
145                 150                 155                 160

Trp Pro Thr Leu Leu Glu Ala Leu Ala Thr Arg Asn Asp Glu Thr Pro
                165                 170                 175

Arg Leu Lys Leu Thr Val Val Thr Ala Ser Ile Val Arg Ser Val
            180                 185                 190

Met Lys Glu Ile Gly Gln Arg Met Glu Lys Phe Ala Arg Leu Met Gly
        195                 200                 205

Val Pro Phe Glu Phe Lys Val Ile Ser Val Leu Asn His Ile Gly Glu
    210                 215                 220

Leu Thr Lys Glu Gly Leu Gly Val Gln Glu Asp Glu Ala Val Ala Ile
225                 230                 235                 240

Asn Cys Ile Gly Ala Leu Arg Arg Val Glu Val Asp Glu Arg Ser Ser
                245                 250                 255

Val Ile Gln Leu Phe Arg Ser Leu Asn Pro Arg Val Val Thr Ile Val
            260                 265                 270

Glu Glu Glu Ala Asp Phe Thr Ser Ser Arg Tyr Asp Phe Val Lys Cys
        275                 280                 285

Phe Glu Glu Cys Leu Arg Tyr Tyr Thr Leu Tyr Phe Glu Met Leu Glu
    290                 295                 300

Glu Ser Phe Val Pro Thr Ser Asn Glu Arg Leu Met Leu Glu Arg Glu
305                 310                 315                 320

Cys Ser Arg Asn Ile Val Arg Val Leu Ala Cys Asp Glu Glu Thr Gly
                325                 330                 335
```

Gly Gly Glu Cys Glu Arg Arg Glu Arg Gly Val Gln Trp Ser Glu Arg
            340                 345                 350

Leu Arg Glu Ala Phe Ser Pro Val Gly Phe Ser Asp Asp Val Val Asp
        355                 360                 365

Asp Val Lys Ala Leu Leu Lys Arg Tyr Lys Ala Gly Trp Ala Leu Val
    370                 375                 380

Leu Pro Gln Gly Asp His Glu Ser Gly Ile Tyr Leu Thr Trp Lys Glu
385                 390                 395                 400

Glu Pro Val Val Trp Ala Ser Ala Trp Lys Pro
                405                 410

<210> SEQ ID NO 7
<211> LENGTH: 1596
<212> TYPE: DNA
<213> ORGANISM: Arabidopsis thaliana

<400> SEQUENCE: 7

| | | | | | |
|---|---|---|---|---|---|
| atggatactc | tctttagact | agtcagtctc | caacaacaac | aacaatccga | tagtatcatt | 60 |
| acaaatcaat | cttcgttaag | cagaacttcc | accaccacta | ctggctctcc | acaaactgct | 120 |
| tatcactaca | actttccaca | aaacgacgtc | gtcgaagaat | gcttcaactt | ttcatggat | 180 |
| gaagaagacc | tttcctcttc | ttcttctcac | cacaaccatc | acaaccacaa | caatcctaat | 240 |
| acttactact | ctccttcac | tactcccacc | caataccatc | ccgccacatc | atcaccccct | 300 |
| tcctccaccg | ccgcagccgc | agctttagcc | tcgccttact | cctcctccgg | ccaccataat | 360 |
| gacccttccg | cgttctccat | acctcaaact | cctccgtcct | tcgacttctc | agccaatgcc | 420 |
| aagtgggcag | actcggtcct | tcttgaagcg | gcacgtgcct | tctccgacaa | agacactgca | 480 |
| cgtgcgcaac | aaatcctatg | gacgctcaac | gagctctctt | ctccgtacgg | agacaccgag | 540 |
| caaaaactgg | cttcttactt | cctccaagct | ctcttcaacc | gcatgaccgg | ttcaggcgaa | 600 |
| cgatgctacc | gaaccatggt | aacagctgca | gccacagaga | agacttgctc | cttcgagtca | 660 |
| acgcgaaaaa | ctgtactaaa | gttccaagaa | gttagcccct | gggccacgtt | tggacacgtg | 720 |
| gcggcaaacg | gagcaatctt | ggaagcagta | acggagagg | caaagatcca | catcgttgac | 780 |
| ataagctcca | cgttttgcac | tcaatggccg | actcttctag | aagctttagc | cacaagatca | 840 |
| gacgacacgc | ctcacctaag | gctaaccaca | gttgtcgtgg | ccaacaagtt | tgtcaacgat | 900 |
| caaacggcgt | cgcatcggat | gatgaaagag | atcggaaacc | gaatggagaa | attcgctagg | 960 |
| cttatgggag | ttccttcaa | atttaacatt | attcatcacg | ttggagattt | atctgagttt | 1020 |
| gatctcaacg | aactcgacgt | taaaccagac | gaagtcttgg | ccattaactg | cgtaggcgcg | 1080 |
| atgcatggga | tcgcttcacg | tggaagccct | agagacgctg | tgatatcgag | tttccgacgg | 1140 |
| ttaagaccga | ggattgtgac | ggtcgtagaa | gaagaagctg | atcttgtcgg | agaagaagaa | 1200 |
| ggtggctttg | atgatgagtt | cttgagaggg | tttggagaat | gtttacgatg | gtttagggtt | 1260 |
| tgcttcgagt | catgggaaga | gagttttcca | aggacgagca | acgagaggtt | gatgctagag | 1320 |
| cgtgcagcgg | gacgtgcgat | cgttgatctt | gtggcttgtg | agccgtcgga | ttccacggag | 1380 |
| aggcgagaga | cagcgaggaa | gtggtcgagg | aggatgagga | atagtgggtt | tggagcggtg | 1440 |
| gggtatagtg | atgaggtggc | ggatgatgtc | agagctttgt | tgaggagata | taaagaaggt | 1500 |
| gtttggtcga | tggtacagtg | tcctgatgcc | gccggaatat | tcctttgttg | gagagatcag | 1560 |
| ccggtggttt | gggctagtgc | gtggcggcca | acgtaa | | | 1596 |

<210> SEQ ID NO 8
<211> LENGTH: 530
<212> TYPE: PRT
<213> ORGANISM: Arabidopsis thaliana

<400> SEQUENCE: 8

```
Met Asp Thr Leu Phe Arg Leu Val Ser Leu Gln Gln Gln Gln Gln Ser
1               5                   10                  15

Asp Ser Ile Ile Thr Asn Gln Ser Ser Leu Ser Arg Thr Ser Thr Thr
            20                  25                  30

Thr Thr Gly Ser Pro Gln Thr Ala Tyr His Tyr Asn Phe Pro Gln Asn
        35                  40                  45

Asp Val Val Glu Glu Cys Phe Asn Phe Met Asp Glu Glu Asp Leu
    50                  55                  60

Ser Ser Ser Ser Ser His His Asn His His Asn His Asn Asn Pro Asn
65                  70                  75                  80

Thr Tyr Tyr Ser Pro Phe Thr Thr Pro Thr Gln Tyr His Pro Ala Thr
                85                  90                  95

Ser Ser Thr Pro Ser Ser Thr Ala Ala Ala Ala Leu Ala Ser Pro
            100                 105                 110

Tyr Ser Ser Gly His His Asn Asp Pro Ser Ala Phe Ser Ile Pro
            115                 120                 125

Gln Thr Pro Pro Ser Phe Asp Phe Ser Ala Asn Ala Lys Trp Ala Asp
130                 135                 140

Ser Val Leu Leu Glu Ala Ala Arg Ala Phe Ser Asp Lys Asp Thr Ala
145                 150                 155                 160

Arg Ala Gln Gln Ile Leu Trp Thr Leu Asn Glu Leu Ser Ser Pro Tyr
                165                 170                 175

Gly Asp Thr Glu Gln Lys Leu Ala Ser Tyr Phe Leu Gln Ala Leu Phe
            180                 185                 190

Asn Arg Met Thr Gly Ser Gly Glu Arg Cys Tyr Arg Thr Met Val Thr
        195                 200                 205

Ala Ala Ala Thr Glu Lys Thr Cys Ser Phe Glu Ser Thr Arg Lys Thr
    210                 215                 220

Val Leu Lys Phe Gln Glu Val Ser Pro Trp Ala Thr Phe Gly His Val
225                 230                 235                 240

Ala Ala Asn Gly Ala Ile Leu Glu Ala Val Asp Gly Glu Ala Lys Ile
                245                 250                 255

His Ile Val Asp Ile Ser Ser Thr Phe Cys Thr Gln Trp Pro Leu Leu
            260                 265                 270

Glu Ala Leu Ala Thr Arg Ser Asp Asp Thr Pro His Leu Arg Leu Thr
        275                 280                 285

Thr Val Val Val Ala Asn Lys Phe Val Asn Asp Gln Thr Ala Ser His
    290                 295                 300

Arg Met Met Lys Glu Ile Gly Asn Arg Met Glu Lys Phe Ala Arg Leu
305                 310                 315                 320

Met Gly Val Pro Phe Lys Phe Asn Ile Ile His Val Gly Asp Leu
                325                 330                 335

Ser Glu Phe Asp Leu Asn Glu Leu Asp Val Lys Pro Asp Glu Val Leu
            340                 345                 350

Ala Ile Asn Cys Val Gly Ala Met His Gly Ile Ala Ser Arg Gly Ser
        355                 360                 365

Pro Arg Asp Ala Val Ile Ser Ser Phe Arg Arg Leu Arg Pro Arg Ile
    370                 375                 380
```

| | | | | | | | | | | | | | | |
|---|---|---|---|---|---|---|---|---|---|---|---|---|---|---|
|Val|Thr|Val|Val|Glu|Glu|Glu|Ala|Asp|Leu|Val|Gly|Glu|Glu|Gly|
|385| | | |390| | | |  |395| | | |  |400|

Gly Phe Asp Asp Glu Phe Leu Arg Gly Phe Gly Glu Cys Leu Arg Trp
          405                 410                 415

Phe Arg Val Cys Phe Glu Ser Trp Glu Glu Ser Phe Pro Arg Thr Ser
          420                 425                 430

Asn Glu Arg Leu Met Leu Glu Arg Ala Ala Gly Arg Ala Ile Val Asp
          435                 440                 445

Leu Val Ala Cys Glu Pro Ser Asp Ser Thr Glu Arg Glu Thr Ala
    450                 455                 460

Arg Lys Trp Ser Arg Arg Met Arg Asn Ser Gly Phe Gly Ala Val Gly
465                 470                 475                 480

Tyr Ser Asp Glu Val Ala Asp Asp Val Arg Ala Leu Leu Arg Arg Tyr
              485                 490                 495

Lys Glu Gly Val Trp Ser Met Val Gln Cys Pro Asp Ala Ala Gly Ile
          500                 505                 510

Phe Leu Cys Trp Arg Asp Gln Pro Val Val Trp Ala Ser Ala Trp Arg
          515                 520                 525

Pro Thr
    530

<210> SEQ ID NO 9
<211> LENGTH: 2509
<212> TYPE: DNA
<213> ORGANISM: Oryza sativa

<400> SEQUENCE: 9

```
tgcaggattc ggcacgaggc acaactagct agtttagatc cccttttgcat ccatcgatga      60
tcagttgttg catcgatgat cagttgttgc aggacagtgt agtgaggtga aaagattgt      120
tgtagtagct gctgtgctgt atggtggtag ccagtgagta gctactacac tgcactgcag     180
tttgcacccc ggccatatgt tggctactac tactgcaggt gtcttaggtc tagatggata     240
ccctcttcag gttggttagc ctccaccacc atcaccacca ccagcacgcg gcctcaccgt     300
cgccgccgga ccagccgcac aagtcgtacc cctcctcgcg agggagcacc agctccccct     360
cctcccacca cacccacaac acacctact accaccactc ccactccac tacaacaata      420
atagcaacac caactactat taccagggtg gtggaggcgg cggcggaggg tactactacg     480
cggaggagca gcagccggcg gcgtacctag aagaatgcgg caacggccac cagttttaca     540
tggatgaaga cttctcctcc tcgtcttcct cccgccagtt ccactcggga acgggcgcgc      600
cgtcgtcggc gccggtgcct cctcctccgt cggcgacgac gtcgtccgcg ggcgggcacg     660
ggctgtttga ggcggcggac ttctcgttcc cgcaggttga tatcagcctc gacttcggcg     720
gctctccggc cgttccgtcg tcgtccggtg ctggcgccgg cgccggggca gcgccgtcgt     780
cgtcggggag gtgggcggcg cagctgctga tggagtgcgc gcgcgcggtg gcggggcgcg     840
acagccagcg cgtgcagcag ctcatgtgga tgctcaacga gctggcctcg ccgtacggcg     900
acgtcgacca gaagctggcc tcctacttcc tgcagggcct cttcgcgcgg ctcaccacct     960
ccggcccgcg cacgctgcgg acgctcgcca ccgtcgtcga ccgaacgcg tcgttcgact    1020
ccacgcgccg cacggcgctc aagttccagg agctcagccc gtggacgccg ttcgggcacg    1080
tcgccgccaa cggcgccata tcgagtcgt tcctggaggc gcggcggcg ggcgccgccg      1140
cctcctcctc ctcgtcgtct tcatcgtcga cgccgccgac gcggctgcac atcctcgacc    1200
tgagcaacac gttctgcacg cagtggccga ccctcctgga ggcgctggcc acccggtcct    1260
```

-continued

```
cggacgacac gccgcacctg tccatcacca ccgtcgtgcc cacggcggcg ccgtcggcgg   1320
ccgcgcagcg cgtgatgcgg gagatcgggc agcgcctcga gaagttcgcg cggctgatgg   1380
gcgtcccgtt cagcttccgc gccgtgcacc actcggggga cctggccgac ctcgacctcg   1440
ccgcgctgga cctccgcgag gcggcgcca ccgccgcgct cgccgtcaac tgcgtaaacg    1500
cgctgcgcgg ggtcgcgcgg gggcgcgacg cgttcgtggc gtcgctccgg cgcctggagc   1560
cgcgcgtggt caccgtcgtg gaggaggagg ccgacctggc ggcgccggag gcggacgcgt   1620
cgtcggaggc cgacaccgac gccgcgttcg tcaaggtgtt cggcgagggc ctccgcttct   1680
tctcggcgta catggactcg ctggaggaga gcttccccaa gacaagcaac gagaggctgt   1740
cactggagag ggcggtcggc cgtgccatcg tcgacctcgt gtcatgcccg gcctcccagt   1800
ccgccgagcg ccgggagacc gccgcgtcgt gggcgcggcg catgcggtcg gcggggttct   1860
cgccggcggc attcagcgag gacgtcgccg acgacgtgcg gtcgcttctc cggcggtaca   1920
aggagggctg tcgatgcgg gacgccgcg gtgccacgga cgacgccgcc ggcgccgctg    1980
ctgccggagc gttccttgcg tggaaggagc agcctgtcgt gtgggcgagc gcgtggaagc   2040
catgagatcg atcgatccaa caagtccaaa tccgccattg ctgcaaatca tcgagcctgc   2100
gatgcatcgt gcatgcaata cacaatatgg atcatgcata tcgcacgtgc gggttgaatg   2160
ggaagaggaa gcagcgcgcg cgtgtacgta cttagggttt ttcagccagc aacgtacgtg   2220
tgtagtaggg agaggaggta gcaaaacaca tcagatggat taagttaatc aatcaccagt   2280
tattactaga aaattaattt ggaggaatta attggcattt attgttcttg cataacatgt   2340
ttattaatta ttagatgctt cctctgatta ttaactttgt gaattcaggt gtgttcaatt   2400
taattttagc tagctagtag atatatcgat cctcaggtga tttatttgta gatctgaata   2460
ttccatgact tgtataggag ctactaatag tttatttgtt ttaccggtt               2509
```

<210> SEQ ID NO 10
<211> LENGTH: 603
<212> TYPE: PRT
<213> ORGANISM: Oryza sativa

<400> SEQUENCE: 10

```
Met Asp Thr Leu Phe Arg Leu Val Ser Leu His His His His His
1               5                   10                  15

Gln His Ala Ala Ser Pro Ser Pro Asp Gln Pro His Lys Ser Tyr
                20                  25                  30

Pro Ser Ser Arg Gly Ser Thr Ser Pro Ser His His Thr His
            35                  40                  45

Asn His Thr Tyr Tyr His His Ser His Ser His Tyr Asn Asn Asn Ser
        50                  55                  60

Asn Thr Asn Tyr Tyr Tyr Gln Gly Gly Gly Gly Gly Gly Gly Tyr
65                  70                  75                  80

Tyr Tyr Ala Glu Glu Gln Gln Pro Ala Ala Tyr Leu Glu Glu Cys Gly
                85                  90                  95

Asn Gly His Gln Phe Tyr Met Asp Glu Asp Phe Ser Ser Ser Ser
            100                 105                 110

Ser Arg Gln Phe His Ser Gly Thr Gly Ala Pro Ser Ala Pro Val
        115                 120                 125

Pro Pro Pro Pro Ser Ala Thr Thr Ser Ser Ala Gly Gly His Gly Leu
    130                 135                 140

Phe Glu Ala Ala Asp Phe Ser Phe Pro Gln Val Asp Ile Ser Leu Asp
```

```
            145                 150                 155                 160
        Phe Gly Gly Ser Pro Ala Val Pro Ser Ser Gly Ala Gly Ala Gly
                        165                 170                 175

Ala Gly Ala Ala Pro Ser Ser Gly Arg Trp Ala Ala Gln Leu Leu
                        180                 185                 190

Met Glu Cys Ala Arg Ala Val Ala Gly Arg Asp Ser Gln Arg Val Gln
                        195                 200                 205

Gln Leu Met Trp Met Leu Asn Glu Leu Ala Ser Pro Tyr Gly Asp Val
            210                 215                 220

Asp Gln Lys Leu Ala Ser Tyr Phe Leu Gln Gly Leu Phe Ala Arg Leu
        225                 230                 235                 240

Thr Thr Ser Gly Pro Arg Thr Leu Arg Thr Leu Ala Thr Ala Ser Asp
                        245                 250                 255

Arg Asn Ala Ser Phe Asp Ser Thr Arg Arg Thr Ala Leu Lys Phe Gln
                        260                 265                 270

Glu Leu Ser Pro Trp Thr Pro Phe Gly His Val Ala Ala Asn Gly Ala
                        275                 280                 285

Ile Leu Glu Ser Phe Leu Glu Ala Ala Ala Gly Ala Ala Ala Ser
            290                 295                 300

Ser Ser Ser Ser Ser Ser Ser Thr Pro Thr Arg Leu His Ile
        305                 310                 315                 320

Leu Asp Leu Ser Asn Thr Phe Cys Thr Gln Trp Pro Thr Leu Leu Glu
                        325                 330                 335

Ala Leu Ala Thr Arg Ser Ser Asp Asp Thr Pro His Leu Ser Ile Thr
                        340                 345                 350

Thr Val Val Pro Thr Ala Ala Pro Ser Ala Ala Ala Gln Arg Val Met
                        355                 360                 365

Arg Glu Ile Gly Gln Arg Leu Glu Lys Phe Ala Arg Leu Met Gly Val
                        370                 375                 380

Pro Phe Ser Phe Arg Ala Val His His Ser Gly Asp Leu Ala Asp Leu
        385                 390                 395                 400

Asp Leu Ala Ala Leu Asp Leu Arg Glu Gly Gly Ala Thr Ala Ala Leu
                        405                 410                 415

Ala Val Asn Cys Val Asn Ala Leu Arg Gly Val Ala Arg Gly Arg Asp
                        420                 425                 430

Ala Phe Val Ala Ser Leu Arg Arg Leu Glu Pro Arg Val Val Thr Val
                        435                 440                 445

Val Glu Glu Glu Ala Asp Leu Ala Ala Pro Glu Ala Asp Ala Ser Ser
        450                 455                 460

Glu Ala Asp Thr Asp Ala Ala Phe Val Lys Val Phe Gly Glu Gly Leu
        465                 470                 475                 480

Arg Phe Phe Ser Ala Tyr Met Asp Ser Leu Glu Glu Ser Phe Pro Lys
                        485                 490                 495

Thr Ser Asn Glu Arg Leu Ser Leu Glu Arg Ala Val Gly Arg Ala Ile
                        500                 505                 510

Val Asp Leu Val Ser Cys Pro Ala Ser Gln Ser Ala Glu Arg Arg Glu
                        515                 520                 525

Thr Ala Ala Ser Trp Ala Arg Arg Met Arg Ser Ala Gly Phe Ser Pro
                        530                 535                 540

Ala Ala Phe Ser Glu Asp Val Ala Asp Val Arg Ser Leu Leu Arg
        545                 550                 555                 560

Arg Tyr Lys Glu Gly Trp Ser Met Arg Asp Ala Gly Gly Ala Thr Asp
                        565                 570                 575
```

Asp Ala Ala Gly Ala Ala Ala Ala Gly Ala Phe Leu Ala Trp Lys Glu
            580                 585                 590

Gln Pro Val Val Trp Ala Ser Ala Trp Lys Pro
            595                 600

<210> SEQ ID NO 11
<211> LENGTH: 2359
<212> TYPE: DNA
<213> ORGANISM: Oryza sativa

<400> SEQUENCE: 11

| | | | | | |
|---|---|---|---|---|---|
| atggagaaag | caagcaaagc | aaaggcagag | gcagcaaaag | gcgcccacac | ccactgccgc | 60 |
| tgcctgctgc | tgctgccccc | gatggatacg | ctgtttaggt | tggttagcct | ccaagccgcc | 120 |
| tccgagcagc | agcagcagca | gcagcagtcg | gcgtcctaca | actcgaggag | cacgacgtcg | 180 |
| agcgggtcca | ggtcgtcgtc | gcaccagacg | aacgcgtcct | acagctacta | ccaccacagc | 240 |
| agcaacagcg | gcggcggcgg | cggaggcggc | ggagggtact | actacggcgg | ccagcagccg | 300 |
| ccgccgtcgc | agtactacta | cctggagccg | taccaagaag | aatgcggcaa | cgccccacac | 360 |
| caccagcttt | acatggatga | agacttctcc | tcctcgtcgt | cgtcgaggca | cttccaccac | 420 |
| ggcgcgcggg | tgcagcagca | gcagccgccg | gcgtcgtcca | cgcccacggg | gacggcgccg | 480 |
| acgccgccgc | tgtcgacctc | gtccaccgcg | gcgggcgccg | gcacggcct | gttcgaggcg | 540 |
| gcggacctgt | cgttcccgcc | ggacctcaac | ctcgacttct | cgtcccggc | gtcgtcgtcc | 600 |
| ggcggcggga | cagcgtcgtc | gggcgcggtt | gggggcggcg | gcggcgggag | gtgggctagc | 660 |
| cagctgctgc | tggagtgcgc | gcggtcggtg | gccgcccgcg | acagccagcg | cgtgcagcag | 720 |
| ctcatgtgga | tgctcaacga | gctcgcgtcg | ccgtacggcg | acgtggagca | gaagctggct | 780 |
| tcctacttct | tgcaggggct | gttcgctcgg | ctcacggcgt | ccgggccgcg | cacgctgcgc | 840 |
| acgctcgccg | cggcgtccga | ccggaacacg | tcgttcgact | cgacgcggcg | cacggcgctg | 900 |
| cggttccagg | agctcagccc | ctggtcctcg | tttgggcacg | tcgccgccaa | tggcgccatc | 960 |
| ctcgagtcct | tcctggaggt | cgccgccgcg | gcgtcgtcgg | agacgcagcg | gttccacatc | 1020 |
| ctcgacctga | gcaacacgtt | ctgcacgcag | tggccgacgc | tgctggaggc | gctggccacg | 1080 |
| cggtccgccg | acgagacgcc | gcacctctcg | atcaccaccg | tggtgtccgc | cgcgccgtcc | 1140 |
| gcgcccacgg | cggcggtgca | gcgcgtcatg | cgggagatcg | ggcagcgcat | ggagaagttc | 1200 |
| gcgcggctca | tgggcgtgcc | cttccgcttc | cgcgccgtgc | accactccgg | ggacctcgcg | 1260 |
| gagctcgacc | tcgacgcgct | cgacctccgc | gagggcggcg | ccaccaccgc | gctcgccgtc | 1320 |
| aactgcgtca | actcgctgcg | cggcgtggtt | cccggcaggg | cccgccggcg | cgacgcgttc | 1380 |
| gcggcgtcgc | tccgccggct | ggaccgcgcg | gtcgtcaccg | tcgtcgagga | ggaggcggac | 1440 |
| ctggtggcgt | ccgatcccga | cgcgtcgtcg | gcgacggagg | aaggcggcga | cacggaggcg | 1500 |
| gcgttcctca | aggtgttcgg | cgagggcttg | cgcttcttct | cggcgtacat | ggattcgctc | 1560 |
| gaggagagct | tccccaagac | gagcaacgag | aggctggcat | ggagaggggg | agcagggcgc | 1620 |
| gccatcgtcg | acttggtctc | gtgcccggcc | tcggagtcga | tggagcggcg | ggagacggcg | 1680 |
| gcgtcgtggg | cgcggcgcat | gcggtcggcc | gggttctctc | cggtggcatt | cagcgaggac | 1740 |
| gtcgccgacg | acgtgcgatc | gctgctgcgc | cggtacaggg | aagggtggtc | gatgcgcgag | 1800 |
| gccggcacgg | acgactcggc | ggccggagcc | ggcgtcttcc | tcgcgtggaa | ggagcagcct | 1860 |
| ctggtgtggg | caagcgcgtg | gcggccatga | tcggatcgtc | gtgatcgatg | gatcaaagct | 1920 |

```
caccggtgag tggaacagca tggaagaaaa gagctccata gctaagcaag cacgcatgca   1980
tatccaccat gcatgggta agctagcaag ctctctcgtg tgtgtcacga tcgacattaa   2040
tggcggctca cacaaaggca tgtagggttt tgaaacagcg taggaagcta cagaaatgga   2100
tcacgtacgt acgtacacat tgggttgcag cgatcgagga gggagatgat agttttagtt   2160
cctagatttg catccatttt tattcatcga tcgccaacaa gttcttggcg agaagatgat   2220
tttgatttgc ttgcttccat cttcttgttt attttccccc ctttcgtttg tgttcttct    2280 taatttgtaa gggttaacga catttttctt cactctggag aaattttacg tgcatggttt   2340
ttatcatgcg tacccgcaa                                                2359
```

```
<210> SEQ ID NO 12
<211> LENGTH: 629
<212> TYPE: PRT
<213> ORGANISM: Oryza sativa

<400> SEQUENCE: 12
```

Met Glu Lys Ala Ser Lys Ala Lys Ala Glu Ala Ala Lys Gly Ala His
 1               5                  10                  15

Thr His Cys Arg Cys Leu Leu Leu Pro Pro Met Asp Thr Leu Phe
                20                  25                  30

Arg Leu Val Ser Leu Gln Ala Ala Ser Glu Gln Gln Gln Gln Gln Gln
            35                  40                  45

Gln Ser Ala Ser Tyr Asn Ser Arg Ser Thr Thr Ser Ser Gly Ser Arg
        50                  55                  60

Ser Ser Ser His Gln Thr Asn Ala Ser Tyr Ser Tyr Tyr His His Ser
65                  70                  75                  80

Ser Asn Ser Gly Gly Gly Gly Gly Gly Gly Gly Tyr Tyr Tyr Gly
                85                  90                  95

Gly Gln Gln Pro Pro Pro Ser Gln Tyr Tyr Tyr Leu Glu Pro Tyr Gln
            100                 105                 110

Glu Glu Cys Gly Asn Ala Pro His His Gln Leu Tyr Met Asp Glu Asp
        115                 120                 125

Phe Ser Ser Ser Ser Ser Arg His Phe His His Gly Ala Arg Val
    130                 135                 140

Gln Gln Gln Gln Pro Pro Ala Ser Ser Thr Pro Thr Gly Thr Ala Pro
145                 150                 155                 160

Thr Pro Pro Leu Ser Thr Ser Thr Ala Ala Gly Ala Gly His Gly
                165                 170                 175

Leu Phe Glu Ala Ala Asp Leu Ser Phe Pro Pro Asp Leu Asn Leu Asp
            180                 185                 190

Phe Ser Ser Pro Ala Ser Ser Ser Gly Gly Gly Thr Ala Ser Ser Gly
        195                 200                 205

Ala Val Gly Gly Gly Gly Gly Arg Trp Ala Ser Gln Leu Leu Leu
    210                 215                 220

Glu Cys Ala Arg Ser Val Ala Arg Asp Ser Gln Arg Val Gln Gln
225                 230                 235                 240

Leu Met Trp Met Leu Asn Glu Leu Ala Ser Pro Tyr Gly Asp Val Glu
                245                 250                 255

Gln Lys Leu Ala Ser Tyr Phe Leu Gln Gly Leu Phe Ala Arg Leu Thr
            260                 265                 270

Ala Ser Gly Pro Arg Thr Leu Arg Thr Leu Ala Ala Ser Asp Arg
        275                 280                 285

Asn Thr Ser Phe Asp Ser Thr Arg Arg Thr Ala Leu Arg Phe Gln Glu

```
                    290                 295                 300
Leu Ser Pro Trp Ser Ser Phe Gly His Val Ala Ala Asn Gly Ala Ile
305                 310                 315                 320
Leu Glu Ser Phe Leu Glu Val Ala Ala Ala Ser Ser Glu Thr Gln
                325                 330                 335
Arg Phe His Ile Leu Asp Leu Ser Asn Thr Phe Cys Thr Gln Trp Pro
                340                 345                 350
Thr Leu Leu Glu Ala Leu Ala Thr Arg Ser Ala Asp Glu Thr Pro His
                355                 360                 365
Leu Ser Ile Thr Thr Val Val Ser Ala Ala Pro Ser Ala Pro Thr Ala
370                 375                 380
Ala Val Gln Arg Val Met Arg Glu Ile Gly Gln Arg Met Glu Lys Phe
385                 390                 395                 400
Ala Arg Leu Met Gly Val Pro Phe Arg Phe Arg Ala Val His His Ser
                405                 410                 415
Gly Asp Leu Ala Glu Leu Asp Leu Asp Ala Leu Asp Leu Arg Glu Gly
                420                 425                 430
Gly Ala Thr Thr Ala Leu Ala Val Asn Cys Val Asn Ser Leu Arg Gly
                435                 440                 445
Val Val Pro Gly Arg Ala Arg Arg Asp Ala Phe Ala Ala Ser Leu
450                 455                 460
Arg Arg Leu Asp Pro Arg Val Val Thr Val Val Glu Glu Ala Asp
465                 470                 475                 480
Leu Val Ala Ser Asp Pro Asp Ala Ser Ser Ala Thr Glu Glu Gly Gly
                485                 490                 495
Asp Thr Glu Ala Ala Phe Leu Lys Val Phe Gly Glu Gly Leu Arg Phe
                500                 505                 510
Phe Ser Ala Tyr Met Asp Ser Leu Glu Glu Ser Phe Pro Lys Thr Ser
                515                 520                 525
Asn Glu Arg Leu Ala Leu Glu Arg Gly Ala Gly Arg Ala Ile Val Asp
                530                 535                 540
Leu Val Ser Cys Pro Ala Ser Glu Ser Met Glu Arg Arg Glu Thr Ala
545                 550                 555                 560
Ala Ser Trp Ala Arg Arg Met Arg Ser Ala Gly Phe Ser Pro Val Ala
                565                 570                 575
Phe Ser Glu Asp Val Ala Asp Val Arg Ser Leu Leu Arg Arg Tyr
                580                 585                 590
Arg Glu Gly Trp Ser Met Arg Glu Ala Gly Thr Asp Asp Ser Ala Ala
                595                 600                 605
Gly Ala Gly Val Phe Leu Ala Trp Lys Glu Gln Pro Leu Val Trp Ala
                610                 615                 620
Ser Ala Trp Arg Pro
625

<210> SEQ ID NO 13
<211> LENGTH: 3157
<212> TYPE: DNA
<213> ORGANISM: Hordeum vulgare
<220> FEATURE:
<221> NAME/KEY: misc_feature
<222> LOCATION: 2406..2409, 2411, 2413, 2416..2417, 2508, 2846, 2848
<223> OTHER INFORMATION: n is a or g or c or t

<400> SEQUENCE: 13
attcggcacg aggcccagcc cccctacag gaaacagcat cgcactcccc ccaccacaac      60
```

```
ctcagaggcc accaacacac acacgcacct cttcccctct cccttcgcga tctctcttct    120
cgccgtcgcc gcacgaatcc tcctcgcctc gactccagct caagggtccg acgtacgtac    180
ggcgagccac cggccggagc tactgcgcag agattttcgt tccatctgga tttctgggct    240
agaagaaaga tccatgcagt gattagcgtg tcaagaatct ctactgaaca agtatggccg    300
atactccgac ttcccggatg atccacccct tcagcaacat gcagaggcag aacccgaagc    360
agttccagtt ccagtacccg acaacccac agcatccctg ccaccttac cagccatctc     420
cagacaccca cgtcgtgcca cagcatcact acagcctcaa gtctcactcg tcagatgcta    480
gctacgagaa ccatgttgct cagatgaagc acactctggt ggactcctcg gccgcggccg    540
gctgcatgag gcacgactcg ccctccagcc atagcttcac tcctccgtcc atcaggagcg    600
gcagtggcag cccttcgtct cacgacgaca gccactccga ctccacggac gggtctcctg    660
tcagtgcttc atgcgtcact gtgacgaccg aggatcctaa cgatctgaag cagaagctca    720
aggacctcga ggctgagatg cttgggccag acgccgctga gatagttaac agcctcgaga    780
gctcggtggc gaagcagctc tcgctggagc cggagaagtg ggcgcagatg atggactttc    840
ccaggggcaa cctcaaggag ctgctgcttg cttgtgccag agctgtggaa gagaagaaca    900
tgtacgcggt cgacgtgatg gtgccggagc tgaggaagat ggtttcggtc tccggtacgc    960
cgctcgagag gctgggagcc tacatggtgg aagggctcgt cgccaggctc gcctcctccg   1020
gccactccat ctacaaggcc ttgaggtgca aggagcccaa gagctccgac ctgctgtcct   1080
acatgcattt cctgtacgag gcctgccct acttcaagtt cggctacatg tcggccaacg    1140
gcgccatcgc ggaggccgtc aaggggaag acaggatcca cataatcgac ttccatatcg    1200
ctcaaggagc tcagtggatc tccctcctcc aggcccttgc ggccaggccc ggcggaccgc   1260
cgaccgtgag gatcaccggc attgatgact cggtgtcagc ctacgcgcga ggcggcgggc   1320
tggacctcgt tgggaggaga ctgtcgcaca tcgccggcct ctgcaaggtt ccctttgagt   1380
tccgctcggt cgccatggcc ggcgaggagg tggaggaggg gcacctcggg gtggtccccg   1440
gggaggcact ggcggtgaac ttcaccctgg agctgcacca catcccggac gagacggtga   1500
gcacggcgaa ccaccgggac cggatcctgc ggctggtgaa ggggctgagg cccaaggtgc   1560
tgaccctggt ggagcaggag tccaacacca acacggcccc gttcccgcag aggttcgccg   1620
agacgctgga ctactacacg gccatcttcg agtccatcga cctcacgctg cccagggacg   1680
acagggagcg ggtcaacatg gagcagcact gcctggcgag ggaggtggtg aacctgatcg   1740
cgtgcgaggg cgcggagcgg gtggagcgac acgaggtgtt cggcaagtgg aaggcgcgcc   1800
tcaccatggc cggcttcagg ccctcgccgc tcagctcgct ggtcaacgcc accatcagca   1860
agctgctgca gagctactcc gacaactaca agctcgccga gagggacggg gcgctctacc   1920
tcggctggaa gaagaggccc ctcgtggtct cgtccgcctg gcactagcgc tgcggtcgtc   1980
atatcatggc caactgcttt gtgaccatgc ttttcgtagg cgaatctaga tgcatgctta   2040
atgctttgct ggactatagg ggtgtcctgc tgatgctgtt gctgctgctg ctgctgtgga   2100
gaagaatagc tcctgtaacc tgttgttgta atgccgaact taggtctaaa agcctgaata   2160
tggctgatga gatgtagtgt aagttttac cgtatatgtt tcagttttat gtttcagttt     2220
cagacttcta atcgtaatct tgttgtctaa tcaaaaaaaa aaaaaaaaa aatctggggg    2280
ggggcccgg tacccaatc gcctttatg gggatcgtat ttacggccgc ttatggccgt     2340
tttttttaaa agttgggatt gggaaaaacc ctggggttac ccaaatttaa atccctttgg    2400
ggagannnng ngncgnnggg tttcccacca cgcagacggg taaaaaacat gggcggtcac    2460
```

-continued

```
ccaataatct atgtgttctc tgagatgcaa ccgatacgtc aaagcacnga tttaataact      2520
gatatttcac gtcattcatt aatacccctcg tgtacagcag tataatgaaa ctaacgatgt     2580
agcgtttgag agtttagtct gctggtacac tatcatgtac tagtaagttg cgtaagcgca     2640
ggggagctgg tagcactcat atcgacgttc tgcaccattg cgagtgtata tttctcagaa     2700
tctcactaca agaacccgtt tgtgtcatgt attgttctta gtatcgtaga agatatcgat     2760
cgagataatg tgattattca tacttatcgt gtagtctacg tgtgtaattt tacagatgca     2820
tgatgctaaa tagcgggtat ggcgcncntt ccattccttc tcttgttcta ccgtcggtct      2880
cctttggtga catacatata gtggttgttc actttcggta ttgacgttat cttataggac     2940
cgtgccatgt tcactccaat tgcatatcga tcaacgctca atatgcagat gcaatgttag    3000
tctcacatca catatcgtac catgctcgac gaaatgagct aactgttcgc ttccactata    3060
gtcagtcaca cttcgttacg ttgtatacgt acttatctgc atcatatatg cacgtagaac    3120
gcgtgatggg tgtaagcact atgattgttg ttacagt                              3157
```

<210> SEQ ID NO 14
<211> LENGTH: 557
<212> TYPE: PRT
<213> ORGANISM: Hordeum vulgare

<400> SEQUENCE: 14

```
Met Ala Asp Thr Pro Thr Ser Arg Met Ile His Pro Phe Ser Asn Met
1               5                   10                  15

Gln Arg Gln Asn Pro Lys Gln Phe Gln Phe Gln Tyr Pro Asp Asn Pro
            20                  25                  30

Gln His Pro Cys His Pro Tyr Gln Pro Ser Pro Asp Thr His Val Val
        35                  40                  45

Pro Gln His His Tyr Ser Leu Lys Ser His Ser Ser Asp Ala Ser Tyr
    50                  55                  60

Glu Asn His Val Ala Gln Met Lys His Thr Leu Val Asp Ser Ser Ala
65                  70                  75                  80

Ala Ala Gly Cys Met Arg His Asp Ser Pro Ser Ser His Ser Phe Thr
                85                  90                  95

Pro Pro Ser Ile Arg Ser Gly Ser Gly Ser Pro Ser Ser His Asp Asp
            100                 105                 110

Ser His Ser Asp Ser Thr Asp Gly Ser Pro Val Ser Ala Ser Cys Val
        115                 120                 125

Thr Val Thr Thr Glu Asp Pro Asn Asp Leu Lys Gln Lys Leu Lys Asp
    130                 135                 140

Leu Glu Ala Glu Met Leu Gly Pro Asp Ala Ala Glu Ile Val Asn Ser
145                 150                 155                 160

Leu Glu Ser Ser Val Ala Lys Gln Leu Ser Leu Glu Pro Glu Lys Trp
                165                 170                 175

Ala Gln Met Met Asp Phe Pro Arg Gly Asn Leu Lys Glu Leu Leu Leu
            180                 185                 190

Ala Cys Ala Arg Ala Val Glu Glu Lys Asn Met Tyr Ala Val Asp Val
        195                 200                 205

Met Val Pro Glu Leu Arg Lys Met Val Ser Val Ser Gly Thr Pro Leu
    210                 215                 220

Glu Arg Leu Gly Ala Tyr Met Val Glu Gly Leu Val Ala Arg Leu Ala
225                 230                 235                 240

Ser Ser Gly His Ser Ile Tyr Lys Ala Leu Arg Cys Lys Glu Pro Lys
```

```
                     245                 250                 255
    Ser Ser Asp Leu Leu Ser Tyr Met His Phe Leu Tyr Glu Ala Cys Pro
                260                 265                 270

Tyr Phe Lys Phe Gly Tyr Met Ser Ala Asn Gly Ala Ile Ala Glu Ala
                275                 280                 285

Val Lys Gly Glu Asp Arg Ile His Ile Ile Asp Phe His Ile Ala Gln
                290                 295                 300

Gly Ala Gln Trp Ile Ser Leu Leu Gln Ala Leu Ala Ala Arg Pro Gly
    305                 310                 315                 320

Gly Pro Pro Thr Val Arg Ile Thr Gly Ile Asp Asp Ser Val Ser Ala
                    325                 330                 335

Tyr Ala Arg Gly Gly Leu Asp Leu Val Gly Arg Leu Ser His
                340                 345                 350

Ile Ala Gly Leu Cys Lys Val Pro Phe Glu Phe Arg Ser Val Ala Met
                355                 360                 365

Ala Gly Glu Glu Val Glu Glu Gly His Leu Gly Val Val Pro Gly Glu
    370                 375                 380

Ala Leu Ala Val Asn Phe Thr Leu Glu Leu His His Ile Pro Asp Glu
    385                 390                 395                 400

Thr Val Ser Thr Ala Asn His Arg Asp Arg Ile Leu Arg Leu Val Lys
                    405                 410                 415

Gly Leu Arg Pro Lys Val Leu Thr Leu Val Glu Gln Glu Ser Asn Thr
                420                 425                 430

Asn Thr Ala Pro Phe Pro Gln Arg Phe Ala Glu Thr Leu Asp Tyr Tyr
                435                 440                 445

Thr Ala Ile Phe Glu Ser Ile Asp Leu Thr Leu Pro Arg Asp Asp Arg
    450                 455                 460

Glu Arg Val Asn Met Glu Gln His Cys Leu Ala Arg Glu Val Val Asn
    465                 470                 475                 480

Leu Ile Ala Cys Glu Gly Ala Glu Arg Val Glu Arg His Glu Val Phe
                    485                 490                 495

Gly Lys Trp Lys Ala Arg Leu Thr Met Ala Gly Phe Arg Pro Ser Pro
                500                 505                 510

Leu Ser Ser Leu Val Asn Ala Thr Ile Ser Lys Leu Leu Gln Ser Tyr
                515                 520                 525

Ser Asp Asn Tyr Lys Leu Ala Glu Arg Asp Gly Ala Leu Tyr Leu Gly
                530                 535                 540

Trp Lys Lys Arg Pro Leu Val Val Ser Ser Ala Trp His
    545                 550                 555

<210> SEQ ID NO 15
<211> LENGTH: 2318
<212> TYPE: DNA
<213> ORGANISM: Hordeum vulgare
<220> FEATURE:
<221> NAME/KEY: misc_feature
<222> LOCATION: (2271)..(2271)
<223> OTHER INFORMATION: n is a or g or c or t

<400> SEQUENCE: 15
atgaagcgcg agtaccagga cggcggcggg agcggcggtg ggggtgatga gatgggtcg        60 tcgagggaca agatgatggt gtcgtcgtcg gaggcggggg aggggagga ggtggacgag      120 ctgctggcgg cgctcgggta caaggtgcgg cgtccgaca tgcgacgt ggcgcagaag       180 ctggagcagc tcgagatggc catggggatg ggcggccccg ccccgacga cggcttcgcg      240
```

```
acccacctcg ccacggacac cgtccactac aaccccaccg acctctcctc ctgggtcgag      300
agcatgctgt ccgagctcaa cgcgccgccg ccgcccctcc cgccggcccc gccgcagctc      360
aacgcctcca cctcttccac cgtcacgggc ggcggcggat acttcgatct cccgccctct      420
gtcgactcct ccagcagcac ctacgccctg cgcccgatca tctcgccgcc cgtcgcgccg      480
gccgacctct ccgctgactc cgtccgggac cccaagcgga tgcgcactgg cggcagcagc      540
acgtcgtctt cgtcctcctc gtcgtcctcg ctcggcggtg gtgccgccag gagctctgtg      600
gtggaggctg ctccgccggt ggcggctgcg gctgctgcgc ccgcgctgcc ggtcgtcgtg      660
gtcgacacgc aggaggccgg gattcggctg gtgcacgcgc tgctggcgtg cgcggaggcc      720
gtgcagcagg agaacctctc ggccgccgag gcgctggtga agcagatacc cttgctggca      780
gcgtcgcagg gcggcgcgat gcgcaaggtc gcccccctact cggcgaggc cctcgcccgc      840
cgcgtcttcc gcttccgccc gcagccggac agctccctcc tcgacgccgc cttcgccgac      900
ctcctccacg cgcacttcta cgagtcctgc ccctacctca agttcgccca tttcaccgcc      960
aaccaggcca tcctggaggc gttcgccggc tgccgccgcg tccacgtcgt cgacttcggc     1020
atcaagcagg ggatgcagtg gccggcccttt ctccaggccc tcgcactccg tcccggcggg     1080
cccccttcgt tccgcctcac cggcgttggc cccccgcagc cggacgagac cgacgccctg     1140
cagcaggtgg gctggaagct cgcccagttc gcgcacacca tccgcgtcga cttccagtat     1200
cgcggcctct cgccgccac gctgcgcgac ctggagccgt tcatgctgca gccggagggc     1260
gaggaggacc ctaacgagga gcccgaggta atcgccgtga actcagtctt cgagatgcac     1320
cggctcctcg cgcagcccgg cgccctcgag aaggtcctgg gcacggtgcg cgccgtgcgg     1380
ccgaggatcg tcaccgtggt cgagcaggag gcgaaccaca actccggctc attcctggac     1440
cgcttcaccg agtccctgca ctactactcc accatgttcg attctctcga gggcggcagc     1500
tccggcggcc cgtccgaggt ctcatcgggg ggtgccgctc ctgccgccgc cgccggcacg     1560
gaccaggtca tgtccgaggt gtacctcggc cggcagatct gcaacgtggt ggcctgcgag     1620
ggcacggagc gcacagagcg gcacgagaca ctggggcagt ggcggaaccg gctgggcaac     1680
gccgggttcg agaccgtgca cctgggctcc aatgcctaca gcaggcgag cacgctgctg     1740
gccctcttcg ccggcggcga cgggtacaag gtggaagaga aggaagggtg cctgactctc     1800
gggtggcaca cgcgcccgct gatcgccact tccgcatggc cctcgccgc gccgtgatcg     1860
cgagttttga acgctgtaag tagacatcgt gagagcatgg agcgctacga cacaaccccg     1920
gccgccgcc cgccccggct ctccggcgca cgcacacgca cttgaagaag aagaagatga     1980
agaagaagct aaatgtcagt gatacgctga attgcagcga ccggctagga tcgatcgggt     2040
taccactcta cggtttggtt ctgcgtccgg cgtgaagaca tggacacgac caactccgac     2100
cagaccgccg gcatgtaatg taatccctcc ttcgttccca gttcaccatc acccgtaaaa     2160
ctccttatta agccctatta ctattattat tatgtttaaa tgtctattac tattgctatg     2220
tgtaattcct ccaatcgctc atattgaaat aagcacgggc cggacttttg ntagcaagct     2280
gcttcatttg agaattttg taccgcaagg gcacatct                              2318
```

<210> SEQ ID NO 16
<211> LENGTH: 618
<212> TYPE: PRT
<213> ORGANISM: Hordeum vulgare

<400> SEQUENCE: 16

Met Lys Arg Glu Tyr Gln Asp Gly Gly Gly Ser Gly Gly Gly Gly Asp

```
              1               5              10              15
            Glu Met Gly Ser Ser Arg Asp Lys Met Met Val Ser Ser Ser Glu Ala
                             20                  25                  30
            Gly Glu Gly Glu Glu Val Asp Glu Leu Leu Ala Ala Leu Gly Tyr Lys
                             35                  40                  45
            Val Arg Ala Ser Asp Met Ala Asp Val Ala Gln Lys Leu Glu Gln Leu
                50                      55                  60
            Glu Met Ala Met Gly Met Gly Gly Pro Ala Pro Asp Asp Gly Phe Ala
            65                      70                  75                  80
            Thr His Leu Ala Thr Asp Thr Val His Tyr Asn Pro Thr Asp Leu Ser
                                85                  90                  95
            Ser Trp Val Glu Ser Met Leu Ser Glu Leu Asn Ala Pro Pro Pro Pro
                            100                 105                 110
            Leu Pro Ala Pro Pro Gln Leu Asn Ala Ser Thr Ser Ser Thr Val
                        115                 120                 125
            Thr Gly Gly Gly Tyr Phe Asp Leu Pro Pro Ser Val Asp Ser Ser
                    130                 135                 140
            Ser Ser Thr Tyr Ala Leu Arg Pro Ile Ile Ser Pro Val Ala Pro
            145                 150                 155                 160
            Ala Asp Leu Ser Ala Asp Ser Val Arg Asp Pro Lys Arg Met Arg Thr
                            165                 170                 175
            Gly Gly Ser Ser Thr Ser Ser Ser Ser Ser Ser Ser Leu Gly
                        180                 185                 190
            Gly Gly Ala Ala Arg Ser Ser Val Val Glu Ala Ala Pro Pro Val Ala
                    195                 200                 205
            Ala Ala Ala Ala Pro Ala Leu Pro Val Val Val Asp Thr Gln
            210                 215                 220
            Glu Ala Gly Ile Arg Leu Val His Ala Leu Leu Ala Cys Ala Glu Ala
            225                 230                 235                 240
            Val Gln Gln Glu Asn Leu Ser Ala Ala Glu Ala Leu Val Lys Gln Ile
                            245                 250                 255
            Pro Leu Leu Ala Ala Ser Gln Gly Gly Ala Met Arg Lys Val Ala Pro
                        260                 265                 270
            Tyr Phe Gly Glu Ala Leu Ala Arg Arg Val Phe Arg Phe Arg Pro Gln
                    275                 280                 285
            Pro Asp Ser Ser Leu Leu Asp Ala Ala Phe Ala Asp Leu Leu His Ala
                290                 295                 300
            His Phe Tyr Glu Ser Cys Pro Tyr Leu Lys Phe Ala His Phe Thr Ala
            305                 310                 315                 320
            Asn Gln Ala Ile Leu Glu Ala Phe Ala Gly Cys Arg Arg Val His Val
                            325                 330                 335
            Val Asp Phe Gly Ile Lys Gln Gly Met Gln Trp Pro Ala Leu Leu Gln
                        340                 345                 350
            Ala Leu Ala Leu Arg Pro Gly Gly Pro Pro Ser Phe Arg Leu Thr Gly
                    355                 360                 365
            Val Gly Pro Pro Gln Pro Asp Glu Thr Asp Ala Leu Gln Gln Val Gly
                370                 375                 380
            Trp Lys Leu Ala Gln Phe Ala His Thr Ile Arg Val Asp Phe Gln Tyr
            385                 390                 395                 400
            Arg Gly Leu Val Ala Ala Thr Leu Ala Asp Leu Glu Pro Phe Met Leu
                            405                 410                 415
            Gln Pro Glu Gly Glu Glu Asp Pro Asn Glu Glu Pro Glu Val Ile Ala
                        420                 425                 430
```

Val Asn Ser Val Phe Glu Met His Arg Leu Leu Ala Gln Pro Gly Ala
        435                 440                 445

Leu Glu Lys Val Leu Gly Thr Val Arg Ala Val Arg Pro Arg Ile Val
    450                 455                 460

Thr Val Val Glu Gln Glu Ala Asn His Asn Ser Gly Ser Phe Leu Asp
465                 470                 475                 480

Arg Phe Thr Glu Ser Leu His Tyr Tyr Ser Thr Met Phe Asp Ser Leu
                485                 490                 495

Glu Gly Gly Ser Ser Gly Gly Pro Ser Glu Val Ser Ser Gly Gly Ala
            500                 505                 510

Ala Pro Ala Ala Ala Ala Gly Thr Asp Gln Val Met Ser Glu Val Tyr
        515                 520                 525

Leu Gly Arg Gln Ile Cys Asn Val Val Ala Cys Glu Gly Thr Glu Arg
    530                 535                 540

Thr Glu Arg His Glu Thr Leu Gly Gln Trp Arg Asn Arg Leu Gly Asn
545                 550                 555                 560

Ala Gly Phe Glu Thr Val His Leu Gly Ser Asn Ala Tyr Lys Gln Ala
                565                 570                 575

Ser Thr Leu Leu Ala Leu Phe Ala Gly Gly Asp Gly Tyr Lys Val Glu
            580                 585                 590

Glu Lys Glu Gly Cys Leu Thr Leu Gly Trp His Thr Arg Pro Leu Ile
        595                 600                 605

Ala Thr Ser Ala Trp Arg Leu Ala Ala Pro
    610                 615

<210> SEQ ID NO 17
<211> LENGTH: 120
<212> TYPE: PRT
<213> ORGANISM: Populus trichocarpa

<400> SEQUENCE: 17

Met Asp Thr Leu Phe Arg Leu Val Ser Leu Gln Gln Gln Ser Glu Gln
1               5                   10                  15

Ser Phe Asn Ser Thr Ser Arg Thr Ser Ser Ser Ser Arg Ser Ser Arg
            20                  25                  30

Gln Asn Asn Asn His His His His Tyr Gln Gln Glu Asp Glu Glu
        35                  40                  45

Cys Phe Asn Phe Phe Met Asp Glu Glu Asp Phe Ser Ser Ser Ser Ser
50                  55                  60

Lys His Tyr Tyr Pro Pro Tyr His His Asn Gln Gln Gln Gln His Gln
65                  70                  75                  80

His Gln Thr Thr Thr Thr Thr Pro Thr Thr Thr Thr Asn Thr Ser
                85                  90                  95

Thr Pro Ser Thr His His Val Leu Asp Ser Ala Asp Phe Ser Phe Ser
            100                 105                 110

Pro Ser His Asp Leu Asn Phe Glu
        115                 120

<210> SEQ ID NO 18
<211> LENGTH: 25
<212> TYPE: PRT
<213> ORGANISM: Populus trichocarpa
<220> FEATURE:
<221> NAME/KEY: VARIANT
<222> LOCATION: (7)..(7)
<223> OTHER INFORMATION: Xaa is Asn or Gln
<220> FEATURE:

```
<221> NAME/KEY: VARIANT
<222> LOCATION: (21)..(21)
<223> OTHER INFORMATION: Xaa is Lys or Glu
<220> FEATURE:
<221> NAME/KEY: VARIANT
<222> LOCATION: (22)..(22)
<223> OTHER INFORMATION: Xaa is Phe or Leu
<220> FEATURE:
<221> NAME/KEY: VARIANT
<222> LOCATION: (23)..(23)
<223> OTHER INFORMATION: Xaa is Asn or Lys

<400> SEQUENCE: 18

Val Met Lys Glu Ile Gly Xaa Arg Met Glu Lys Phe Ala Arg Leu Met
1               5                   10                  15

Gly Val Pro Phe Xaa Xaa Xaa Val Ile
            20                  25

<210> SEQ ID NO 19
<211> LENGTH: 24
<212> TYPE: PRT
<213> ORGANISM: Populus trichocarpa
<220> FEATURE:
<221> NAME/KEY: VARIANT
<222> LOCATION: (5)..(5)
<223> OTHER INFORMATION: Xaa is Gly or Ala
<220> FEATURE:
<221> NAME/KEY: VARIANT
<222> LOCATION: (11)..(11)
<223> OTHER INFORMATION: Xaa is Thr or Cys
<220> FEATURE:
<221> NAME/KEY: VARIANT
<222> LOCATION: (12)..(12)
<223> OTHER INFORMATION: Xaa is Glu or Asp
<220> FEATURE:
<221> NAME/KEY: VARIANT
<222> LOCATION: (18)..(18)
<223> OTHER INFORMATION: Xaa is Tyr or His

<400> SEQUENCE: 19

Leu Asn Glu Leu Xaa Ser Pro Tyr Gly Asp Xaa Xaa Gln Lys Leu Ala
1               5                   10                  15

Ser Xaa Phe Leu Gln Ala Leu Phe
            20

<210> SEQ ID NO 20
<211> LENGTH: 15
<212> TYPE: PRT
<213> ORGANISM: Populus trichocarpa
<220> FEATURE:
<221> NAME/KEY: VARIANT
<222> LOCATION: (10)..(10)
<223> OTHER INFORMATION: Xaa is Thr or Ala

<400> SEQUENCE: 20

Leu Lys Phe Gln Glu Val Ser Pro Trp Xaa Thr Phe Gly His Val
1               5                   10                  15

<210> SEQ ID NO 21
<211> LENGTH: 14
<212> TYPE: PRT
<213> ORGANISM: Populus trichocarpa

<400> SEQUENCE: 21

Cys Thr Gln Trp Pro Thr Leu Leu Glu Ala Leu Ala Thr Arg
1               5                   10

<210> SEQ ID NO 22
<211> LENGTH: 2564
```

<212> TYPE: DNA
<213> ORGANISM: Arabidopsis thaliana

<400> SEQUENCE: 22

```
agatttcgag aaattacata agaaactgaa ttgcaacact cgataggttt cgaagaaagg      60
gacaaagaag cagagcgtgg ggtttcttct aataattgta aagaaactg atcatgagaa      120
catttgatct accagagatg gtgatgactc ataagatgta aatatctact gcattatgtc     180
tagcctaggc tataatgtag atttgatcac tttcttcatt aattagtttg gaattttagc    240
atgatatagc atatatctaa atatgtccga aactttccta catactagaa aatatggaga    300
gttatgtaat gtaggtttgc ttgttaatat acaaaataac atcatcattt agttttaga    360
ttttttattt tatttttat aatggtgcta cgtacgtggc gatcaaatta ttccaatttt    420
gagacttcgg gattttaaac gaaattaaac aatgggcatg agctcggggg gatagacaag   480
attaatgctt tgtatcgaga caaacgagaa atcatgatg agcctatgca ttaagtgccg    540
ttggttaatt agaggttcgc atatacataa accagtagac atatggataa atatgaacac   600
acacaccaaa aagtgggaa atctaaataa gtgtagagaa taataagtcc tcaggtggga    660
gattcaaaga gaggacaatg aagggtatat agactctaaa caaaaatggc atgacttagt    720
ggagagggtt ttaaattgaa acaagtagga ttgaagaaca agaaaacaaa gaagcatgcc   780
ctagatttct gagataataa ttacacattg ctgtttatat aaggtaagag aatatgacac    840
attggttggt ttcttacggg taaatgtgaa gaaaaaaaaa tagtaatatt tgagaaaatc    900
taaaatagta aagaggtata tatggagaag aagagagaaa agggaaaaat agtggcagag    960
aatggagaga ggttaggagg caaaggcaaa tgtggagctt tgatgatgtt gatgcacgcc   1020
gtcagctttt cttcacgcct gctcccactc actcacacct atgaacattc tctctctatt    1080
ttataattat attcacatgt ctctatgtta ctatgtaaat ggtgaccact taagtattta   1140
tatatcatgt atatatctta taggtatcat acaaaatggt catgaaactt ttgcaatttc    1200
aatctacttg ttcattgtag atgctagctt ttcacatgtt ttgaaaatta gtctggatct   1260
gaaattcttt aattagcatt gttttgttgg tcaacgtttta atttcttgat tattgatgtc   1320
aaaaattcag agcgttcaga actcttacac taatttctta aaaataatcg attaagagaa   1380
aatagagttt tcatgcacca gtgttgatag taacgtagtc gcggaatgtc taaaacgatt   1440
atgagtttgg tgttttgatt ggttagaatt ggtattagta ggacattcta acttttttgt    1500
tagtctgttg atttaggatg cgtaaagagt cttttttattt tacaccagtt gagacttggg   1560
atcgatagta cttgaaacac ttggttggtt tcatgtattt ggcctatata taaacaaaca   1620
tcgtaattat atacggattt ttttcggaat tttacgccat atctgtaagt atatataaca    1680
tgcatgtcgt tttcaaattc atatgatgaa cgatccacgt aagtgctact actcctacaa    1740
tattgcatga gagagatatg tatttataaa ttttattttg aagaagaaat aagagggaag    1800
gttacttggg tggatcgatg tgaaaacaaa agaagaaaaa gcgaaaccca ctaagccatt    1860
acatgatatc gaccttctta tcttttttcct ctttattttta tttttctcag acttttttc    1920
tacttaatga aacctccaaa ctatctaact aatacactcc catgtagaat aaagaaaatt   1980
atataagata ttgttgatat tttgtaacta gaaatatat ttgctctgta atttttcgta    2040
agttaaatca acatttttca gtagaaacaa atattactgc aaaaagtagg atcattattt    2100
ttgtccaaaa tctcagttag ctataggggtt gtagtaaaaa caaacacat tcttgatttg    2160
ccccaaaaaa taagagaga gaagaatatt gttcaaaagt ggtctcttct ctctctaatt     2220
```

| | |
|---|---:|
| atgtttttcac taaacccaat tagattcaaa cagtctacaa agtccaaaag ataaacatgg | 2280 |
| gacaacaatt cgatgcaaaa aatcctctttt tcatgctctt tttttattct ctagtctttt | 2340 |
| aaattactaa taaaaactca caaatccacc aaacccattc tctacaactc accttcatct | 2400 |
| agatttaccc actcccaccg agaaacacaa gaaaaaaaat atacatatat aaatatacaa | 2460 |
| gacaacacat gatgctgatg caatatacac aacaaagtat taaatcttag atattgtggg | 2520 |
| tctcccttttc ttctattcat tttcttattc attaaaaaaa aaaa | 2564 |

<210> SEQ ID NO 23
<211> LENGTH: 2549
<212> TYPE: DNA
<213> ORGANISM: Populus trichocarpa

<400> SEQUENCE: 23

| | |
|---|---:|
| aaatcaataa aaaacaaaa taaataacaa tcaaagaat gaccaaatta gatataaaag | 60 |
| aacaaataaa atgaaacatt tatattttgg caaggagaaa aggagaaaaa tagggaggag | 120 |
| aagaaataaa tattcaatcg gagcaaatca ttacactgtc atgtacacgc gtcagactat | 180 |
| tgaatagagg atggcaggat gcttccatct ttgccatgaa aaccggtgtt tggagggtag | 240 |
| ataatgcctt aaacattgcc taaaaggcag gggtatcgtc caacgcccgc accaaccact | 300 |
| ttttatttttt aactaatatc taaatttatc aaaataccaa atcgcttcca agtcaacttg | 360 |
| ataattacta aaaacatatt atgaaatgac caaaagcac ttgaataata gtttgaaaat | 420 |
| ttttgcttttt aaaggtaatt tagtctttat attatatttt tgaaatgtaa aaagatcaaa | 480 |
| ttacccttga tcaatatttt tagaaaattt gtttttaagg gtaataaagt ttttaaaata | 540 |
| tgcatttaaa aggttaaaag accaaattat tccataagaa aaaaaccgtt ttacttccaa | 600 |
| tagcaagtta attgattttt ttgttggaag gggaaaaatat aattcacta ttatagtgaa | 660 |
| catggctttc aatttatttt ttatttaaag ggtcctttgt ctcaattctg ataaaaaaag | 720 |
| ttagtatttt ctacttttaa aaatattata agttttattt tcaattatga atgttataat | 780 |
| aattaaaaaa tatatatgat ataggtgtaa tgctattata gaaaaatat aaaataaatt | 840 |
| acctaccttt ttatcttcta ctcacaaaaa aaaattaaaa tagttttttt taaatagatt | 900 |
| tatgcttgtt ctattttttt taatagatgt acttatgtga gagtaagcgg caataaattt | 960 |
| gaaacaaaat tagtgagatc acctttattc aaataataag accgggtcac cgggtcatat | 1020 |
| atatatatat atatatatat atatatatat atatatatat atatatatat atatgcttgc | 1080 |
| agtcaacaat aatgatttcc aatttttattt aaaccgaatg atctacacga gacagaatcc | 1140 |
| agacgtgata gttttcctaa tgattgatgg agaaaaccaa ggacgagcag tgattaggaa | 1200 |
| caaggaaaat ttcaacagac aaaagaaact catatatata tatatagaca cacactctca | 1260 |
| cctcttgcgt atgaaaatgt agaatagcaa tagagcataa tgttgctgac tataaaagca | 1320 |
| aagagtagac caaccgtgac atacattaaa atccaaatat ttgatctgcg ttgaggttta | 1380 |
| gcaagctgac acagaaagaa ataaatgttt gtgcctagct atatgtaggc caaccaaata | 1440 |
| tagatatagt ttctagagag aattaaggtt cagcttgagg acaacaaggt taagacaata | 1500 |
| aaaggcgaag tagtacgtgg ttgtggtgta atcataatga accggcttgg ctatgaattt | 1560 |
| tgactaaaaa aagagcaagt cactagcggg agtaagattt gaggttgtga catggaagga | 1620 |
| gagcctagct atatatggtt gggccatctt gagaaatggc ctagctagct agtttggtgc | 1680 |
| atatatggtg tatggaatga atggatttat aataagtgtt tgctatatat atatatatat | 1740 |
| atatatatat atatatatat atatatataa actaaactat catgtggaag tggggaaaaa | 1800 |

-continued

```
agtgaaagag cacgccctag attttatat tacaaaagag cattggttat aattaaatgg    1860
aagttgattt atgttacaca gtgtagaaaa ggcaaaagcg gggtggaatt ttggcagaga    1920
ttgaagaggg attaggaggc aaggaatgtg aataggatgg gttggaggga tgatagtggg    1980
tttgataatg atgatgcacg ccggcagctt tactcattta tcttcccaaa atccaattgg    2040
cacgcctgcc cccactaaaa cctataacaa tattctcttc tctctttcaa tctttctcat    2100
agacaatgaa aagctaatcc actaacccat ttggtgatct agctagacct tgttatcttt    2160
ctctttttta atcttttgt cagataacat ttctatttct caacaccagt agctctttca     2220
tgccaacttc ccacgttctt ccagggaaaa cgtatattag tcatatctct catgagttga    2280
ttaaaaaaga aggaaaaaa gggagaagac tgggctagct agctagataa aagaatatcc     2340
caaaccccac ccaatttgat tcacatcgac tacagaaaaa gaaaagcaca tttaaacatg    2400
tatgtatgta tatatatgta tatatataaa tatccaactt caagatcctc tcttttatca    2460
ttctctaccc caatattccc acagttaaaa acacaaacac ccatcccctt accttcactc    2520
caagccatcc ccaacaaact ccatccgaa                                      2549

<210> SEQ ID NO 24
<211> LENGTH: 1533
<212> TYPE: DNA
<213> ORGANISM: Populus trichocarpa

<400> SEQUENCE: 24
atggatacct tgtttaggct agttagtctc caacaacaat ctgaacaatc tttcaactct     60
actagcagaa cctctagtag ctctagatca tcaagacaaa acaacaacca ccaccatcat    120
cactatcaac aagaagacga agaatgcttc aacttttttca tggatgagga agacttctct    180
tcatcttctt ctaagcacta ctatcctcct tatcaccaca accaacaaca acaacatcaa    240 caccaaaacca ccaccaccac tcctaccact actaccacca cactagcac ccctttctact    300 caccatgtcc ttgattccgc tgacttctct ttctccccctt ctcatgacct aaactttgaa    360
ttttccggca gtgggtcac cgatatcctc cttgaatctg cacatgccat cgcggataaa    420
aacagcgctc gtctccagca attgatgtgg atgcttaatg agcttggttc accttatggt    480
gacacagagc aaaaacttgc ttcttatttt ctccaagctt tgtttagccg catgaacgac    540
tccggcgaga gatgctaccg tactttagct tcagcatcag agaaaacttg ctcttttgat    600
tccacaagga aaatggtatt aaagtttcaa gaggtgagtc cttggactac ttttggtcac    660
gtatcttgta atggcgcaat tatggaagca tttgaaggtg aaagcaaatt gcatattatt    720
gatattagta acacatattg tacccaatgg cctactttgc tcgaagccct agcaactcgc    780
actgatgaga caccacactt gaagttaacc accgtagtgg ctagcaaaag tagtggtaat    840
aatattggtt taactagtac aggaggttta gcttcagttc ataaggtaat gaaagaaatt    900
ggcaacagaa tggaaaaatt tgccaggctt atgggagtcc catttaagtt taatgttatc    960
caccatgctg gtgatttatg tgacctaaac ttagctgaat tggatgttaa agatgatgag   1020
gctcttgcta tcaactgtgt tggtgctta cactcaatca ctccagcttc tcgtcgccga    1080
gattatgtta tatctagttt tagaacattg caaccaagaa tcattactgt tgttgaagaa   1140
gaagctgatc ttgatggtct ggattttgtc aagggttttc aagaatgttt aagatggttt   1200
agggtttact ttgaatcatt ggatgagagc tttccaagaa ccagtaacga acagttgatg   1260
cttgaaagag cagcaggccg cgctatcgtt gacttagtgg catgtcctcc atctgattcg   1320
```

| | |
|---|---|
| atcgaaaggc gggaaacagc cacgcgctgg tctggacgcc tccattcatg tggttttagc | 1380 |
| ccgataattt tcagtgatga ggtttgtgat gatgtacgcg ccttattgag gaggtataag | 1440 |
| gagggttggt caatgacaca gtgcggggat gccggaatat tcttgtgctg gaaggaacag | 1500 |
| ccggtggtgt gggctagtgc atggaggccc tga | 1533 |

<210> SEQ ID NO 25
<211> LENGTH: 1243
<212> TYPE: DNA
<213> ORGANISM: Populus trichocarpa

<400> SEQUENCE: 25

| | |
|---|---|
| atgcaaagca atagcagcaa caacaacaac aatcagcctc agactagtca tacatcaaca | 60 |
| agccgttctt cggactccgg tgaggcttgt ggggcaggaa acaaatgggc atcaaggctt | 120 |
| cttagtgagt gtgcaagagc aatctcagag aaggactcta gcaagatcca taaccttcta | 180 |
| tggatgttaa atgagcttgc ctctccttat ggagattgtg aacagaaatt ggcatctcat | 240 |
| ttcttgcaag ctctcttttg taaggctacc gactccggcc aacggtgctt caaaacccta | 300 |
| acaacagtag ctgaaaagag ccactccttt gattcagcta ggaaattgat actaaaattc | 360 |
| caagaggtaa gcccatggac tacttttggt catgtggctt caaacggtgc aattttggag | 420 |
| gccttagatg gggcgagcaa acttcacata attgatataa gccataccct ttgcacacaa | 480 |
| tggcctactt tgctagaagc tttagctaca agaaatgatg agacgccgca tttaaagctc | 540 |
| accgttgtgg taactgctag cattgtaaga tcggtcatga agaaattgg ccaaagaatg | 600 |
| gagaagtttg ctaggttaat gggagtgccc tttgagctta atgtaattag tgggctaaac | 660 |
| catttaggag agctcacaaa ggacaggcta ggagttcaag aagatgaagc tgtcgcgatt | 720 |
| aattgcaatg gggcattgag aagagttgga gtagaggaaa gaaattctgt gatccagatg | 780 |
| tttcaatcac ttaaccctcg agttgtgaca attgttgaag aagaagctga ttttactagc | 840 |
| tcaagatatg actttgtcaa gtgctttgaa gagtgcctta ggtattatac actatatttt | 900 |
| gagatgctag aggagagctt tgtcccaact agtaatgaga gattgatgtt ggagagggaa | 960 |
| tgttcaagga acatagttag agttttggct tgtgatgaag gaaatgatgg aggagagtgt | 1020 |
| gaaagaaggg agaggggaag ccaatggttt gaaaggctaa gggaggcatt tcccctgtt | 1080 |
| gggttcagtg atgatgttgt cgatgatgtc aaggcattgc ttaagagata ccgagctggg | 1140 |
| tgggcactag tgctacctca aggagatcat gactcaggaa tttacttaac atggaaagaa | 1200 |
| gaacctgtgg tatgggcttc tgcatggaaa ccctagagga gaa | 1243 |

<210> SEQ ID NO 26
<211> LENGTH: 1236
<212> TYPE: DNA
<213> ORGANISM: Populus trichocarpa

<400> SEQUENCE: 26

| | |
|---|---|
| atgcaaagca atagcagcaa caacaacaat aatcagcctc aaaccagcca tacatcaaca | 60 |
| agccggtctt cggactccgg tgaggcctgt ggaggaggaa acaagtgggc atcaaagctt | 120 |
| cttagtgagt gtgcaagagc aatctcagag aaggactcta gcaagatcca ccaccttcta | 180 |
| tggatgttaa atgagcttgc ctctccttat ggagattgtg atcagaaatt ggcatcttat | 240 |
| ttcttgcaag ctctcttctg taaggctacc gagtctggtc aacggtgttt caaaacccta | 300 |
| acaacagtag ctgaaaagag ccactccttt gattcagcta ggaaattgat actaaaattc | 360 |
| caagaggtaa gcccgtggac tactttcggt catgtagctt caaatggtgc aattttggag | 420 |

```
gccttagatg gggaaagcaa acttcacata attgatatca gcaatacccct ttgcacacag    480 tggcctactt tgctagaagc tttagccaca agaaatgatg agacgccgcg attaaagctc    540
accgttgtgg taactgctag cattgtaaga tcagtcatga agaaattgg ccaaagaatg      600 gagaagtttg ctaggttaat gggagtgccc tttgagttta agtaattag tgtgctaaat    660 catataggag agctcacaaa ggaaggactg ggtgttcaag aagatgaagc agtcgcgatt    720
aattgcattg gggcattgag aagagttgaa gtagatgaaa gaagttctgt aatccagttg    780
ttccgatcac ttaaccctcg agttgtgaca attgtagagg aagaagctga ttttactagc    840
tcaagatatg acttcgtcaa gtgctttgaa gagtgcctga ggtattatac actatatttt    900
gagatgctag aggagagctt tgtcccaact agtaatgaga gattgatgtt ggagagggaa    960
tgttcaagga acatagttag ggttttggct tgtgatgaag aaactggtgg aggagagtgt    1020
gaaagaagag agcggggtgt ccaatggtct gaaaggctaa gggaggcatt tcccctgtt    1080 ggattcagtg atgatgttgt cgatgatgtc aaggcattgc ttaagagata caaagctggg    1140
tgggcacttg tgctacctca aggagatcat gagtcaggaa tttacctaac atggaaagag    1200
gaacctgtag tatgggcttc tgcatggaaa ccctaa                              1236
```

<210> SEQ ID NO 27
<211> LENGTH: 1638
<212> TYPE: DNA
<213> ORGANISM: Artificial sequence
<220> FEATURE:
<223> OTHER INFORMATION: Synthetic sequence: Consensus sequence from
      Figure 2 of PCT/IB2008/001482
<220> FEATURE:
<221> NAME/KEY: misc_feature
<222> LOCATION: (1)..(1638)
<223> OTHER INFORMATION: n = a, t, g, or c

<400> SEQUENCE: 27

```
atggatacnn tntttagnct agtnagtctc caacaacaan nnnnntcnga nannatcntt      60
ncaantcnan ctnnnnnnag cagaacntcn annancncta nnnnntcnnn acaaannnnn     120
nancacnacn annntcnnna nnannangnn gncgaagaat gcttcaactt tttcatggat    180
gangaagacn tntcntcntc ttcttctnan cacnacnatc nnnnnnnnnn nnntcctnat    240
nnnnacnacn cnnccnnnnac nacnncnacn cnanaccann ccnccacanc ancaaccnct    300
acnaccacca ccacnnncnc agccttagac tcgccatann cntcatccng cnnnnnnnnt    360
gacnnntncn cgttctccnn anctcangnn cctnagncct ttgaattntc agncaannnn    420
nngtgggcan ccnagntcct tcttgaatct gcacgtgcca tctcnganaa agacactgcn    480
cgtntccanc aantnctatg gatgctnaat gagcttgctt ctccttatgg agacacngag    540
caaaaactgg cttcttattt cctccaagct ctcttcagcc gcatgaccga ctccggcgaa    600
cgatgctacc gaacntnnn nnnagctnca gcancagaga agacttgctc ctttgattca    660
acnaggaaaa tggtactaaa gttccaagag gtnagcccnt ggactacttt tggtcacgta    720
gcttcaaacg gngcaatttt ggaagcatta ganggngaaa gcaaantnca catnattgat    780
ataagcaaca cnttttgcac ncaatggcct actttgctag aagctttagc cacaagaact    840
gatgagacgc cncacttaaa gctaaccacn gtngtnnnn nnnnnnnng tggnnannan      900 nttngtnnaa cnngtncaag cggtgtagca tcagttnnnn nnnnatgaa agaaattggc     960 aacagaatgg agaaatttgc taggcttatg ggagtnccnt ttaagtttaa tgttattcat    1020
cangttggtg atttatgtga gctnaanntn gacgaactgg atgttaaaga agatgaagct    1080
```

```
ntngcnatta actgcgttgg ngcnttgcan ngaatcgctn cagntgnaag ncnnngagat    1140
tctgtgatat cgagtttccg ancattnaaa ccnagaattg tgacngttgt agaagaagaa    1200
gctgatcttg ntggnnnann annnnntgga ttttgtcaag ngttnnnnnn nnnnnttgaa    1260
gaatgtttaa gatggtttag ggtttacttt gagtcattgg angagagctt tccaagaacn    1320
agtaacgaga ggttgatgct ngagagngca gcnggacgng cnatcgttga nnttgtggct    1380
tgtgatccgt cggattcgat ggagaggcgn gagacagcna ggagctggnn ntcnagnngn    1440
ctgaannnnt gtgggnnnnn tttngcccgg tnggttcag  tgatgaggtt gnngatgatg    1500
tcagngcntt gttgaggaga tataaagang gtnnntggtc aatggtacag tgtcnnggnn    1560
nnnntgacgc cggaatattc ctntgntgga aagaacagcc ggtggtntgg gctagtgcat    1620
ggaggccctn annnnnnn                                                   1638
```

<210> SEQ ID NO 28  
<211> LENGTH: 531  
<212> TYPE: PRT  
<213> ORGANISM: Arabidopsis thaliana

<400> SEQUENCE: 28

```
Met Asp Thr Leu Phe Arg Leu Val Ser Leu Gln Gln Gln Gln Gln Ser
1               5                   10                  15

Asp Ser Ile Ile Thr Asn Gln Ser Ser Leu Ser Arg Thr Ser Thr Thr
            20                  25                  30

Thr Thr Gly Ser Pro Gln Thr Ala Tyr His Tyr Asn Phe Pro Gln Asn
        35                  40                  45

Asp Val Val Glu Glu Cys Phe Asn Phe Phe Met Asp Glu Glu Asp Leu
    50                  55                  60

Ser Ser Ser Ser Ser His His Asn His His Asn His Asn Asn Pro Asn
65                  70                  75                  80

Thr Tyr Tyr Ser Pro Phe Thr Thr Pro Thr Gln Tyr His Pro Ala Thr
                85                  90                  95

Ser Ser Thr Pro Ser Ser Thr Ala Ala Ala Ala Ala Leu Ala Ser Pro
            100                 105                 110

Tyr Ser Ser Gly His His Asn Asp Pro Ser Ala Phe Ser Ile Pro
        115                 120                 125

Gln Thr Pro Pro Ser Phe Asp Phe Ser Ala Asn Ala Lys Trp Ala Asp
    130                 135                 140

Ser Val Leu Leu Glu Ala Ala Arg Ala Phe Ser Asp Lys Asp Thr Ala
145                 150                 155                 160

Arg Ala Gln Gln Ile Leu Trp Thr Leu Asn Glu Leu Ser Ser Pro Tyr
                165                 170                 175

Gly Asp Thr Glu Gln Lys Leu Ala Ser Tyr Phe Leu Gln Ala Leu Phe
            180                 185                 190

Asn Arg Met Thr Gly Ser Gly Glu Arg Cys Tyr Arg Thr Met Val Thr
        195                 200                 205

Ala Ala Ala Thr Glu Lys Thr Cys Ser Phe Glu Ser Thr Arg Lys Thr
    210                 215                 220

Val Leu Lys Phe Gln Glu Val Ser Pro Trp Ala Thr Phe Gly His Val
225                 230                 235                 240

Ala Ala Asn Gly Ala Ile Leu Glu Ala Val Asp Gly Glu Ala Lys Ile
                245                 250                 255

His Ile Val Asp Ile Ser Ser Thr Phe Cys Thr Gln Trp Pro Thr Leu
            260                 265                 270
```

```
Leu Glu Ala Leu Ala Thr Arg Ser Asp Asp Thr Pro His Leu Arg Leu
            275                 280                 285

Thr Thr Val Val Ala Asn Lys Phe Val Asn Asp Gln Thr Ala Ser
290                 295                 300

His Arg Met Met Lys Glu Ile Gly Asn Arg Met Glu Lys Phe Ala Arg
305                 310                 315                 320

Leu Met Gly Val Pro Phe Lys Phe Asn Ile Ile His His Val Gly Asp
            325                 330                 335

Leu Ser Glu Phe Asp Leu Asn Glu Leu Asp Val Lys Pro Asp Glu Val
            340                 345                 350

Leu Ala Ile Asn Cys Val Gly Ala Met His Gly Ile Ala Ser Arg Gly
            355                 360                 365

Ser Pro Arg Asp Ala Val Ile Ser Ser Phe Arg Arg Leu Arg Pro Arg
            370                 375                 380

Ile Val Thr Val Val Glu Glu Ala Asp Leu Val Gly Glu Glu Glu
385                 390                 395                 400

Gly Gly Phe Asp Asp Glu Phe Leu Arg Gly Phe Gly Glu Cys Leu Arg
                405                 410                 415

Trp Phe Arg Val Cys Phe Glu Ser Trp Glu Glu Ser Phe Pro Arg Thr
            420                 425                 430

Ser Asn Glu Arg Leu Met Leu Glu Arg Ala Ala Gly Arg Ala Ile Val
            435                 440                 445

Asp Leu Val Ala Cys Glu Pro Ser Asp Ser Thr Glu Arg Arg Glu Thr
450                 455                 460

Ala Arg Lys Trp Ser Arg Met Arg Asn Ser Gly Phe Gly Ala Val
465                 470                 475                 480

Gly Tyr Ser Asp Glu Val Ala Asp Val Arg Ala Leu Leu Arg Arg
                485                 490                 495

Tyr Lys Glu Gly Val Trp Ser Met Val Gln Cys Pro Asp Ala Ala Gly
            500                 505                 510

Ile Phe Leu Cys Trp Arg Asp Gln Pro Val Val Trp Ala Ser Ala Trp
            515                 520                 525

Arg Pro Thr
530

<210> SEQ ID NO 29
<211> LENGTH: 504
<212> TYPE: PRT
<213> ORGANISM: Medicago truncatula

<400> SEQUENCE: 29

Met Asp Thr Leu Phe Arg Leu Val Asn Phe Gln Gln Gln Gln Gln
1               5                   10                  15

Tyr Gln Pro Asp Pro Ser Leu Asn Ser Thr Thr Leu Thr Thr Ser
            20                  25                  30

Ser Ser Ser Arg Ser Ser Arg Gln Thr Thr Tyr His Tyr Tyr Asn Gln
            35                  40                  45

Gln Glu Glu Asp Glu Glu Cys Phe Asn Asn Phe Tyr Tyr Met Asp His
        50                  55                  60

Asn Asn Asn Asp Glu Asp Leu Ser Ser Ser Ser Lys Gln His
65                  70                  75                  80

Tyr Tyr Thr Tyr Pro Tyr Ala Ser Thr Thr Ile Thr Thr Pro Asn
            85                  90                  95

Thr Thr Tyr Asn Thr Ile Asn Thr Pro Thr Thr Thr Asp Asn Tyr Ser
```

```
            100                 105                 110
Phe Ser Pro Ser His Asp Tyr Phe Asn Phe Glu Phe Ser Gly His Ser
        115                 120                 125

Trp Ser Gln Asn Ile Leu Leu Glu Thr Ala Arg Ala Phe Ser Asp Asn
130                 135                 140

Asn Thr Asn Arg Ile Gln Gln Leu Met Trp Met Leu Asn Glu Leu Ser
145                 150                 155                 160

Thr Pro Tyr Gly Asp Thr Asp Gln Lys Leu Ser Ser Tyr Phe Leu Gln
                165                 170                 175

Ala Leu Phe Ser Arg Met Asn Asp Ala Gly Asp Arg Thr Tyr Lys Thr
            180                 185                 190

Leu Thr Thr Ala Ser Glu Lys Thr Cys Ser Phe Asp Ser Thr Arg Lys
        195                 200                 205

Met Leu Leu Lys Phe Gln Glu Val Ser Pro Trp Thr Thr Phe Gly His
    210                 215                 220

Val Ala Ala Asn Gly Ala Ile Leu Glu Ala Leu Glu Gly Asn Pro Lys
225                 230                 235                 240

Leu His Ile Ile Asp Ile Ser Asn Thr Tyr Cys Thr Gln Trp Pro Thr
                245                 250                 255

Leu Leu Glu Ala Leu Ala Thr Arg Ser Asp Asp Thr Pro His Leu Arg
            260                 265                 270

Leu Thr Thr Val Val Thr Ala Ile Ser Gly Gly Ser Val Gln Lys Val
        275                 280                 285

Met Lys Glu Ile Gly Ser Arg Met Glu Lys Phe Ala Arg Leu Met Gly
    290                 295                 300

Val Pro Phe Lys Phe Lys Ile Ile Phe Ser Asp Leu Arg Glu Leu Asn
305                 310                 315                 320

Leu Cys Asp Leu Asp Ile Lys Glu Asp Glu Ala Leu Ala Ile Asn Cys
                325                 330                 335

Val Asn Ser Leu His Ser Ile Ser Gly Ala Gly Asn His Arg Asp Leu
            340                 345                 350

Phe Ile Ser Leu Leu Arg Gly Leu Glu Pro Arg Val Leu Thr Ile Val
        355                 360                 365

Glu Glu Glu Ala Asp Leu Glu Val Cys Phe Gly Ser Asp Phe Val Glu
    370                 375                 380

Gly Phe Lys Glu Cys Leu Arg Trp Phe Arg Val Tyr Phe Glu Ala Leu
385                 390                 395                 400

Asp Glu Ser Phe Ser Arg Thr Ser Ser Glu Arg Leu Met Leu Glu Arg
                405                 410                 415

Glu Ala Gly Arg Gly Ile Val Asp Leu Val Ala Cys Asp Pro Tyr Glu
            420                 425                 430

Ser Val Glu Arg Arg Glu Thr Ala Ala Arg Trp Arg Arg Leu His
        435                 440                 445

Gly Gly Gly Phe Asn Thr Val Ser Phe Ser Asp Glu Val Cys Asp Asp
    450                 455                 460

Val Arg Ala Leu Leu Arg Arg Tyr Lys Glu Gly Trp Ser Met Thr Ser
465                 470                 475                 480

Ser Asp Gly Asp Thr Gly Ile Phe Leu Ser Trp Lys Asp Lys Pro Val
                485                 490                 495

Val Trp Ala Ser Val Trp Arg Pro
            500

<210> SEQ ID NO 30
```

<211> LENGTH: 602
<212> TYPE: PRT
<213> ORGANISM: Oryza sativa

<400> SEQUENCE: 30

```
Met Asp Thr Leu Phe Arg Leu Val Ser Leu Gln Ala Ala Ser Glu Gln
1               5                   10                  15

Gln Gln Gln Gln Gln Gln Ser Ala Ser Tyr Asn Ser Arg Ser Thr Thr
            20                  25                  30

Ser Ser Gly Ser Arg Ser Ser His Gln Thr Asn Ala Ser Tyr Ser
        35                  40                  45

Tyr Tyr His His Ser Ser Asn Ser Gly Gly Gly Gly Gly Gly Gly
50                  55                      60

Gly Tyr Tyr Gly Gly Gln Gln Pro Pro Ser Gln Tyr Tyr Tyr
65              70                  75                  80

Leu Glu Pro Tyr Gln Glu Cys Gly Asn Ala Pro His His Gln Leu
                85                  90                  95

Tyr Met Asp Glu Asp Phe Ser Ser Ser Ser Ser Arg His Phe His
            100                 105                 110

His Gly Ala Arg Val Gln Gln Gln Pro Pro Ala Ser Ser Thr Pro
            115                 120                 125

Thr Gly Thr Ala Pro Thr Pro Pro Leu Ser Thr Ser Ser Thr Ala Ala
    130                 135                 140

Gly Ala Gly His Gly Leu Phe Glu Ala Ala Asp Leu Ser Phe Pro Pro
145                 150                 155                 160

Asp Leu Asn Leu Asp Phe Ser Ser Pro Ala Ser Ser Ser Gly Gly Gly
                165                 170                 175

Thr Ala Ser Ser Gly Ala Val Gly Gly Gly Gly Gly Arg Trp Ala
    180                 185                 190

Ser Gln Leu Leu Leu Glu Cys Ala Arg Ser Val Ala Ala Arg Asp Ser
            195                 200                 205

Gln Arg Val Gln Gln Leu Met Trp Met Leu Asn Glu Leu Ala Ser Pro
    210                 215                 220

Tyr Gly Asp Val Glu Gln Lys Leu Ala Ser Tyr Phe Leu Gln Gly Leu
225                 230                 235                 240

Phe Ala Arg Leu Thr Ala Ser Gly Pro Arg Thr Leu Arg Thr Leu Ala
                245                 250                 255

Ala Ala Ser Asp Arg Asn Thr Ser Phe Asp Ser Thr Arg Arg Thr Ala
            260                 265                 270

Leu Arg Phe Gln Glu Leu Ser Pro Trp Ser Ser Phe Gly His Val Ala
        275                 280                 285

Ala Asn Gly Ala Ile Leu Glu Ser Phe Leu Glu Val Ala Ala Ala
    290                 295                 300

Ser Ser Glu Thr Gln Arg Phe His Ile Leu Asp Leu Ser Asn Thr Phe
305                 310                 315                 320

Cys Thr Gln Trp Pro Thr Leu Leu Glu Ala Leu Ala Thr Arg Ser Ala
                325                 330                 335

Asp Glu Thr Pro His Leu Ser Ile Thr Thr Val Val Ser Ala Ala Pro
            340                 345                 350

Ser Ala Pro Thr Ala Ala Val Gln Arg Val Met Arg Glu Ile Gly Gln
        355                 360                 365

Arg Met Glu Lys Phe Ala Arg Leu Met Gly Val Pro Phe Arg Phe Arg
    370                 375                 380

Ala Val His His Ser Gly Asp Leu Ala Glu Leu Asp Leu Asp Ala Leu
```

-continued

```
            385                 390                 395                 400
    Asp Leu Arg Glu Gly Gly Ala Thr Thr Ala Leu Ala Val Asn Cys Val
                        405                 410                 415

Asn Ser Leu Arg Gly Val Val Pro Gly Arg Ala Arg Arg Asp Ala
                420                 425                 430

Phe Ala Ala Ser Leu Arg Arg Leu Asp Pro Arg Val Val Thr Val Val
                    435                 440                 445

Glu Glu Glu Ala Asp Leu Val Ala Ser Asp Pro Asp Ala Ser Ser Ala
    450                 455                 460

Thr Glu Glu Gly Gly Asp Thr Glu Ala Ala Phe Leu Lys Val Phe Gly
    465                 470                 475                 480

Glu Gly Leu Arg Phe Phe Ser Ala Tyr Met Asp Ser Leu Glu Glu Ser
                        485                 490                 495

Phe Pro Lys Thr Ser Asn Glu Arg Leu Ala Leu Glu Arg Gly Ala Gly
                    500                 505                 510

Arg Ala Ile Val Asp Leu Val Ser Cys Pro Ala Ser Glu Ser Met Glu
                515                 520                 525

Arg Arg Glu Thr Ala Ala Ser Trp Ala Arg Met Arg Ser Ala Gly
    530                 535                 540

Phe Ser Pro Val Ala Phe Ser Glu Asp Val Ala Asp Asp Val Arg Ser
    545                 550                 555                 560

Leu Leu Arg Arg Tyr Arg Glu Gly Trp Ser Met Arg Glu Ala Gly Thr
                        565                 570                 575

Asp Asp Ser Ala Ala Gly Ala Gly Val Phe Leu Ala Trp Lys Glu Gln
                    580                 585                 590

Pro Leu Val Trp Ala Ser Ala Trp Arg Pro
            595                 600

<210> SEQ ID NO 31
<211> LENGTH: 649
<212> TYPE: PRT
<213> ORGANISM: Artificial sequence
<220> FEATURE:
<223> OTHER INFORMATION: Synthetic sequence: Consensus sequence from
      Figure 15 of PCT/IB2008/001482
<220> FEATURE:
<221> NAME/KEY: VARIANT
<222> LOCATION: 11..24, 28..34, 36, 37, 41..44, 46..99, 103, 105..109,
      111
<223> OTHER INFORMATION: Xaa = any amino acid
<220> FEATURE:
<221> NAME/KEY: VARIANT
<222> LOCATION: 115..117, 123..140, 142..155, 157..172, 174..186, 188,
      190..201
<223> OTHER INFORMATION: Xaa = any amino acid
<220> FEATURE:
<221> NAME/KEY: VARIANT
<222> LOCATION: 204, 205, 209, 210, 219, 221
<223> OTHER INFORMATION: Xaa = any amino acid
<220> FEATURE:
<221> NAME/KEY: VARIANT
<222> LOCATION: (223)..(223)
<223> OTHER INFORMATION: Xaa is Asp or Asn
<220> FEATURE:
<221> NAME/KEY: VARIANT
<222> LOCATION: 225, 227
<223> OTHER INFORMATION: Xaa = any amino acid
<220> FEATURE:
<221> NAME/KEY: VARIANT
<222> LOCATION: (231)..(231)
<223> OTHER INFORMATION: Xaa is Met or Leu
<220> FEATURE:
<221> NAME/KEY: VARIANT
<222> LOCATION: (244)..(244)
<223> OTHER INFORMATION: Xaa = any amino acid
```

```
<220> FEATURE:
<221> NAME/KEY: VARIANT
<222> LOCATION: (245)..(245)
<223> OTHER INFORMATION: Xaa is Asp or Glu
<220> FEATURE:
<221> NAME/KEY: VARIANT
<222> LOCATION: 258, 260, 262, 265, 268
<223> OTHER INFORMATION: Xaa = any amino acid
<220> FEATURE:
<221> NAME/KEY: VARIANT
<222> LOCATION: (271)..(271)
<223> OTHER INFORMATION: Xaa is Met or Leu
<220> FEATURE:
<221> NAME/KEY: VARIANT
<222> LOCATION: 272, 276, 277
<223> OTHER INFORMATION: Xaa = any amino acid
<220> FEATURE:
<221> NAME/KEY: VARIANT
<222> LOCATION: (278)..(278)
<223> OTHER INFORMATION: Xaa is Asp or Glu
<220> FEATURE:
<221> NAME/KEY: VARIANT
<222> LOCATION: (280)..(281)
<223> OTHER INFORMATION: Xaa = any amino acid
<220> FEATURE:
<221> NAME/KEY: VARIANT
<222> LOCATION: (284)..(284)
<223> OTHER INFORMATION: Xaa is Asp or Glu
<220> FEATURE:
<221> NAME/KEY: VARIANT
<222> LOCATION: (289)..(290)
<223> OTHER INFORMATION: Xaa = any amino acid
<220> FEATURE:
<221> NAME/KEY: VARIANT
<222> LOCATION: (312)..(312)
<223> OTHER INFORMATION: Xaa is Met or Leu
<220> FEATURE:
<221> NAME/KEY: VARIANT
<222> LOCATION: (315)..(335), 337, 338, 349, 365
<223> OTHER INFORMATION: Xaa = any amino acid
<220> FEATURE:
<221> NAME/KEY: VARIANT
<222> LOCATION: (367)..(367)
<223> OTHER INFORMATION: Xaa is Asp or Glu
<220> FEATURE:
<221> NAME/KEY: VARIANT
<222> LOCATION: 372, 378, 380..396, 398, 399
<223> OTHER INFORMATION: Xaa = any amino acid
<220> FEATURE:
<221> NAME/KEY: VARIANT
<222> LOCATION: (408)..(408)
<223> OTHER INFORMATION: Xaa is Met or Leu
<220> FEATURE:
<221> NAME/KEY: VARIANT
<222> LOCATION: 420, 422, 423
<223> OTHER INFORMATION: Xaa = any amino acid
<220> FEATURE:
<221> NAME/KEY: VARIANT
<222> LOCATION: (424)..(424)
<223> OTHER INFORMATION: Xaa is Ile or Val
<220> FEATURE:
<221> NAME/KEY: VARIANT
<222> LOCATION: 427, 431
<223> OTHER INFORMATION: Xaa = any amino acid
<220> FEATURE:
<221> NAME/KEY: VARIANT
<222> LOCATION: (432)..(432)
<223> OTHER INFORMATION: Xaa is Asp or Glu
<220> FEATURE:
<221> NAME/KEY: VARIANT
<222> LOCATION: 434, 436, 437, 441, 444..446
<223> OTHER INFORMATION: Xaa = any amino acid
<220> FEATURE:
<221> NAME/KEY: VARIANT
<222> LOCATION: (451)..(451)
<223> OTHER INFORMATION: Xaa is Ile or Val
<220> FEATURE:
<221> NAME/KEY: VARIANT
<222> LOCATION: (457)..(457)
```

```
<223> OTHER INFORMATION: Xaa is Met or Leu
<220> FEATURE:
<221> NAME/KEY: VARIANT
<222> LOCATION: (459)..(459)
<223> OTHER INFORMATION: Xaa = any amino acid
<220> FEATURE:
<221> NAME/KEY: VARIANT
<222> LOCATION: (460)..(460)
<223> OTHER INFORMATION: Xaa is Ile or Val
<220> FEATURE:
<221> NAME/KEY: VARIANT
<222> LOCATION: 461..467, 470, 473, 477, 479
<223> OTHER INFORMATION: Xaa = any amino acid
<220> FEATURE:
<221> NAME/KEY: VARIANT
<222> LOCATION: 482, 485
<223> OTHER INFORMATION: Xaa is Ile or Val
<220> FEATURE:
<221> NAME/KEY: VARIANT
<222> LOCATION: 493..497, 499..512, 516, 518, 523
<223> OTHER INFORMATION: Xaa = any amino acid
<220> FEATURE:
<221> NAME/KEY: VARIANT
<222> LOCATION: (524)..(524)
<223> OTHER INFORMATION: Xaa is Phe or Tyr
<220> FEATURE:
<221> NAME/KEY: VARIANT
<222> LOCATION: (525)..(526)
<223> OTHER INFORMATION: Xaa = any amino acid
<220> FEATURE:
<221> NAME/KEY: VARIANT
<222> LOCATION: 529, 532
<223> OTHER INFORMATION: Xaa is Asp or Glu
<220> FEATURE:
<221> NAME/KEY: VARIANT
<222> LOCATION: 537, 548, 560, 561, 563, 565..568, 575, 576, 578
<223> OTHER INFORMATION: Xaa = any amino acid
<220> FEATURE:
<221> NAME/KEY: VARIANT
<222> LOCATION: (581)..(581)
<223> OTHER INFORMATION: Xaa is Met or Leu
<220> FEATURE:
<221> NAME/KEY: VARIANT
<222> LOCATION: 583, 590
<223> OTHER INFORMATION: Xaa = any amino acid
<220> FEATURE:
<221> NAME/KEY: VARIANT
<222> LOCATION: (591)..(591)
<223> OTHER INFORMATION: Xaa is Phe or Tyr
<220> FEATURE:
<221> NAME/KEY: VARIANT
<222> LOCATION: (593)..(594)
<223> OTHER INFORMATION: Xaa is Asp or Glu
<220> FEATURE:
<221> NAME/KEY: VARIANT
<222> LOCATION: 596, 610
<223> OTHER INFORMATION: Xaa = any amino acid
<220> FEATURE:
<221> NAME/KEY: VARIANT
<222> LOCATION: (613)..(613)
<223> OTHER INFORMATION: Xaa is Met or Leu
<220> FEATURE:
<221> NAME/KEY: VARIANT
<222> LOCATION: (614)..(628)
<223> OTHER INFORMATION: Xaa = any amino acid
<220> FEATURE:
<221> NAME/KEY: VARIANT
<222> LOCATION: (632)..(632)
<223> OTHER INFORMATION: Xaa is Phe or Tyr
<220> FEATURE:
<221> NAME/KEY: VARIANT
<222> LOCATION: (634)..(634)
<223> OTHER INFORMATION: Xaa = any amino acid
<220> FEATURE:
<221> NAME/KEY: VARIANT
<222> LOCATION: (637)..(637)
<223> OTHER INFORMATION: Xaa is Asp or Glu
<220> FEATURE:
<221> NAME/KEY: VARIANT
```

<222> LOCATION: (649)..(649)
<223> OTHER INFORMATION: Xaa = any amino acid

<400> SEQUENCE: 31

Met Asp Thr Leu Phe Arg Leu Val Ser Leu Gln Xaa Xaa Xaa Xaa
1               5                   10                  15

Xaa Xaa Xaa Xaa Xaa Xaa Xaa Gln Gln Gln Xaa Xaa Xaa Xaa Xaa
            20                  25                  30

Xaa Xaa Ser Xaa Xaa Ser Thr Ser Xaa Xaa Xaa Xaa Ser Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
            85                  90                  95

Xaa Xaa Xaa Glu Glu Cys Xaa Asn Xaa Xaa Xaa Xaa Phe Xaa Met
            100                 105                 110

Asp Glu Xaa Xaa Xaa Ser Ser Ser Ser Xaa Xaa Xaa Xaa Xaa Xaa
            115                 120                 125

Xaa Xaa Xaa Xaa Xaa Xaa Xaa Xaa Xaa Xaa Thr Xaa Xaa Xaa
    130                 135                 140

Xaa Xaa Xaa Xaa Xaa Xaa Xaa Xaa Xaa Xaa Thr Xaa Xaa Xaa
145                 150                 155                 160

Xaa Xaa Xaa Xaa Xaa Xaa Xaa Xaa Xaa Xaa Xaa Pro Xaa Xaa Xaa
            165                 170                 175

Xaa Xaa Xaa Xaa Xaa Xaa Xaa Xaa Ser Xaa Ser Xaa Xaa Xaa
            180                 185                 190

Xaa Xaa Xaa Xaa Xaa Xaa Xaa Ser Gly Xaa Xaa Lys Trp Ala
            195                 200                 205

Xaa Xaa Leu Leu Leu Glu Cys Ala Arg Ala Xaa Ser Xaa Lys Xaa Ser
    210                 215                 220

Xaa Arg Xaa Gln Gln Leu Xaa Trp Met Leu Asn Glu Leu Ala Ser Pro
225                 230                 235                 240

Tyr Gly Asp Xaa Xaa Gln Lys Leu Ala Ser Tyr Phe Leu Gln Ala Leu
                245                 250                 255

Phe Xaa Arg Xaa Thr Xaa Ser Gly Xaa Arg Cys Xaa Arg Thr Xaa Xaa
            260                 265                 270

Thr Ala Ser Xaa Xaa Xaa Lys Xaa Xaa Ser Phe Xaa Ser Thr Arg Lys
        275                 280                 285

Xaa Xaa Leu Lys Phe Gln Glu Val Ser Pro Trp Thr Thr Phe Gly His
    290                 295                 300

Val Ala Ala Asn Gly Ala Ile Xaa Glu Ala Xaa Xaa Xaa Xaa Xaa
305                 310                 315                 320

Xaa Xaa Xaa Xaa Xaa Xaa Xaa Xaa Xaa Xaa Xaa Xaa Xaa Xaa Gly
            325                 330                 335

Xaa Xaa Lys Leu His Ile Ile Asp Ile Ser Asn Thr Xaa Cys Thr Gln
        340                 345                 350

Trp Pro Thr Leu Leu Glu Ala Leu Ala Thr Arg Ser Xaa Asp Xaa Thr
            355                 360                 365

Pro His Leu Xaa Leu Thr Thr Val Val Xaa Ala Xaa Xaa Xaa Xaa
        370                 375                 380

Xaa Xaa Xaa Xaa Xaa Xaa Xaa Xaa Xaa Xaa Xaa Val Xaa Xaa Val
385                 390                 395                 400

```
Met Lys Glu Ile Gly Gln Arg Xaa Glu Lys Phe Ala Arg Leu Met Gly
                405                 410                 415

Val Pro Phe Xaa Phe Xaa Xaa Xaa His His Xaa Gly Asp Leu Xaa Xaa
            420                 425                 430

Leu Xaa Leu Xaa Xaa Leu Asp Val Xaa Glu Asp Xaa Xaa Xaa Glu Ala
        435                 440                 445

Leu Ala Xaa Asn Cys Val Gly Ala Xaa Arg Xaa Xaa Xaa Xaa Xaa Xaa
    450                 455                 460

Xaa Xaa Xaa Arg Asp Xaa Val Ile Xaa Ser Phe Arg Xaa Leu Xaa Pro
465                 470                 475                 480

Arg Xaa Val Thr Xaa Val Glu Glu Ala Asp Leu Xaa Xaa Xaa Xaa
                485                 490                 495

Xaa Asp Xaa Xaa Xaa Xaa Xaa Xaa Xaa Xaa Xaa Xaa Xaa Xaa Xaa
            500                 505                 510

Phe Val Lys Xaa Phe Xaa Glu Cys Leu Arg Xaa Xaa Xaa Xaa Tyr Phe
            515                 520                 525

Xaa Ser Leu Xaa Glu Ser Phe Pro Xaa Thr Ser Asn Glu Arg Leu Met
    530                 535                 540

Leu Glu Arg Xaa Ala Gly Arg Ala Ile Val Asp Leu Val Ala Cys Xaa
545                 550                 555                 560

Xaa Ser Xaa Ser Xaa Xaa Xaa Glu Arg Arg Glu Thr Ala Xaa Xaa
            565                 570                 575

Trp Xaa Arg Arg Xaa Arg Xaa Ala Gly Phe Ser Pro Val Xaa Xaa Ser
                580                 585                 590

Xaa Xaa Val Xaa Asp Asp Val Arg Ala Leu Leu Arg Arg Tyr Lys Glu
            595                 600                 605

Gly Xaa Trp Ser Xaa Xaa Xaa Xaa Xaa Xaa Xaa Xaa Xaa Xaa Xaa
        610                 615                 620

Xaa Xaa Xaa Xaa Ala Gly Ile Xaa Leu Xaa Trp Lys Xaa Gln Pro Val
625                 630                 635                 640

Val Trp Ala Ser Ala Trp Arg Pro Xaa
                645

<210> SEQ ID NO 32
<211> LENGTH: 34
<212> TYPE: DNA
<213> ORGANISM: Artificial sequence
<220> FEATURE:
<223> OTHER INFORMATION: Synthetic sequence: Primer

<400> SEQUENCE: 32
agaaagctgg gtaaccacca ccatcatcac tatc                              34

<210> SEQ ID NO 33
<211> LENGTH: 33
<212> TYPE: DNA
<213> ORGANISM: Artificial sequence
<220> FEATURE:
<223> OTHER INFORMATION: Synthetic sequence: Primer

<400> SEQUENCE: 33
aaaagcaggc tgctttcacc ttcaaatgct tcc                               33

<210> SEQ ID NO 34
<211> LENGTH: 20
<212> TYPE: DNA
<213> ORGANISM: Artificial sequence
<220> FEATURE:
```

<223> OTHER INFORMATION: Synthetic sequence: Primer

<400> SEQUENCE: 34
catcacctga ccttcactcc					20

<210> SEQ ID NO 35
<211> LENGTH: 21
<212> TYPE: DNA
<213> ORGANISM: Artificial sequence
<220> FEATURE:
<223> OTHER INFORMATION: Synthetic sequence: Primer

<400> SEQUENCE: 35
gttcggattg ttgttggaga c					21

<210> SEQ ID NO 36
<211> LENGTH: 21
<212> TYPE: DNA
<213> ORGANISM: Artificial sequence
<220> FEATURE:
<223> OTHER INFORMATION: Synthetic sequence: Primer

<400> SEQUENCE: 36
agcaacaaca acaacaatca g					21

<210> SEQ ID NO 37
<211> LENGTH: 19
<212> TYPE: DNA
<213> ORGANISM: Artificial sequence
<220> FEATURE:
<223> OTHER INFORMATION: Synthetic sequence: Primer

<400> SEQUENCE: 37
gcacactcac taagaagcc					19

<210> SEQ ID NO 38
<211> LENGTH: 21
<212> TYPE: DNA
<213> ORGANISM: Artificial sequence
<220> FEATURE:
<223> OTHER INFORMATION: Synthetic sequence: Primer

<400> SEQUENCE: 38
ccatcacctg accttcactc c					21

<210> SEQ ID NO 39
<211> LENGTH: 22
<212> TYPE: DNA
<213> ORGANISM: Artificial sequence
<220> FEATURE:
<223> OTHER INFORMATION: Synthetic sequence: Primer

<400> SEQUENCE: 39
tgttcggatt gttgttggag ac				22

<210> SEQ ID NO 40
<211> LENGTH: 5
<212> TYPE: PRT
<213> ORGANISM: Artificial sequence
<220> FEATURE:
<223> OTHER INFORMATION: Synthetic sequence: GRAS family-specific motif

<400> SEQUENCE: 40

Val His Ile Ile Asp
1               5

```
<210> SEQ ID NO 41
<211> LENGTH: 4
<212> TYPE: PRT
<213> ORGANISM: Artificial sequence
<220> FEATURE:
<223> OTHER INFORMATION: Synthetic sequence: Motif present in many GRAS
      protein family members

<400> SEQUENCE: 41

Arg Val Glu Arg
1
```